US008604046B2

(12) United States Patent
Gao et al.

(10) Patent No.: US 8,604,046 B2
(45) Date of Patent: Dec. 10, 2013

(54) SUBSTITUTED PIPERIDINE SPIRO PYRROLIDINONE AND PIPERIDINONE, PREPARATION AND THERAPEUTIC USE THEREOF

(75) Inventors: Zhongli Gao, Flemington, NJ (US); Daniel Hall, Hillsborough, NJ (US); Ryan Hartung, Tucson, AZ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/527,147

(22) Filed: Jun. 19, 2012

(65) Prior Publication Data

US 2012/0258979 A1     Oct. 11, 2012

Related U.S. Application Data

(60) Division of application No. 13/151,946, filed on Jun. 2, 2011, now Pat. No. 8,227,481, which is a continuation of application No. PCT/US2009/066673, filed on Dec. 4, 2009.

(60) Provisional application No. 61/120,088, filed on Dec. 5, 2008.

(30) Foreign Application Priority Data

Jul. 31, 2009    (FR) ...................... 09 55431

(51) Int. Cl.
*C07D 401/14*     (2006.01)
*A61K 31/438*     (2006.01)

(52) U.S. Cl.
USPC ............................. 514/278; 546/17

(58) Field of Classification Search
USPC ............................. 514/278; 546/17
See application file for complete search history.

(56) References Cited

U.S. PATENT DOCUMENTS

| | | | |
|---|---|---|---|
| 3,256,276 | A | 6/1966 | Grogan et al. |
| 7,223,788 | B2 | 5/2007 | Schwink et al. |
| 2007/0142538 | A1 | 6/2007 | Hirai |
| 2009/0137562 | A1 | 5/2009 | Allison et al. |
| 2010/0173898 | A1 | 7/2010 | Czechtizky et al. |
| 2010/0173949 | A1 | 7/2010 | Czechtizky et al. |

FOREIGN PATENT DOCUMENTS

| | | |
|---|---|---|
| EP | 1669350 | 6/2006 |
| WO | WO 02/42291 | 5/2002 |
| WO | WO 2004/037257 | 5/2004 |
| WO | WO 2007/067504 | 6/2007 |
| WO | WO 2007/133561 | 11/2007 |
| WO | WO 2008/157752 | 12/2008 |
| WO | WO 2009/039431 | 3/2009 |
| WO | WO 2009/052063 | 4/2009 |
| WO | WO 2009/052065 | 4/2009 |
| WO | WO 2010/058333 | 5/2010 |
| WO | WO 2010/065798 | 6/2010 |

OTHER PUBLICATIONS

U.S. Appl. No 13/151,925, Gao, et al., filed Jun. 2, 2011.
U.S. Appl. No. 13/483,503, Gao, et al., filed May 30, 2012.
Van Der Poel, A. M., et al., Temporal Patterning of Ultrasonic Distress Calls in the Adult Rat: Effects of Morphine and Benzodiazepines, Pyschopharmacology, (1989), vol. 97, pp. 147-148.
Esbeshade, T. A., et al., Histamine H3 Receptor Antagonists: Preclinical Promise for Treating Obesity and Cognitive Disorders, Molecular Interventions, (2006), vol. 6, No. 2, pp. 77-88.
Hancock, A. A., et al., The Challenge of Drug Discovery of a GPCR Target: Analysis of Preclinical Pharmacology of Histamine H3 Antagonits/Inverse Agonists, Biochemical Pharmacology, vol. 71, (2006), pp. 1103-1113.
Nagumo, S., et al., Synthesis of (-)-TAN1251A Using 4-Hydroxy-L-Proline as a Chiral Source, Tetrahedron, vol. 58, (2002), pp. 9871-9877.
Porsolt, et al., Depression: A New Animal Model Sensitive to Antidepressant Treatments, Nature, vol. 266, (1977), pp. 730-732.
Stafford, J. A., et al., Asymmetric Total Synthesis of (-)Secodaphniphylline, J. Org. Chem., (1990), vol. 55, pp. 5433-5434.
International Search Report for WO2010/065803 dated Jun. 10, 2010.
Raddatz, et al, Histamine H3 Antagonists for Treatment of Cognitive Deficits in CNS Diseases, Current Topics in Medicinal Chemistry, (2010), vol. 10, pp. 153-169.

*Primary Examiner* — Rita Desai
(74) *Attorney, Agent, or Firm* — Kelly L. Bender

(57) ABSTRACT

The present disclosure relates to a series of substituted N-phenyl-bipyrrolidine carboxamides of formula (I).

(I)

wherein $R_1$, $R_2$, $R_3$, m, n and p are as described herein. More specifically, the compounds of this invention are modulators of H3 receptors and are, therefore, useful as pharmaceutical agents, especially in the treatment and/or prevention of a variety of diseases modulated by H3 receptors including diseases associated with the central nervous system. Additionally, methods of preparation of substituted N-phenyl-bipyrrolidine carboxamides and intermediates therefor are disclosed.

5 Claims, No Drawings

SUBSTITUTED PIPERIDINE SPIRO PYRROLIDINONE AND PIPERIDINONE, PREPARATION AND THERAPEUTIC USE THEREOF

This application is a divisional of U.S. application Ser. No. 13/151,946, filed Jun. 2, 2011, now allowed, which is a continuation of International Application No. PCT/US2009/066673, filed Dec. 4, 2009, which claims the benefit of priority of U.S. Provisional Application No. 61/120,088, filed Dec. 5, 2008, all of which are incorporated herein by reference.

BACKGROUND OF THE INVENTION

1. Field of the Invention

The present invention relates to a series of substituted piperidine spiro pyrrolidinone and piperidinone derivatives. The compounds of this invention are modulators of H3 receptors and are, therefore, useful as pharmaceutical agents, especially in the treatment and/or prevention of a variety of diseases modulated by H3 receptors including diseases associated with the central nervous system. Additionally, this invention also relates to methods of preparation of substituted piperidine spiro pyrrolidinone and piperidinone and intermediates therefor.

2. Description of the Art

Histamine is a ubiquitous messenger molecule released from mast cells, enterochromaffin-like cells, and neurons. The physiological actions of histamine are mediated by four pharmacologically defined receptors (H1, H2, H3 and H4). All histamine receptors exhibit seven transmembrane domains and are members of the G-protein-coupled receptor superfamily (GPCRs).

The H1 receptor was the first member of the histamine receptor family to be pharmacologically defined, with the development of classical antihistamines (antagonists), such as diphenhydramine and fexofenadine. While antagonism of the H1 receptor of the immune system is commonly used for the treatment of allergic reactions, the H1 receptor is also expressed in various peripheral tissues and the central nervous system (CNS). In the brain, H1 is involved in the control of wakefulness, mood, appetite and hormone secretion.

The H2 receptor is also expressed in the CNS, where it may modulate several processes, including cognition. However, H2 receptor antagonists have primarily been developed to ameliorate gastric ulcers by inhibiting histamine-mediated gastric acid secretion by parietal cells. Classic H2 antagonists include cimetidine, ranitidine, and famotidine.

It should further be noted that H4 receptor function remains poorly defined, but may involve immune regulation and inflammatory processes.

On the other hand, H3 receptors have also been pharmacologically identified in the CNS, heart, lung, and stomach. The H3 receptor differs significantly from other histamine receptors, exhibiting low sequence homology (H1: 22%, H2: 21%, H4: 35%). H3 is a presynaptic autoreceptor on histamine neurons in the brain and a presynaptic heteroreceptor in non-histamine-containing neurons in both the central and peripheral nervous systems. In addition to histamine, H3 also modulates the release and/or synthesis of other neurotransmitters, including acetylcholine, dopamine, norepinepherin and serotonin. Of particular note, presynaptic modulation of histamine release by H3 allows significant regulation of H1 and H2 receptors in the brain. Modulating multiple neurotransmitter signaling pathways, H3 may contribute to varied physiological processes. Indeed, extensive preclinical evidence indicates that H3 plays a role in cognition, sleep-wake cycle and energy homeostasis.

Modulators of H3 function may be useful in the treatment of obesity and central nervous system disorders (Schizophrenia, Alzheimer's disease, attention-deficit hyperactivity disorder, Parkinson's disease, depression, and epilepsy), sleep disorders (narcolepsy and insomnia), cardiovascular disorders (acute myocardial infarction), respiratory disorders (asthma), and gastrointestinal disorders. See generally, Hancock. Biochem. Pharmacol. 2006 Apr. 14; 71(8):1103-13 and Esbenshade et al. Mol Interv. 2006 April; 6(2):77-88, 59.

U.S. Pat. No. 7,223,788 discloses a series of compounds, including substituted bis-pyrrolidines, having melanin concentrating hormone (MCH) receptor antagonists. But the compounds disclosed therein are not reported to be active at the H3 receptor site.

All of the references described herein are incorporated herein by reference in their entirety.

Accordingly, it is an object of this invention to provide a series of substituted piperidine spiro pyrrolidinone and piperidinone as selective H3 receptor ligands for treatment of H3 receptor regulated CNS disorders.

It is also an object of this invention to provide processes for the preparation of the substituted piperidine spiro pyrrolidinone and piperidinone as disclosed herein.

Other objects and further scope of the applicability of the present invention will become apparent from the detailed description that follows.

SUMMARY OF THE INVENTION

It has now been found that the compounds of formula (I) are useful as H3 receptor antagonists and/or inverse agonists. Thus in accordance with the practice of this invention there is provided a compound of formula (I):

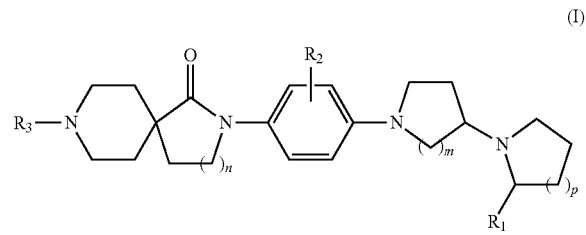

wherein
m is 1 or 2;
n is 1 or 2;
p is 1 or 2;
$R_1$ is hydrogen, $(C_1-C_6)$alkyl, $CF_3$, $(C_1-C_6)$alkoxy-$(C_1-C_6)$alkyl; and
$R_2$ is hydrogen, halogen, $(C_1-C_6)$alkyl or $CF_3$;
$R_3$ is hydrogen, $(C_1-C_6)$alkyl, $(C_3-C_7)$cycloalkyl, tert-butyloxycarbonyl, $(C_3-C_7)$cycloalkyl$(C_1-C_6)$alkyl, substituted or unsubstituted tetrahydropyranyl, substituted or unsubstituted tetrahydropyranylmethyl, substituted or unsubstituted furanylmethyl, substituted or unsubstituted benzyl, $(C_1-C_6)$alkoxymethyl carbonyl, substituted or unsubstituted $(C_3-C_7)$cycloalkane carbonyl, substituted or unsubstituted benzoyl, substituted or unsubstituted benzyl carbonyl, substituted or unsubstituted naphthyl carbonyl, substituted or unsubstituted pyridine carbonyl, substituted or unsubstituted furan carbonyl, substituted or unsubstituted tetrahydropyran carbonyl, substituted or unsubstituted benzene sulfonyl, wherein the substituents are selected from halogen, trifluoromethoxy, $(C_1-C_6)$alkoxy, $(C_1-C_6)$alkyl or $CF_3$, benzyloxycarbonyl.

This invention further includes various salts of the compounds of formula (I) including various enantiomers or diastereomers of compounds of formula (I).

In other aspects of this invention there are also provided various pharmaceutical compositions comprising one or more compounds of formula (I) as well as their therapeutic use in alleviating various diseases which are mediated in-part and/or fully by H3 receptors.

DETAILED DESCRIPTION OF THE INVENTION

The terms as used herein have the following meanings:

As used herein, the expression "$(C_1-C_6)$alkyl" includes methyl and ethyl groups, and straight-chained or branched propyl, and butyl groups. Particular alkyl groups are methyl, ethyl, n-propyl, isopropyl and tert-butyl. Derived expressions such as "$(C_1-C_6)$alkoxy", "$(C_1-C_6)$alkoxy$(C_1-C_6)$alkyl", or "hydroxy$(C_1-C_6)$alkyl" are to be construed accordingly.

As used herein, the expression "cycloalkyl" includes all of the known cyclic radicals. Representative examples of "cycloalkyl" include without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly.

As used herein, the expression "$(C_6-C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "$(C_6-C_{10})$arylsulfonyl," is to be construed accordingly.

As used herein, the expression "$(C_6-C_{10})$aryl$(C_1-C_4)$alkyl" means that the $(C_6-C_{10})$aryl as defined herein is further attached to $(C_1-C_4)$alkyl as defined herein. Representative examples include benzyl, phenylethyl, 2-phenylpropyl, 1-naphthylmethyl, 2-naphthylmethyl and the like. Similarly, the expression "$(C_6-C_{10})$arylcarbonyl" shall be construed accordingly. Representative examples include benzoyl, naphthylcarbonyl, and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals. Derived expression "heteroarylcarbonyl" shall be construed accordingly, e.g., pyridinecarbonyl, furancarbonyl, and the like.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, tetrahydropyranyl, and the like. Various other heterocycle radicals include, without any limitation, aziridinyl, azepanyl, diazepanyl, diazabicyclo[2.2.1]hept-2-yl, and triazocanyl, and the like. Derived expression "heterocyclecarbonyl" and "heterocycloalkyl$(C_1-C_6)$alkyl" shall be construed accordingly.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, nitric acid, sulfamic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, propionic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

As used herein, 'R' and 'S' are used as commonly used terms in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_2-C_6)$alkoxy, $(C_1-C_6)$thioalkyl, $(C_1-C_6)$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Thus, in accordance with the practice of this invention there is provided a compound of the formula I:

This invention further includes various salts of the compounds of formula (I) including various enantiomers or diastereomers of compounds of formula (I).

In other aspects of this invention there are also provided various pharmaceutical compositions comprising one or more compounds of formula (I) as well as their therapeutic use in alleviating various diseases which are mediated in-part and/or fully by H3 receptors.

Thus, in accordance with the practice of this invention there is provided a compound of the formula I:

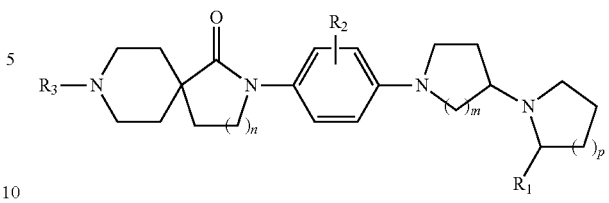

wherein
m is 1 or 2;
n is 1 or 2;
p is 1 or 2;
$R_1$ is hydrogen, $(C_1-C_4)$alkyl, $CF_3$, $(C_1-C_4)$alkoxy-$(C_1-C_4)$alkyl; and
$R_2$ is hydrogen, halogen, $(C_1-C_4)$alkyl or $CF_3$;
$R_3$ is hydrogen, $(C_1-C_6)$alkyl, $(C_1-C_6)$alkyloxycarbonyl, such as tert-butyloxycarbonyl, $(C_3-C_7)$cycloalkyl$(C_1-C_6)$alkyl, substituted or unsubstituted heterocycle, such as tetrahydropyranyl, substituted or unsubstituted heterocycloalkyl $(C_1-C_6)$alkyl, such as tetrahydropyranylmethyl, substituted or unsubstituted 5- or 6-membered ring heteroaryl $(C_1-C_6)$alkyl, such as furanylmethyl, substituted or unsubstituted benzyl, $(C_1-C_4)$alkoxymethylcarbonyl, substituted or unsubstituted $(C_3-C_7)$cycloalkanecarbonyl, substituted or unsubstituted benzylcarbonyl, substituted or unsubstituted $(C_6-C_{10})$arylcarbonyl, such as naphthylcarbonyl, benzoyl, etc., substituted or unsubstituted 5 or 6-membered ring heteroarylcarbonyl, such as pyridinecarbonyl or furancarbonyl, substituted or unsubstituted heterocyclecarbonyl, such as tetrahydropyrancarbonyl, substituted or unsubstituted benzenesulfonyl, wherein the substituents are selected from halogen, trifluoromethoxy, $(C_1-C_4)$alkoxy, $(C_1-C_4)$alkyl or $CF_3$.

This invention further includes various salts of the compounds of formula (I) including various enantiomers or diastereomers of compounds of formula (I). As noted hereinabove and by way of specific examples hereafter all of the salts that can be formed including pharmaceutically acceptable salts are part of this invention. As also noted hereinabove and hereafter all of the conceivable enantiomeric and diastereomeric forms of compounds of formula (I) are part of this invention.

In one of the embodiments, there is also provided the compounds of formula (I) wherein
n, p and m are 1;
$R_1$ is methyl, ethyl, isopropyl, n-propyl or methoxymethyl;
$R_2$ is hydrogen, fluorine, chlorine, methyl, ethyl or $CF_3$; and
$R_3$ is hydrogen, methoxymethylcarbonyl, tert-butyloxycarbonyl, cyclopropylmethyl, cyclopentylmethyl, cyclohexylmethyl, tetrahydropyranyl, benzyl, furanylmethyl, cyclopentane-carbonyl, cyclohexanecarbonyl, trifluoromethoxybenzoyl, fluorobenzoyl, benzyl-carbonyl, naphthylcarbonyl, benzenesulfonyl, fluorobenzene sulfonyl or methoxybenzenesulfonyl.

In another embodiment of this invention there is also provided a compound of formula (I), wherein n is 2 and m is 1; or n is 1 and m is 2; p is 1 or 2;
$R_1$ is methyl or ethyl;
$R_2$ is hydrogen, fluorine, chlorine, methyl, ethyl or $CF_3$; and
$R_3$ is hydrogen, isopropyl, tert-butyloxycarbonyl, cyclopropylmethyl, cyclopentylmethyl, cyclohexylmethyl, tetrahydropyranyl, benzyl, furanylmethyl, tetrahydropyranylmethyl, cyclopentanecarbonyl, cyclohexanecarbonyl, tetrahydropyrancarbonyl, benzoyl, trifluoromethoxybenzoyl, fluorobenzoyl, benzyl-carbonyl, naphthylcarbonyl, pyridinecarbonyl, furancarbonyl or benzenesulfonyl.

In a further aspect of this invention the following compounds encompassed by the scope of this invention without any limitation may be enumerated:

2-[2-methyl-4-((2R,3'S)-2-methyl-[1,3']bipyrrolidinyl-1'-yl)-phenyl]-1-oxo-2,8-diaza-spiro[4.5]decane-8-carboxylic acid tert-butyl ester;

2-[2-methyl-4-((2R,3'R)-2-methyl-[1,3']bipyrrolidinyl-1'-yl)-phenyl]-1-oxo-2,8-diaza-spiro[4.5]decane-8-carboxylic acid tert-butyl ester;

2-[2-methyl-4-((2S,3'R)-2-methyl-[1,3']bipyrrolidinyl-1'-yl)-phenyl]-1-oxo-2,8-diaza-spiro[4.5]decane-8-carboxylic acid tert-butyl ester;

2-[2-methyl-4-((2S,3'S)-2-methyl-[1,3']bipyrrolidinyl-1'-yl)-phenyl]-1-oxo-2,8-diaza-spiro[4.5]decane-8-carboxylic acid tert-butyl ester;

2-[2-methyl-4-(2-methyl-[1,3']bipyrrolidinyl-1'-yl)-phenyl]-1-oxo-2,8-diaza-spiro[4.5]decane-8-carboxylic acid tert-butyl ester 2-[2-methyl-4-((2S,3'S)-2-methyl-[1,3']bipyrrolidinyl-1'-yl)-phenyl]-1-oxo-2,9-diaza-spiro[5.5]undecane-9-carboxylic acid tert-butyl ester;

2-[4-((2S,3'S)-2-methyl-[1,3']bipyrrolidinyl-1'-yl)-phenyl]-1-oxo-2,9-diaza-spiro[5.5]undecane-9-carboxylic acid tert-butyl ester;

4-{[2-fluoro-4-((2S,3'S)-2-methyl-[1,3']bipyrrolidinyl-1'-yl)-phenyl]-methyl-carbamoyl}-4-propyl-piperidine-1-carboxylic acid tert-butyl ester;

2-{4-[4-(2S-2-methyl-pyrrolidin-1-yl)-piperidin-1-yl]-phenyl}-1-oxo-2,8-diaza-spiro[4.5]decane-8-carboxylic acid tert-butyl ester;

2-{4-[4-(2S-2-methyl-pyrrolidin-1-yl)-piperidin-1-yl]-2-trifluoromethyl-phenyl}-1-oxo-2,8-diaza-spiro[4.5]decane-8-carboxylic acid tert-butyl ester;

2-{4-[4-(2S-2-methyl-pyrrolidin-1-yl)-piperidin-1-yl]-2-fluoro-phenyl}-1-oxo-2,8-diaza-spiro[4.5]decane-8-carboxylic acid tert-butyl ester;

2-{4-[3-((2S,3'S)-2-methyl-piperidin-1-yl)-pyrrolidin-1-yl]-phenyl}-1-oxo-2,8-diaza-spiro[4.5]decane-8-carboxylic acid tert-butyl ester;

2-{4-[3-((2S,3'S)-2-methyl-piperidin-1-yl)-pyrrolidin-1-yl]-2-trifluoromethyl-phenyl}-1-oxo-2,8-diaza-spiro[4.5]decane-8-carboxylic acid tert-butyl ester;

2-{4-[3-((2S,3'S)-2-methyl-piperidin-1-yl)-pyrrolidin-1-yl]-2-fluoro-phenyl}-1-oxo-2,8-diaza-spiro[4.5]decane-8-carboxylic acid tert-butyl ester;

2-[2-methyl-4-((2S,3'S)-2-methyl-[1,3']bipyrrolidinyl-1'-yl)-phenyl]-2,8-diaza-spiro[4.5]decan-1-one;

8-cyclopentylmethyl-2-[2-methyl-4-(2-methyl-[1,3']bipyrrolidinyl-1'-1)-phenyl]-2,8-diaza-spiro[4.5]decan-1-one;

2-[2-methyl-4-((2S,3'S)-2-methyl-[1,3']bipyrrolidinyl-1'-yl)-phenyl]-8-(4-trifluoromethoxy-benzoyl)-2,8-diaza-spiro[4.5]decan-1-one;

8-benzenesulfonyl-2-{4-[4-(2S-2-methyl-pyrrolidin-1-yl)-piperidin-1-yl]-phenyl}-2,8-diaza-spiro[4.5]decan-1-one;

8-(4-methoxy-benzenesulfonyl)-2-[4-((2S,3'S)-2-methyl-[1,3']-bipyrrolidinyl-1'-yl)-2-trifluoromethyl-phenyl]-2,8-diaza-spiro[4.5]decan-1-one;

2-[4-((2S,3'S)-2-methyl-[1,3']-bipyrrolidinyl-1'-yl)-2-trifluoromethyl-phenyl]-2,8-diaza-spiro[4.5]decan-1-one 2-[2-methyl-4-((2S,3'S)-2-methyl-[1,3']-bipyrrolidinyl-1'-yl)-phenyl]-2,8-diaza-spiro[4.5]decan-1-one;

2-[2-methyl-4-((2R,3'R)-2-methyl-[1,3']-bipyrrolidinyl-1'-yl)-phenyl]-2,8-diaza-spiro[4.5]decan-1-one Hydrochloride;

2-[2-methyl-4-((2R,3'S)-2-methyl-[1,3']-bipyrrolidinyl-1'-yl)-phenyl]-2,8-diaza-spiro[4.5]decan-1-one Hydrochloride;

2-[2-methyl-4-((2S,3'R)-2-methyl-[1,3']-bipyrrolidinyl-1'-yl)-phenyl]-2,8-diaza-spiro[4.5]decan-1-one Hydrochloride;

8-cyclopentylmethyl-2-[2-methyl-4-((2R,3'S)-2-methyl-[1,3']-bipyrrolidinyl-1'-l)-phenyl]-2,8-diaza-spiro[4.5]decan-1-one;

8-cyclopentylmethyl-2-[2-methyl-4-((2R,3'R)-2-methyl-[1,3']-bipyrrolidinyl-1'-l)-phenyl]-2,8-diaza-spiro[4.5]decan-1-one;

8-cyclopentylmethyl-2-[2-methyl-4-((2S,3'R)-2-methyl-[1,3']bipyrrolidinyl-1'-l)-phenyl]-2,8-diaza-spiro[4.5]decan-1-one;

8-cyclopentylmethyl-2-[2-methyl-4-((2S,3'S)-2-methyl-[1,3']bipyrrolidinyl-1'-l)-phenyl]-2,8-diaza-spiro[4.5]decan-1-one;

2-[2-methyl-4-((2R,3'S)-2-methyl-[1,3']-bipyrrolidinyl-1'-yl)-phenyl]-8-(4-trifluoromethoxy-benzoyl)-2,8-diaza-spiro[4.5]decan-1-one;

2-[2-methyl-4-((2R,3'R)-2-methyl-[1,3']-bipyrrolidinyl-1'-yl)-phenyl]-8-(4-trifluoromethoxy-benzoyl)-2,8-diaza-spiro[4.5]decan-1-one;

2-[2-methyl-4-((2S,3'R)-2-methyl-[1,3']-bipyrrolidinyl-1'-yl)-phenyl]-8-(4-trifluoromethoxy-benzoyl)-2,8-diaza-spiro[4.5]decan-1-one;

2-[2-methyl-4-(2-methyl-[1,3']bipyrrolidinyl-1'-yl)-phenyl]-8-(4-trifluoromethoxy-benzoyl)-2,8-diaza-spiro[4.5]decan-1-one;

3-[2-methyl-4-((2S,3'S)-2-methyl-[1,3']-bipyrrolidinyl-1'-yl)-phenyl]-2,9-diaza-spiro[5.5]undecan-1-one;

3-[4-((2S,3'S)-2-methyl-[1,3']-bipyrrolidinyl-1'-yl)-phenyl]-2,9-diaza-spiro[5.5]undecan-1-one;

3-[2-fluoro-4-((2S,3'S)-2-methyl-[1,3']-bipyrrolidinyl-1'-yl)-phenyl]-2,9-diaza-spiro[5.5]undecan-1-one;

3-[2-methyl-4-((2S,3'S)-2-methyl-[1,3']-bipyrrolidinyl-1'-yl)-phenyl]-9-(pyridine-4-carbonyl)-2,9-diaza-spiro[5.5]undecan-1-one;

9-(furan-3-carbonyl)-2-[2-methyl-4-((2S,3'S)-2-methyl-[1,3']bipyrrolidinyl-1'-yl)-phenyl]-2,9-diaza-spiro[5.5]undecan-1-one;

9-benzoyl-2-[4-((2S,3'S)-2-methyl-[1,3']bipyrrolidinyl-1'-yl)-phenyl]-2,9-diaza-spiro[5.5]undecan-1-one;

9-(4-fluoro-benzoyl-2-[4-((2S,3'S)-2-methyl-[1,3']bipyrrolidinyl-1'-yl)-phenyl]-2,9-diaza-spiro[5.5]undecan-1-one;

9-cyclohexanecarbonyl-2-[2-fluoro-4-((2S,3'S)-2-methyl-[1,3']bipyrrolidinyl-1'-yl)-phenyl]-2,9-diaza-spiro[5.5]undecan-1-one;

2-[2-fluoro-4-((2S,3'S)-2-methyl-[1,3']bipyrrolidinyl-1'-yl)-phenyl]-9-(tetrahydro-pyran-4-carbonyl)-2,9-diaza-spiro[5.5]undecan-1-one;

9-isopropyl-2-[2-methyl-4-((2S,3'S)-2-methyl-[1,3']-bipyrrolidinyl-1'-yl)-phenyl]-2,9-diaza-spiro[5.5]undecan-1-one;

9-cyclohexylmethyl-2-[2-methyl-4-((2S,3'S)-2-methyl-[1,3']bipyrrolidinyl-1'-yl)-phenyl]-2,9-diaza-spiro[5.5]undecan-1-one;

9-cyclopropylmethyl-2-[4-((2S,3'S)-2-methyl-[1,3']bipyrrolidinyl-1'-yl)-phenyl]-2,9-diaza-spiro[5.5]undecan-1-one;

2-[4-((2S,3'S)-2-methyl-[1,3']bipyrrolidinyl-1'-yl)-phenyl]-9-(tetrahydro-pyran-4-yl)-2,9-diaza-spiro[5.5]undecan-1-one;

9-benzyl-2-[2-fluoro-4-((2S,3'S)-2-methyl-[1,3']-bipyrrolidinyl-1'-yl)-phenyl]-2,9-diaza-spiro[5.5]undecan-1-one;

2-[2-fluoro-4-((2S,3'S)-2-methyl-[1,3']-bipyrrolidinyl-1'-yl)-phenyl]-9-furan-2-ylmethyl-2,9-diaza-spiro[5.5]undecan-1-one;
2-{4-[4-(2S-2-methyl-pyrrolidin-1-yl)-piperidin-1-yl]-phenyl}-2,8-diaza-spiro[4.5]decan-1-one;
2-{4-[4-(2S-2-methyl-pyrrolidin-1-yl)-piperidin-1-yl]-2-trifluoromethyl-phenyl}-2,8-diaza-spiro[4.5]decan-1-one;
2-{4-[4-(2S-2-methyl-pyrrolidin-1-yl)-piperidin-1-yl]-2-fluoro-phenyl}-2,8-diaza-spiro[4.5]decan-1-one;
2-{4-[3-((2S,3'S)-2-methyl-piperidin-1-yl)-pyrrolidin-1-yl]-phenyl}-2,8-diaza-spiro[4.5]decan-1-one;
2-{4-[3-((2S,3'S)-2-methyl-piperidin-1-yl)-pyrrolidin-1-yl]-2-trifluoromethyl-phenyl}-2,8-diaza-spiro[4.5]decan-1-one;
2-{4-[3-((2S,3'S)-2-methyl-piperidin-1-yl)-pyrrolidin-1-yl]-2-fluoro-phenyl}-2,8-diaza-spiro[4.5]decan-1-one;
8-(4-fluoro-benzoyl)-2-{4-[4-(2S-2-methyl-pyrrolidin-1-yl)-piperidin-1-yl]-phenyl}-2,8-diaza-spiro[4.5]decan-1-one;
8-cyclohexanecarbonyl-2-{2-fluoro-4-[4-(2S-2-methyl-pyrrolidin-1-yl)-piperidin-1-yl]-phenyl}-2,8-diaza-spiro[4.5]decan-1-one;
8-(4-fluoro-benzenesulfonyl)-2-{4-[3-((2S,3'S)-2-methyl-piperidin-1-yl)-pyrrolidin-1-yl]-phenyl}-2,8-diaza-spiro[4.5]decan-1-one;
2-{4-[3-((2S,3'S)-2-methyl-piperidin-1-yl)-pyrrolidin-1-yl]-phenyl}-8-(tetrahydro-pyran-4-carbonyl)-2,8-diaza-spiro[4.5]decan-1-one;
8-cyclopentanecarbonyl-2-{4-[3-((2S,3'S)-2-methyl-piperidin-1-yl)-pyrrolidin-1-yl]-2-trifluoromethyl-phenyl}-2,8-diaza-spiro[4.5]decan-1-one;
8-cyclopropylmethyl-2-{2-fluoro-4-[4-(2S-2-methyl-pyrrolidin-1-yl)-piperidin-1-yl]-phenyl}-2,8-diaza-spiro[4.5]decan-1-one;
8-cyclopentylmethyl-2-{2-fluoro-4-[4-(2S-2-methyl-pyrrolidin-1-yl)-piperidin-1-yl]-phenyl}-2,8-diaza-spiro[4.5]decan-1-one;
8-cyclohexylmethyl-2-{4-[3-((2S,3'S)-2-methyl-piperidin-1-yl)-pyrrolidin-1-yl]-2-trifluoromethyl-phenyl}-2,8-diaza-spiro[4.5]decan-1-one;
2-{2-fluoro-4-[3-((2S,3'S)-2-methyl-piperidin-1-yl)-pyrrolidin-1-yl]-phenyl}-8-(tetrahydro-pyran-4-ylmethyl)-2,8-diaza-spiro[4.5]decan-1-one;
2-[4-((2S,3'S)-2-methyl-[1,3']bipyrrolidinyl-1'-yl)-2-trifluoromethyl-phenyl]-8-phenylacetyl-2,8-diaza-spiro[4.5]decan-1-one;
8-(2-methoxy-acetyl)-2-[4-((2S,3'S)-2-methyl-[1,3']bipyrrolidinyl-1'-yl)-2-trifluoromethyl-phenyl]-2,8-diaza-spiro[4.5]decan-1-one;
2-[4-((2S,3'S)-2-methyl-[1,3']bipyrrolidinyl-1'-yl)-2-trifluoromethyl-phenyl]-8-(naphthalene-2-carbonyl)-2,8-diaza-spiro[4.5]decan-1-one;
8-benzoyl-2-[4-((2S,3'S)-2-methyl-[1,3']bipyrrolidinyl-1'-yl)-2-trifluoromethyl-phenyl]-2,8-diaza-spiro[4.5]decan-1-one;
8-(furan-3-carbonyl)-2-[4-((2S,3'S)-2-methyl-[1,3']bipyrrolidinyl-1'-yl)-2-trifluoromethyl-phenyl]-2,8-diaza-spiro[4.5]decan-1-one;
8-furan-2-ylmethyl-2-[4-((2S,3'S)-2-methyl-[1,3']bipyrrolidinyl-1'-yl)-2-trifluoromethyl-phenyl]-2,8-diaza-spiro[4.5]decan-1-one;
8-cyclopropylmethyl-2-[4-((2S,3'S)-2-methyl-[1,3']bipyrrolidinyl-1'-yl)-2-trifluoromethyl-phenyl]-2,8-diaza-spiro[4.5]decan-1-one;
2-[4-((2S,3'S)-2-methyl-[1,3']bipyrrolidinyl-1'-yl)-2-trifluoromethyl-phenyl]-8-(tetrahydro-pyran-4-ylmethyl)-2,8-diaza-spiro[4.5]decan-1-one; and
2-[4-((2S,3'S)-2-methyl-[1,3']bipyrrolidinyl-1'-yl)-2-trifluoromethyl-phenyl]-2,8-diaza-spiro[4.5]decan-1-one.

All of the above compounds may also include corresponding salts wherever possible including the pharmaceutically acceptable salts thereof.

In another aspect of this invention the following compounds encompassed by compound of formula (I) of this invention without any limitation may be enumerated:

8-cyclopentylmethyl-2-[2-methyl-4-((2R,3'S)-2-methyl-[1,3']bipyrrolidinyl-1'-l)-phenyl]-2,8-diaza-spiro[4.5]decan-1-one;
8-cyclopentylmethyl-2-[2-methyl-4-((2R,3'R)-2-methyl-[1,3']bipyrrolidinyl-1'-l)-phenyl]-2,8-diaza-spiro[4.5]decan-1-one;
8-cyclopentylmethyl-2-[2-methyl-4-((2S,3'R)-2-methyl-[1,3']bipyrrolidinyl-1'-l)-phenyl]-2,8-diaza-spiro[4.5]decan-1-one;
8-cyclopentylmethyl-2-[2-methyl-4-((2S,3'S)-2-methyl-[1,3']bipyrrolidinyl-1'-l)-phenyl]-2,8-diaza-spiro[4.5]decan-1-one;
2-[2-methyl-4-((2R,3'S)-2-methyl-[1,3']bipyrrolidinyl-1'-yl)-phenyl]-8-(4-trifluoromethoxy-benzoyl)-2,8-diaza-spiro[4.5]decan-1-one;
2-[2-methyl-4-((2R,3'R)-2-methyl-[1,3']bipyrrolidinyl-1'-yl)-phenyl]-8-(4-trifluoromethoxy-benzoyl)-2,8-diaza-spiro[4.5]decan-1-one;
2-[2-methyl-4-((2S,3'R)-2-methyl-[1,3']bipyrrolidinyl-1'-yl)-phenyl]-8-(4-trifluoromethoxy-benzoyl)-2,8-diaza-spiro[4.5]decan-1-one;
2-[2-methyl-4-(2-methyl-[1,3']bipyrrolidinyl-1'-yl)-phenyl]-8-(4-trifluoromethoxy-benzoyl)-2,8-diaza-spiro[4.5]decan-1-one;
3-[2-methyl-4-((2S,3'S)-2-methyl-[1,3']bipyrrolidinyl-1'-yl)-phenyl]-2,9-diaza-spiro[5.5]undecan-1-one;
3-[4-((2S,3'S)-2-methyl-[1,3']bipyrrolidinyl-1'-yl)-phenyl]-2,9-diaza-spiro[5.5]undecan-1-one;
3-[2-fluoro-4-((2S,3'S)-2-methyl-[1,3']bipyrrolidinyl-1'-yl)-phenyl]-2,9-diaza-spiro[5.5]undecan-1-one;
9-isopropyl-2-[2-methyl-4-((2S,3'S)-2-methyl-[1,3']bipyrrolidinyl-1'-yl)-phenyl]-2,9-diaza-spiro[5.5]undecan-1-one;
9-cyclohexylmethyl-2-[2-methyl-4-((2S,3'S)-2-methyl-[1,3']bipyrrolidinyl-1'-yl)-phenyl]-2,9-diaza-spiro[5.5]undecan-1-one;
9-cyclopropylmethyl-2-[4-((2S,3'S)-2-methyl-[1,3']bipyrrolidinyl-1'-yl)-phenyl]-2,9-diaza-spiro[5.5]undecan-1-one;
2-[4-((2S,3'S)-2-methyl-[1,3']bipyrrolidinyl-1'-yl)-phenyl]-9-(tetrahydro-pyran-4-yl)-2,9-diaza-spiro[5.5]undecan-1-one;
9-benzyl-2-[2-fluoro-4-((2S,3'S)-2-methyl-[1,3']bipyrrolidinyl-1'-yl)-phenyl]-2,9-diaza-spiro[5.5]undecan-1-one;
2-[2-fluoro-4-((2S,3'S)-2-methyl-[1,3']bipyrrolidinyl-1'-yl)-phenyl]-9-furan-2-ylmethyl-2,9-diaza-spiro[5.5]undecan-1-one;
8-cyclopropylmethyl-2-{2-fluoro-4-[4-(2S-2-methyl-pyrrolidin-1-yl)-piperidin-1-yl]-phenyl}-2,8-diaza-spiro[4.5]decan-1-one;
8-cyclopentylmethyl-2-{2-fluoro-4-[4-(2S-2-methyl-pyrrolidin-1-yl)-piperidin-1-yl]-phenyl}-2,8-diaza-spiro[4.5]decan-1-one;
2-{2-fluoro-4-[3-((2S,3'S)-2-methyl-piperidin-1-yl)-pyrrolidin-1-yl]-phenyl}-8-(tetrahydro-pyran-4-ylmethyl)-2,8-diaza-spiro[4.5]decan-1-one;
8-furan-2-ylmethyl-2-[4-((2S,3'S)-2-methyl-[1,3']bipyrrolidinyl-1'-yl)-2-trifluoromethyl-phenyl]-2,8-diaza-spiro[4.5]decan-1-one;

8-cyclopropylmethyl-2-[4-((2S,3'S)-2-methyl-[1,3']bipyrrolidinyl-1'-yl)-2-trifluoromethyl-phenyl]-2,8-diaza-spiro[4.5]decan-1-one; and 2-[4-((2S,3'S)-2-methyl-[1,3']bipyrrolidinyl-1'-yl)-2-trifluoromethyl-phenyl]-8-(tetrahydro-pyran-4-ylmethyl)-2,8-diaza-spiro[4.5]decan-1-one;

Again all of the conceivable salts of the above noted compounds including the pharmaceutically acceptable salts are part of this invention.

In another aspect of this invention the compound of this invention may be represented by a specific stereoisomeric form of formula (II):

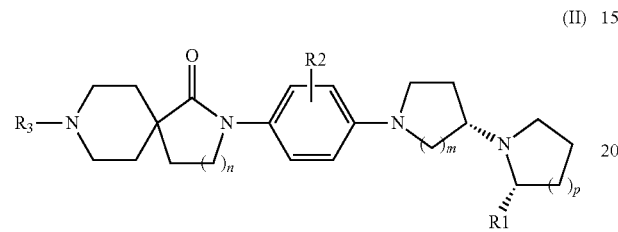

(II)

Wherein $R_1$, $R_2$, $R_3$, m, n and p are as defined hereinabove.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein. For instance, see R. C. Larock, "Comprehensive Organic Transformations," VCH publishers, 1989.

It is also well known that in various organic reactions it may be necessary to protect reactive functional groups, such as for example, amino groups, to avoid their unwanted participation in the reactions. Conventional protecting groups may be used in accordance with standard practice and known to one of skilled in the art, for example, see T. W. Greene and P. G. M. Wuts in "Protective Groups in Organic Chemistry" John Wiley and Sons, Inc., 1991. For example, suitable amine protecting groups include without any limitation sulfonyl (e.g., tosyl), acyl (e.g., benzyloxycarbonyl or t-butoxycarbonyl) and arylalkyl (e.g., benzyl), which may be removed subsequently by hydrolysis or hydrogenation as appropriate. Other suitable amine protecting groups include trifluoroacetyl [—C(=O)CF$_3$] which may be removed by base catalyzed hydrolysis, or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl, which may be removed by acid catalyzed hydrolysis, for example with TFA.

More specifically, the compounds disclosed herein and various precursors used therefor can be synthesized according to the following procedures of Schemes 1-5, wherein $R_1$, $R_2$, $R_3$, m and n are as defined for Formula I unless otherwise indicated.

For instance, Scheme 1 illustrates the preparation of the intermediate [1,3]-pyrrolidinyl-pyrrolidine of formula (4), wherein R is as defined herein. First, in step 1, Scheme 1, suitably protected (for example tert-butyloxycarbonyl (boc)) pyrrolidinone of formula (1) is condensed with a desired substituted pyrrolidine of formula (2) by any of the known reductive amination procedures to form an intermediate of formula (3). For instance, such condensation reactions are generally carried out in the presence of reducing agents such as triacetoxyborohydride in an inert atmosphere, such as nitrogen atmosphere. The reaction can be carried out either at sub-ambient, ambient or super-ambient reaction temperatures and pressures. Typically, such reactions are carried out at room temperature at atmospheric pressure of nitrogen. The reaction mixture is then worked-up using procedures known to skilled in the art to isolate the intermediate of formula (3).

In step 2, Scheme 1, the intermediate (3) is then de-protected to form the desired [1,3']-pyrrolidinyl-pyrrolidine of formula (4). Such deprotection reactions are generally carried out under acidic conditions, for example, in the presence of hydrochloric acid at sub-ambient to ambient temperatures, for example in the temperature range of about −10° C. to room temperature. However, other suitable reaction temperatures can also be used depending upon the nature of the intermediate of formula (3).

Scheme 1

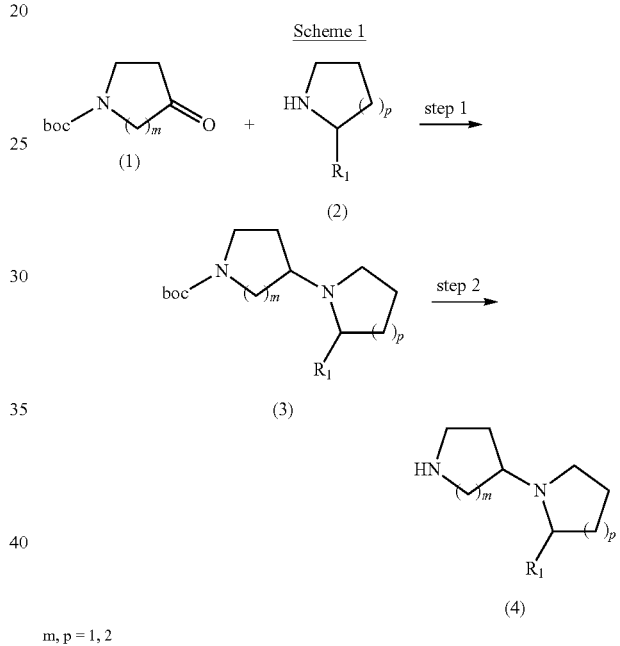

m, p = 1, 2

Scheme 2 illustrates preparation of enantiomerically pure isomers of the [1,3']pyrrolidinyl-pyrrolidine of formula (9), wherein R is as defined herein. In step 1, Scheme 2, suitably protected (for example boc) pyrrolidine or piperidine alcohol of formula (5) is treated with p-toluene sulfonyl chloride to form intermediate of formula (6). This reaction can be carried out using any of the procedures known to one skilled in the art, such as for example carrying out the reaction in the presence of a suitable base such as triethylamine and DMAP in a suitable organic solvent, preferably an aprotic solvent such as dichloromethane at sub-ambient or ambient temperature conditions.

In step 2, Scheme 2, the intermediate of formula (6) is condensed with a desired pyrrolidine or piperidine of formula (7). Again, such condensation reactions can be carried out using any of the procedures known to one skilled in the art in order to obtain the intermediate of formula (8). Typically, such condensation reactions are carried out in the presence of a base such as potassium carbonate in the presence of solvents such as acetonitrile at ambient to super-ambient temperature conditions.

In step 3, Scheme 2, the intermediate of formula (8) is then reacted with an acid, such as hydrochloric acid in a suitable solvent, such as dioxane, to form the desired stereospecific isomer of intermediate of formula (9). It has now been found that the intermediates of formula (9) can be readily formed in accordance with the process of this invention with high enantiomeric purity, specific details of which are provided hereinbelow by way of various examples. In general, the enantiomeric purity can be determined by chiral HPLC.

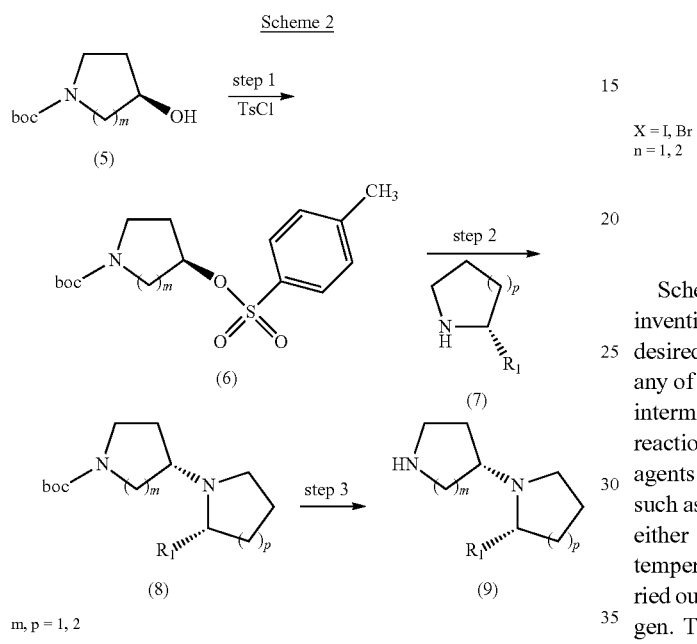

Scheme 2 m, p = 1, 2

Scheme 3 illustrates the preparation of the intermediate of formula (13). In step 1, Scheme 3, commercially available piperidine-1,4-dicarboxylic acid 1-tert-butyl ester 4-ethyl ester, of formula (10) is treated with suitable base, such as nBuLi in presence of HMPA in THF, followed by alkenyl halides, to form intermediate of formula (12). This reaction can be carried out using any of the procedures known to one skilled in the art, such as reported in the literature (Nagumo, S.; Matoba A.; et al, Tetrahedron, 2002, 58(49), 9871-9877; Stafford, J. A.; Heathcock, C. H. J. Org. Chem., 1990, 55(20), 5433-5434). In step 2, Scheme 3, the alkene (12) is cleaved with $OsO_4$ and $NaIO_4$ in propanol and water to form aldehyde (13).

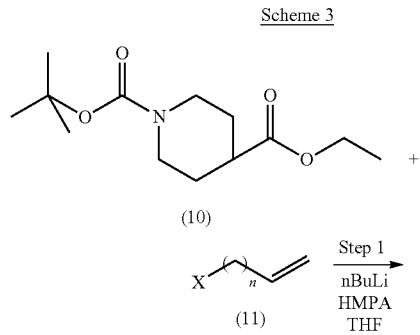

Scheme 3

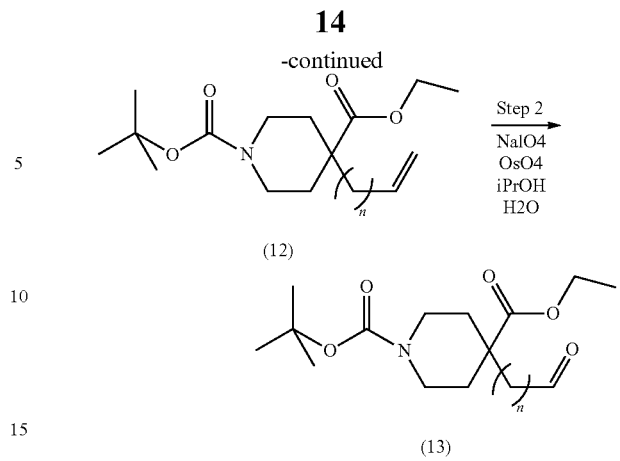

X = I, Br
n = 1, 2

Scheme 4 illustrates the preparation of compounds of this invention. The aldehyde of formula (13) is condensed with a desired commercially available bromide of formula (16) by any of the known reductive amination procedures to form an intermediate of formula (17). For instance, such condensation reactions are generally carried out in the presence of reducing agents such as triacetoxyborohydride in an inert atmosphere, such as nitrogen atmosphere. The reaction can be carried out either at sub-ambient, ambient or super-ambient reaction temperatures and pressures. Typically, such reactions are carried out at room temperature at atmospheric pressure of nitrogen. The reaction mixture is then worked-up using procedures known to skilled in the art to isolate the intermediate of formula (17). The cyclization is then initiated by catalytic amount of base, such as potassium t-butoxide in aprotic solvents, such THF, to form compounds of formula (18). The intermediate of formula (18) is then condensed with the amine intermediate (4) or (9) prepared according to Scheme 1 and 2 to form the compounds of this invention (19).

Scheme 4

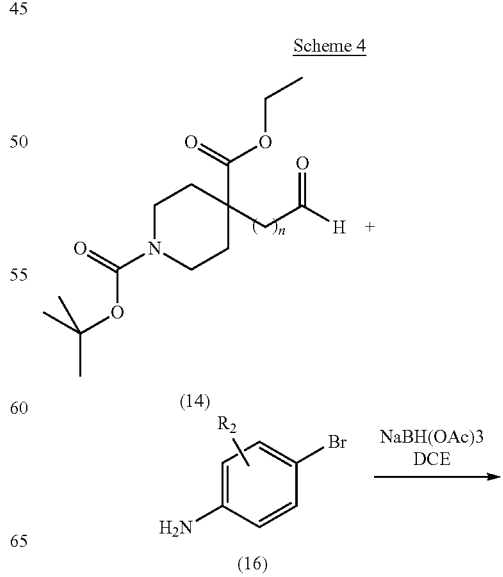

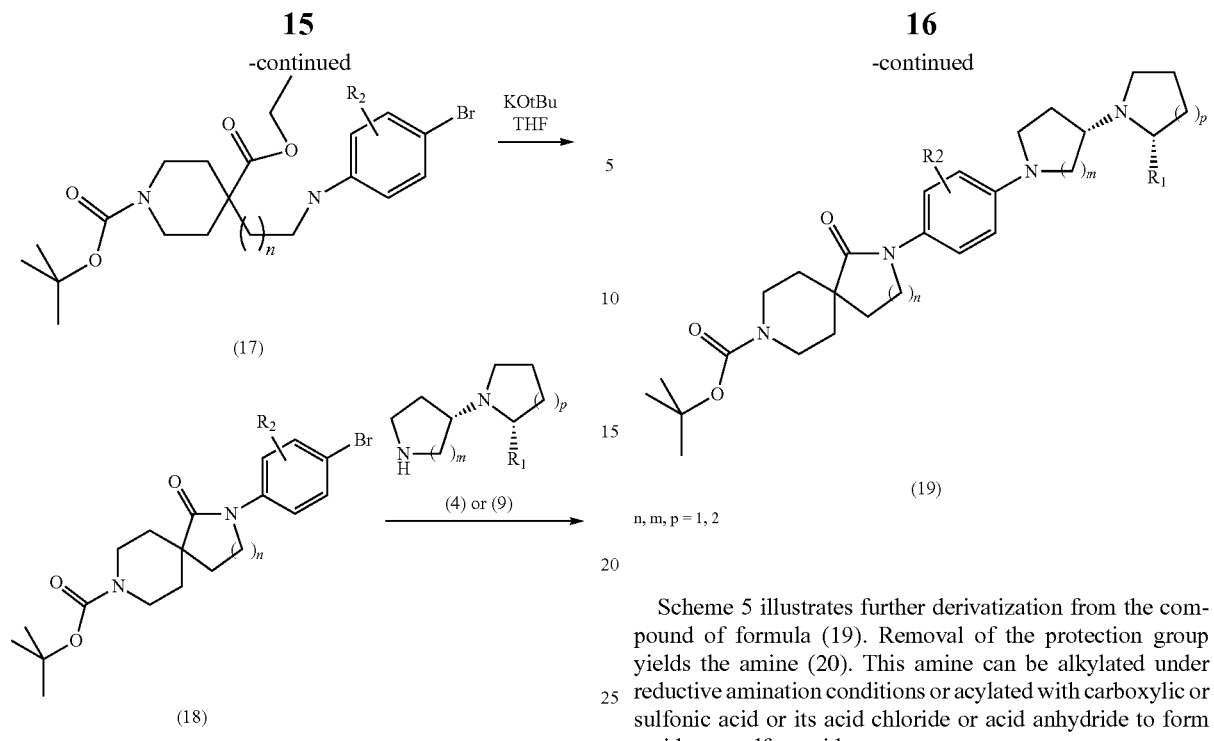
Scheme 5 illustrates further derivatization from the compound of formula (19). Removal of the protection group yields the amine (20). This amine can be alkylated under reductive amination conditions or acylated with carboxylic or sulfonic acid or its acid chloride or acid anhydride to form amides or sulfonamides.

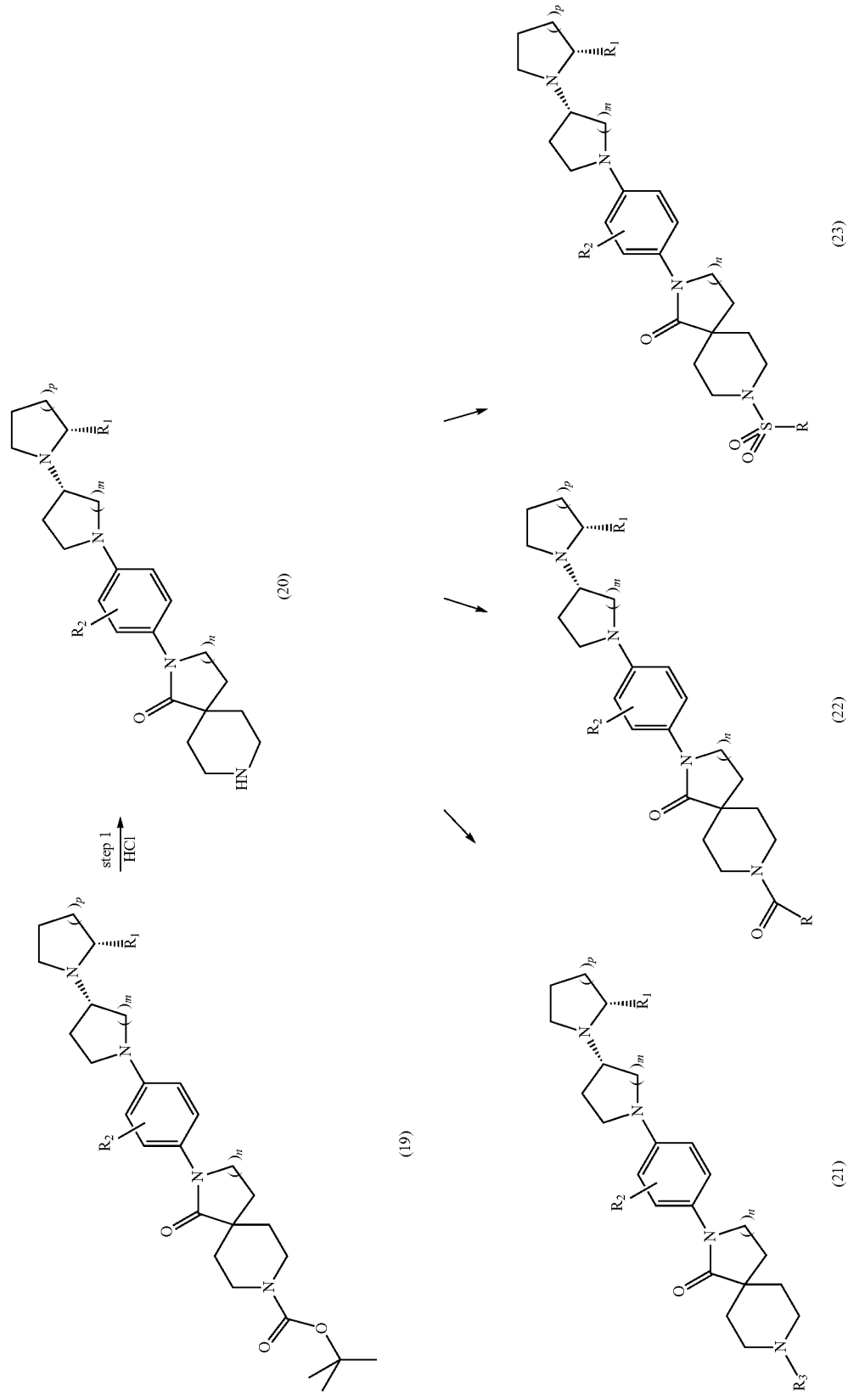

As already noted hereinabove, the compounds of this invention can readily be converted into salts. More particularly, the compounds of the present invention are basic, and as such compounds of this invention are useful in the form of the free base or in the form of a pharmaceutically acceptable acid addition salt thereof. Acid addition salts may be a more convenient form for use; and, in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compound is preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

In another aspect of this embodiment, a specific disease, a disorder or a condition that can be prevented and/or treated with the compound of this invention include, without any limitation the following: sleep-related disorders (specific examples include without any limitation narcolepsy, attentional deficits, circadian rhythm sleep disorders, obstructive sleep apnea, periodic limb movement and restless leg syndrome, excessive sleepiness and drowsiness due to medication side-effect, etc.), neurological disorders (specific examples that may be enumerated include but not limited to dementia, Alzheimer's disease, multiple sclerosis, epilepsy and neuropathic pain), neuropsychological and cognitive disorders (a few of the specific examples include without any limitation include schizophrenia, attention deficit/hyperactivity disorder, Alzheimer's disease, depression, seasonal affective disorder, and cognitive impairment). Certain of the disorders also include cognitive impairment associated with schizophrenia (CIAS), anxiety disorders such as generalized anxiety, panic disorder and post-traumatic stress disorder, and major depressive disorder. Other disorders include dementia of Alzheimer type (DAT), cognitive deficits related to neurological diseases such as Alzheimer, Parkinson, Huntington, age related cognitive impairment, mild cognitive impairment, vascular dementia, Lewis Body dementia and any other cognition associated to cognitive deficits.

As described hereinbelow by way of specific examples, the compounds of formula (I) bind to the H3 receptors and demonstrate inverse agonism versus H3 functional activity. Therefore, the compounds of this invention may have utility in the treatment of diseases or conditions ameliorated with H3 receptor ligands. More specifically, the compounds of the present invention are H3 receptor ligands that modulate function of the H3 receptor by antagonizing the activity of the receptor. Further, the compounds of this invention may be inverse agonists that inhibit the basal activity of the receptor or they may be antagonists that completely block the action of receptor-activating agonists. Additionally, the compounds of this invention may also be partial agonists that partially block or partially activate the H3 receptor or they may be agonists that activate the receptor. Thus the compounds of this invention may act differentially as antagonists, inverse agonists and/or partial agonists depending on functional output, histamine tone and or tissue context. Accordingly, the differential activities of these compounds may allow for utility to ameliorate multiple disease states as specifically enumerated above.

Thus in one aspect of this invention there is provided a method of treating a disease in a patient, said disease selected from the group consisting of sleep related disorder, dementia, Alzheimer's disease, multiple sclerosis, cognitive disorder, attention deficit hyperactivity disorder and depression, comprising administering to said patient a therapeutically effective amount of a compound of formula (I).

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of H3 receptors. That is, as noted above, the compounds of the present invention are modulators of H3 receptors and may be effectively administered to ameliorate any disease state which is mediated all or in part by H3 receptors.

All of the various embodiments of the compounds of this invention as disclosed herein can be used in the method of treating various disease states as described herein. As stated herein, the compounds used in the method of this invention are capable of inhibiting the effects of H3 receptor and thereby alleviating the effects and/or conditions caused due to the activity of H3.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

Finally, in yet another embodiment of this invention, there is also provided a pharmaceutical composition comprising a pharmaceutically acceptable carrier and a compound of formula (I), including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature H3 inhibitory activity and thus are useful in treating any disease, condition or a disorder caused due to the effects of H3 in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "L" refers to liters, "mL" or "ml" refers to milliliters, "µL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "DMSO" refers to dimethyl sulfoxide, "DMF" refers to N,N-dimethylformamide, "CDI" refers to 1,1'-carbonyldiimidazole, "DCM" or "$CH_2Cl_2$" refers to dichloromethane, "DCE" refers to 1,2-dichloroethane, "HCl" refers to hydrochloric acid, "EtOAc" refers to ethyl acetate, "PBS" refers to Phosphate Buffered Saline, "IBMX" refers to 3-isobutyl-1-methylxanthine, "PEG" refers to polyethylene glycol, "MeOH" refers to methanol, "$MeNH_2$" refers to methyl amine, "$N_2$" refers to nitrogen gas, "iPrOH" refers to isopropyl alcohol, "$Et_2O$" refers to ethyl ether, "LAH" refers to lithium aluminum hydride, "heptane" refers to n-heptane, "HMBA-AM" resin refers to 4-hydroxymethylbenzoic acid amino methyl resin, "$PdCl_2(dppf)_2$" refers to 1,1'-bis(diphenylphosphino)ferrocene-palladium (II) dichloride DCM complex, "HBTU" refers to 2-(1H-benzotriazol-1-yl)-1,1,3,3-tetramethyluronium hexafluorophosphate, "DIEA" refers to diisopropylethylamine, "CsF" refers to cesium fluoride, "MeI" refers to methyl iodide, "AcN," "MeCN" or "$CH_3CN$" refers to acetonitrile, "TFA" refers to trifluoroacetic acid, "THF" refers to tetrahydrofuran, "NMP" refers to 1-methyl-2-pyrrolidinone, "$H_2O$" refers to water, "BOC" refers to t-butyloxycarbonyl, "brine" refers to a saturated aqueous sodium chloride solution, "M" refers to molar, "mM" refers to millimolar, "µM" refers to micromolar, "nM" refers to nanomolar, "N" refers to normal, "TLC" refers to thin layer chromatography, "HPLC" refers to high performance liquid chromatography, "HRMS" refers to high resolution mass spectrum, "L.O.D." refers to loss on drying, "µCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets; br=broad; LC=liquid chromatograph; MS=mass spectrograph; ESI/MS=electrospray ionization/mass spectrograph; RT=retention time; M=molecular ion, "~"=approximately.

Reactions generally are run under a nitrogen atmosphere. Solvents are dried over magnesium sulfate and are evaporated under vacuum on a rotary evaporator. TLC analyses are performed with EM Science silica gel 60 F254 plates with visualization by UV irradiation. Flash chromatography is performed using Alltech prepacked silica gel cartridges. The $^1$H NMR spectra are run at 300 MHz on a Gemini 300 or Varian Mercury 300 spectrometer with an ASW 5 mm probe, and usually recorded at ambient temperature in a deuterated solvent, such as $D_2O$, DMSO-$D_6$ or $CDCl_3$ unless otherwise noted. Chemical shifts values ( ) are indicated in parts per million (ppm) with reference to tetramethylsilane (TMS) as the internal standard.

High Pressure Liquid Chromatography-Mass Spectrometry (LCMS) experiments to determine retention times ($R_T$) and associated mass ions are performed using one of the following methods:

Mass Spectra (MS) are recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., $N_2$ pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33×2 4 µM, 1 ml/min MUX: Column: YMC Jsphere 33×2, 1 ml/min Grad (AcN+0.05% TFA):(H2O+0.05% TFA)=5:95 (0 min) to 95:5 (3.4 min) to 95:5 (4.4 min).

LCT2: YMC Jsphere 33×2 4 µM, (AcN+0.05% TFA): (H2O+0.05% TFA)=5:95 (0 min) to 95:5 (3.4 min) to 95:5 (4.4 min)

QU: YMC Jsphere 33×2 1 ml/min, (AcN+0.08% formic acid):(H2O+0.1°)/0 formic acid)=5:95 (0 min) to 95:5 (2.5 min) to 95:5 (3.0 min)

The following examples describe the procedures used for the preparation of various starting materials employed in the preparation of the compounds of this invention.

INTERMEDIATES

Intermediate (i)

2-Methyl-[1,3']bipyrrolidinyl-1'-carboxylic acid tert-butyl ester

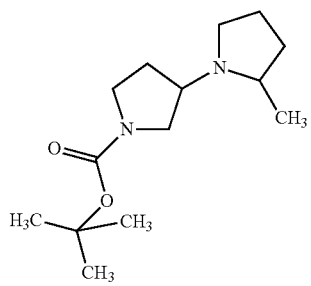 [SMILES: CC1CCCN1C1CCN(C(=O)OC(C)(C)C)C1]

To a solution of N—BOC-3-pyrrolidinone (4.22 g, 22.9 mmol) and 2-methylpyrroline (1.95 g, 22.9 mmol) (HCl salt was made by addition of 22.9 mL of 1 M HCl in ether into the DCM solution of 2-methylpyrroline, then evaporated) in DCE (60 mL) was added powdered sodium triacetoxyborohydride slowly under $N_2$ at r.t. The yellowish milky solution was stirred at r.t. overnight. LC/MS-m/z 255 and 199 (base and M-tBu).

The reaction was quenched with aq. $NaHCO_3$ solution (100 mL). The two layers were separated, and the aqueous layer was extracted with DCM (20 mL×2). The combined DCM extracts were washed with sodium bicarbonate (10 mL), and brine (5 mL×2), dried (anhydrous potassium carbonate), filtered, and concentrated in vacuo. The crude product was purified on a silica gel column, eluted with DCM and 7.5% MeOH in DCM to get 5.50 g (yield: 94%) of the title compound as a liquid. MS: 255 (M+H$^+$); TLC: 0.5 (10% MeOH in DCM).

Intermediate (ii)

2-Methyl-[1,3']bipyrrolidinyl hydrochloride

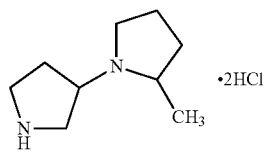

2-Methyl-[1,3']bipyrrolidinyl-1'-carboxylic acid tert-butyl ester (5.50 g, 21.62 mmol) was treated with 20 mL of 4 M HCl in dioxane at 0° C. The solution was stirred under nitrogen at r.t. overnight. TLC (10% MeOH in DCM) did not detect the starting material. $N_2$ was passed through the solution with stirring. The outlet was passed through KOH solution to absorb HCl for 30 min. The solvent was removed by evaporation to dryness to get the title compound as a hygroscopic gummy material, 5.3 g (~100%). This material was used without further purification in subsequent steps as illustrated below. LCMS: $R_T$=0.35 minutes, MS: 155 (M+H).

$^1$H NMR ($D_2O$, 300 MHz): 4.30 (m), 3.85 (m), 3.76 (s), 3.5 (m), 3.46 (m), 3.32 (m), 2.66 (m), 2.28 (m), 2.10 (m), 1.46 (bs).

Intermediate (iii)

(R)-3-(Toluene-4-sulfonyloxy)-pyrrolidine-1-carboxylic acid tert-butyl ester

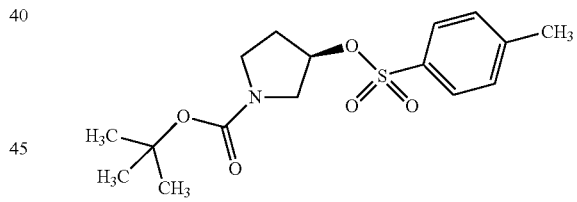

To a 2 L round-bottom flask equipped with a mechanical stirring rod and a 250 ml addition funnel was added p-tosyl chloride (58 g, 305 mmol, 1.5 eq) and 600 ml of anhydrous DCM. The solution was cooled with ice-water bath. $Et_3N$ (65 ml) and DMAP (2.65 g) were added. A solution of (R)-3-(−)-N-Boc-hydroxy pyrrolidine (38 g, 203 mmol, 1.0 eq) in 200 ml of DCM was added slowly. The reaction mixture was allowed to stir at room temperature over night. TLC showed completion of the reaction. The product had an $R_f$ value of 0.3 (TLC developed in DCM). The reaction was cooled by ice-water bath. Polymer-supported trisamine (32 g) was added and stirred for 30 min. Trisamine bead was filtered and rinsed with 300–400 mL of DCM. The organic solution was washed with 200 mL of $H_3PO_4$ (1M) solution twice, followed by saturated $NaHCO_3$ solution (200 mL), and brine (200 mL). The organic phase was dried over $K_2CO_3$. After concentration, the crude product was purified by a 750 g silica gel cartridge (DCM to 5% MeOH in DCM) to afford the title compound as a beige oil (52 g, 75%).

MS: 363 (M+Na⁺); TLC (DCM) R$_f$=0.3.

¹H NMR (CDCl₃, 300 MHz), δ (ppm): 7.80 (d, 9.0 Hz, 2H), 7.35 (d, 7.8 Hz, 2H), 5.04 (bs, 1H), 3.45 (m, 4H), 2.46 (bs, 3H), 2.05 (m, 2H), 1.43 (s, 9H).

Intermediate (iv)

(S)-3-(Toluene-4-sulfonyloxy)-pyrrolidine-1-carboxylic acid tert-butyl ester

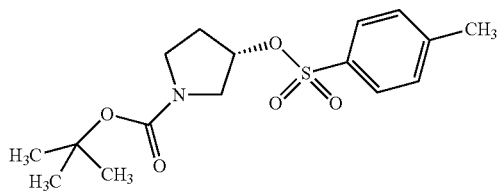 [SMILES: Cc1ccc(S(=O)(=O)O[C@H]2CCN(C(=O)OC(C)(C)C)C2)cc1]

A round bottomed flask was charged with 80 mL of anhydrous DCM. The solvent was evacuated and purged with nitrogen. To this solvent was added (3S)-1-BOC-3-pyrrolidinol (obtained from Astatech), (16.32 g, 33.8 mmol), DMAP (0.4 g). The solution was cooled to an ice-water bath. To this cold solution was added a solution of p-toluene-sulfonyl chloride (9.67 g, 50.87 mmol, 1.5 equiv.) in 20 mL of DCM. The ice-water bath was removed and the solution was stirred under nitrogen overnight. TLC (5% MeOH in DCM for SM, 12 visualization; DCM for product, UV) showed the completion of the reaction. The reaction was quenched by addition of polymer-supported amine (4.5 g), stirred 30 min. 50 mL of DCM was added and filtered. The filtration pad was washed with DCM. The organic was washed with H₃PO₄ (1M, 2×50 mL), followed by NaHCO₃ (50 mL, brine (50 mL), dried (K₂CO₃), filtered and concentrated to a liquid. This was purified on a 110 g silica gel column on Analogix using 0-2% MeOH in DCM to obtain pure product, 8.82 g (77% yield).

TLC (DCM) Rf=0.3. LC: Rt=3.55 min, 100% pure based on total ion, MS: 363 (M+Na); 342, 327, 286 (base).

¹H NMR (300 MHz, CDCl₃), δ (ppm): 7.81 (d, 8.7 Hz, 2H), 7.37 (d, 8.7 Hz, 2H), 5.04 (bs, 1H), 3.45 (m, 4H), 2.46 (s, 3H), 1.44 (s, 9H).

Intermediate (v)

(2S,3'S)-2-Methyl-[1,3']bipyrrolidinyl-1'-carboxylic acid tert-butyl ester

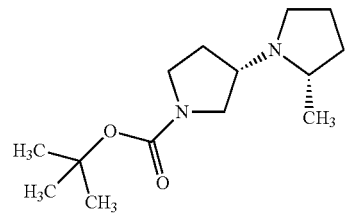 [SMILES: C[C@H]1CCCN1[C@H]1CCN(C(=O)OC(C)(C)C)C1]

The tosylate (52 g, 0.15 mol, 1.0 eq), (2S)-2-methylpyrrolidine (25.2 g, 0.3 mol, 2.0 eq), anhydrous CH₃CN (500 ml), and dry K₂CO₃ powder (50 g, 36 mmol, 2.4 eq) were added to a 2 L round-bottom flask equipped with a mechanical stirrer and a reflux condenser. The resulting suspension was stirred at 75° C. for 20 h. The heating block was set at 88° C.

LC/MS showed a trivial amount of starting material at m/z 363. The reaction mixture was concentrated in vacuo. The residue was partitioned between 200 mL of water and 400 mL of DCM. The aqueous layer was washed with 50 mL of DCM twice. The organic extracts were combined and washed with 150 mL of saturated NaHCO₃ solution, 150 mL of brine, and dried over K₂CO₃. The crude was purified by silica gel column, eluted with 5-10% MeOH in DCM. The product still had weak UV absorption at 254 nm and 280 nm. A pale yellow oil was obtained. Yield: 24.5 g (64%).

LCMS: R$_T$=1.27 minutes, MS: 255 (M+H).

¹H NMR (300 MHz, CDCl₃), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (vi)

(2R,3'S)-2-Methyl-[1,3']bipyrrolidinyl-1'-carboxylic acid tert-butyl ester

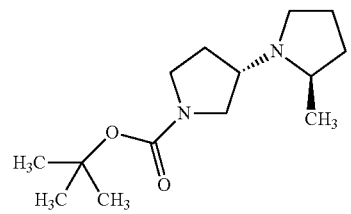 [SMILES: C[C@@H]1CCCN1[C@H]1CCN(C(=O)OC(C)(C)C)C1]

The title compound was prepared in a manner substantially the same as intermediate (2R,3'S)-2-Methyl-[1,3']bipyrrolidinyl-1'-carboxylic acid tert-butyl ester by condensing 3-(3R)-(toluene-4-sulfonyloxy)-pyrrolidine-1-carboxylic acid tert-butyl ester with R-(−)-2-methylpiperindine (obtained from Advanced Asymmetrics). LCMS: R$_T$=1.05 minutes, MS: 255 (M+H).

¹H NMR (300 MHz, CDCl₃), δ (ppm): 3.30 (m, 1H), 3.14 (bs, 2H), 2.91 (m, 1H), 2.75 (m, 1H), 2.51 (m, 1H), 2.07-1.69 (m, 6H), 1.46 (s, 9H), 1.10 (d, 6.0 Hz, 3H).

Intermediate (vii)

(2S,3'R)-2-Methyl-[1,3']bipyrrolidinyl-1'-carboxylic acid tert-butyl ester

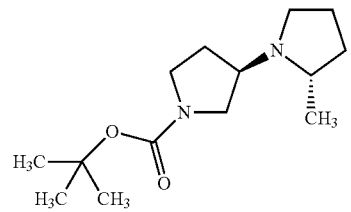

3-(3S)-(Toluene-4-sulfonyloxy)-pyrrolidine-1-carboxylic acid tert-butyl ester (6.82 g, 19.97 mmol, 1 equiv.) and S-(+)-2-methyl-piperidine (obtained from Advanced Asymmetrics), (3.40 g, 40 mmol, 2 equiv.) were dissolved in anhydrous CH₃CN (65 mL). To this colorless solution was added powder K₂CO₃ (powder, 325 mess, 98+%, 6.10 g, 44.2 mmol, 2.2 equiv.) at r.t. The suspension was heated with stirring under nitrogen over an oil bath maintained at 80° C. for 24 h. TLC (3% MeOH in DCM for SM, 7.5% MeOH in DCM for product) showed the SM was consumed almost completely. LC/MS showed very little amount of SM at m/z 363.

The suspension was concentrated to dryness. The residue was taken in water (25 mL) and DCM (80 mL). The two layers were separated, and the aqueous layer was extracted with DCM (20 mL×2). The combined DCM extracts were washed with sodium bicarbonate (25 mL), and brine (25 mL), dried (anhydrous potassium carbonate), filtered, and concentrated in vacuo. The crude product was purified on a silica gel column (70 g) on Analogix, eluted with MeOH in DCM (0 to 7.5%) to obtain 4.08 g (80.3%) of the title compound as a gummy material. LCMS: $R_T$=1.14 minutes, MS: 255 (M+H).

$^1$H NMR (300 MHz, CDCl$_3$), δ (ppm): 3.30 (m, 1H), 3.14 (bs, 2H), 2.91 (m, 1H), 2.75 (m, 1H), 2.51 (m, 1H), 2.07-1.69 (m, 6H), 1.46 (s, 9H), 1.10 (d, 6.0 Hz, 3H).

Intermediate (viii)

(2R,3'R)-2-Methyl-[1,3']bipyrrolidinyl-1'-carboxylic acid tert-butyl ester

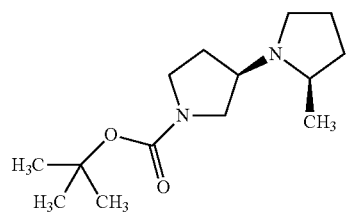 [SMILES: C[C@@H]1CCCN1[C@@H]1CCN(C(=O)OC(C)(C)C)C1]

The title compound was prepared in a manner substantially the same as intermediate (2R,3'S)-2-Methyl-[1,3']bipyrrolidinyl-1'-carboxylic acid tert-butyl ester by condensing 3-(3S)-(toluene-4-sulfonyloxy)-pyrrolidine-1-carboxylic acid tert-butyl ester and R-(−)-2-methylpiperindine (obtained from Advanced Asymmetrics). LCMS: $R_T$=1.09 minutes, MS: 255 (M+H).

$^1$H NMR (300 MHz, CDCl$_3$), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (ix)

(2S,3'R)-2-Methyl-[1,3']bipyrrolidinyl dihydrochloride

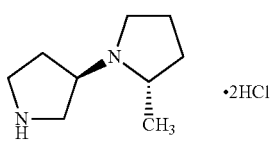

2(2S)-Methyl-[1,3'(3'R)]bipyrrolidinyl-1'-carboxylic acid tert-butyl ester (7.91 g, 31.14 mmol) was treated with 28.8 mL of HCl in dioxane at 0° C. The solution was stirred under nitrogen at r.t. overnight. Both TLC (10% MeOH in DCM) and LC/MS did not detect the starting material. The reaction was judged complete.

N$_2$ was passed through the solution with stirring. The outlet was passed through KOH solution to absorb HCl for 1 h. The solvent was removed by evaporation to dryness to get the title compound as a hygroscopic very thick gummy (2HCl salt, hydrated—Exact composition unknown), 8.07 g (~100%). MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (x)

(2S,3'S)-2-Methyl-[1,3']bipyrrolidinyl dihydrochloride

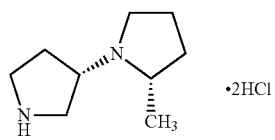

(2S,3'S)-2-Methyl-[1,3']bipyrrolidinyl-1'-carboxylic acid tert-butyl ester (24.5 g) was dissolved in 30 ml of dry 1,4-dioxane. HCl solution (85 ml, 4M in dioxane) was added at 0° C., and allowed to stir at room temperature. Brown gum appeared after about 20 minutes. After 4 h, the reaction was complete. N$_2$ was passed through the flask for 1 h with stirring. The outlet passed though KOH solution to absorb HCl. The solvent was removed by vacuum to afford 29 g of hygroscopic beige gum.

LCMS: $R_T$=0.37 minutes, MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xi)

(2R,3'S)-2-Methyl-[1,3']bipyrrolidinyl dihydrochloride

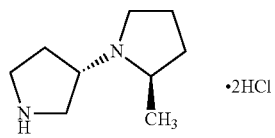

The title compound was prepared in a manner substantially the same as intermediate (2S,3'R)-2-Methyl-[1,3']bipyrrolidinyl dihydrochloride by acid hydrolysis of 2(2R)-methyl-[1,3'(3'S)]bipyrrolidinyl-1'-carboxylic acid tert-butyl ester.

MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xii)

(2R,3'R)-2-Methyl-[1,3']bipyrrolidinyl dihydrochloride

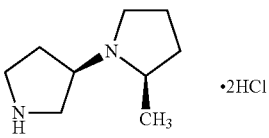

The title compound was prepared in a manner substantially the same as intermediate (2S,3'R)-2-Methyl-[1,3']bipyrrolidinyl dihydrochloride by acid hydrolysis of 2-(2R)-methyl-[1,3'(3'R)]bipyrrolidinyl-1'-carboxylic acid tert-butyl ester.

MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xiii)

4-Allyl-piperidine-1,4-dicarboxylic acid 1-tert-butyl ester 4-ethyl ester

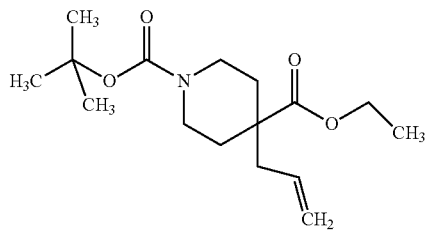 [SMILES: C=CCC1(C(=O)OCC)CCN(C(=O)OC(C)(C)C)CC1]

In a 250-mL RBF was weighed 6.1 g (60 mmol) of diisopropylamine and dissolved in THF. This solution was cooled to −78° C. To this was added 24 mL of 2.5 M (60 mmol) of butyllithium in hexane and stirred for 15 min, warmed up to 0° C. for 20 min, re-cooled to −78° C. To this was added piperidine-1,4-dicarboxylic acid 1-tert-butyl ester 4-ethyl ester (12.87 g, 50 mmol) in THF (10 mL). There was almost no color change. This was stirred at −78° C. for 45 min. Then, a mixture of 5 g of HMPA and 10.92 g of allyl iodide was added via cannula. The solution was still clear, very light in yellow. This mixture was stirred at −78° C. for 20 min, then, the dry ice bath was removed and the stirring was continued to allow the reaction mixture warm to r.t. over 40 min. The reaction mixture was poured into ice (~50 g), sat'd NH$_4$Cl aq. (50 mL) and ether (50 mL). The two layers were separated, the aqueous layer was extracted with ether (3×50 mL). The combined organic layers were washed with brine, dried (K$_2$CO$_3$), filtered, and concentrated in vacuo to obtain 15 g (100%) of the title compound as a yellow liquid, LC R$_T$=3.45 min, MS: 198, 242 (M-tBu).

NMR (300 MHz, CDCl3) δ: NMR (300 MHz, CDCl3): 5.68 (m, 1H); 5.07 (, bs, 1H), 5.04 (d, 10.2 Hz, 1H), 4.17 (q, 7.2, 2H), 3.88 (broad d, 9 Hz, 2H), 2.9 (broad t, 12.9 Hz, 2H), 2.27 (d, 7.8 Hz, 2H), 2.1 (broad d, 13.2 Hz), 1.45 (s, 9H), 1.26 (t, 7.2 Hz, 3H).

Intermediate (xiv)

4-(2-Oxo-ethyl)-piperidine-1,4-dicarboxylic acid 1-tert-butyl ester 4-ethyl ester

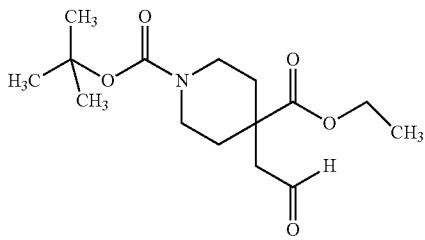 [SMILES: CCOC(=O)C1(CC=O)CCN(C(=O)OC(C)(C)C)CC1]

4-Allyl-piperidine-1,4-dicarboxylic acid 1-tert-butyl ester 4-ethyl ester (2.97 g, 10 mmol) was dissolved in iPrOH (50.0 mL) and H$_2$O (10.0 mL). To this was added a aqueous solution of NaIO$_4$ (4.68 g, 21.8 mmol) in water (40.0 mL), followed by addition of OsO$_4$ (8.4 mg, crystals, in one portion) at rt. The solution was stirred at rt. After 30 min, milky cloudy formed. Stirring was continued overnight. TLC and LC/MS did not detect the SM, but it is still very milky. The reaction mixture was poured into ice water (20 mL) and EtOAc (30 mL). The two layers were separated and the aqueous layer was extracted with EtOAc (3×15 mL). The combined extracts were washed with brine, and concentrated to dryness to get a liquid. The liquid was subject a reduced distillation to remove isopropanol. The remaining liquid was purified on a 50-g silica gel column, eluted with MeOH in DCM (0-5%). Note: the product is not UV active. Anisaldehyde visualization was used. The product fractions were collected and concentrated to yield 1.03 g (34% yield) of the title compound as a liquid.

LC/MS: R$_T$=2.84 min, MS: 300.

NMR (300 MHz, CDCl3) δ: 9.73 (t, 1.8 Hz, 1H), 4.22 (q, 7.2 Hz, 2H), 3.69 (m, 2H), 3.20 (m, 2H), 2.68 (m, 2H), 2.12 (m, 2H), 1.52 (m, 2H), 1.49 (s, 9H), 1.27 (t, 7.2 Hz, 3H).

Intermediate (xv)

4-[2-(4-Bromo-2-methyl-phenylamino)-ethyl]-piperidine-1,4-dicarboxylic acid 1-tert-butyl ester 4-ethyl ester

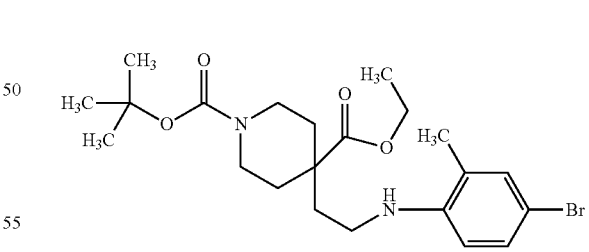

2-Methyl-4-bromo-aniline (0.637 g, 3.427 mmol) was dissolved in DCE (15 mL); to this solution was transferred a solution of 4-(2-oxo-ethyl)-piperidine-1,4-dicarboxylic acid 1-tert-butyl ester 4-ethyl ester (1.03 g, 3.425 mmol) in DCE (35 mL). The flask was submerged in a water bath at rt. To this clear solution was then added acetic acid (0.647 g, 10.8 mmol, 3.1 equiv), followed by addition of powder NaBH(OAc)$_3$ (2.18 g, 10.3 mmol, 3 equiv.) under N$_2$ at r.t. The yellowish milky suspension was stirred at r.t. overnight. LC/MS showed m/z 469/471 at t=4.930 min. along with small amount of aniline sm at 2.103 (186/188). TLC (5% of MeOH in DCM) showed no SM. of aldehyde, but aniline. The reaction was diluted with DCM (20 mL), cooled to ice-water bath, and quenched with 10 mL of 1N NH₄OH. The two layers were separated, and the aqueous layer was extracted with DCM (15 mL×3). The combined DCM extracts were washed with sodium bicarbonate (10 mL), and brine (10 mL), dried (anhydrous potassium carbonate), filtered, and concentrated. The product was purified on a 40 g-silica gel column eluted with 0-2% of MeOH in DCM to get 0.65 g (41%) of the title compound as an oil.

LC/MS $R_T$=3.96 min, MS: 469/471 (M+H⁺)

NMR (300 MHz, CDCl3) δ: 7.21-7.13 (m, 2H), 6.42 (d, 8.4 Hz, 1H), 4.15 (q, 7.2 Hz, 2H), 3.88 (m, 3H), 3.13 (m, 2H), 2.93 (m, 2H), 2.16 (bd, 2H), 2.26 (s, 3H), 1.88 (m, 2H), 1.46 (s, 9H), 1.43 (m, 2H), 1.42 (t, 7.2 Hz, 3H).

Intermediate (xvi)

4-[2-(4-Bromo-phenylamino)-ethyl]-piperidine-1,4-dicarboxylic acid 1-tert-butyl ester 4-ethyl ester

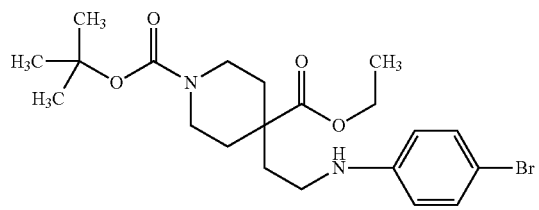 [SMILES: CCOC(=O)C1(CCNc2ccc(Br)cc2)CCN(C(=O)OC(C)(C)C)CC1]

This intermediate was synthesized in substantially the same way as described above from 1.75 g of the desired aldehyde to get 1.45 g (54% yield) of the title product as a colorless liquid.

LC/MS: $R_T$=3.81 mins; MS: 455/457

Intermediate (xvii)

4-[2-(4-Bromo-2-trifluoromethyl-phenylamino)-ethyl]-piperidine-1,4-dicarboxylic acid 1-tert-butyl ester 4-ethyl ester

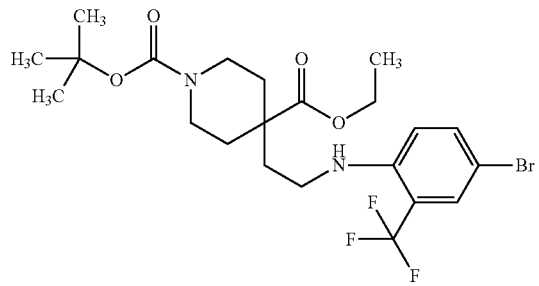 [SMILES: CCOC(=O)C1(CCNc2ccc(Br)cc2C(F)(F)F)CCN(C(=O)OC(C)(C)C)CC1]

This intermediate was synthesized in substantially the same way as described above from 1.75 g of the desired aldehyde to get 2.03 g (66% yield) of the title product as a yellow liquid.

LC/MS: $R_T$=4.18 mins; MS: 523/525.

Intermediate (xviii)

4-[2-(4-Bromo-2-fluoro-phenylamino)-ethyl]-piperidine-1,4-dicarboxylic acid 1-tert-butyl ester 4-ethyl ester

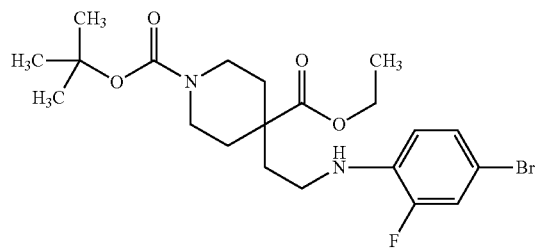 [SMILES: CCOC(=O)C1(CCNc2ccc(Br)cc2F)CCN(C(=O)OC(C)(C)C)CC1]

This intermediate was synthesized in substantially the same way as described above from 1.75 g of the desired aldehyde to get 1.97 g (71% yield) of the title product as an amber liquid.

LC/MS: $R_T$=3.95 mins; MS: 473/475.

Intermediate (xix)

2-(4-Bromo-2-methyl-phenyl)-1-oxo-2,8-diaza-spiro[4.5]decane-8-carboxylic acid tert-butyl ester

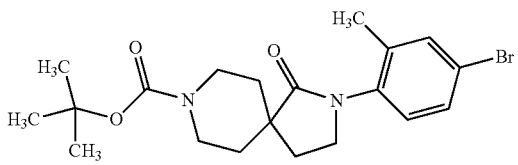 [SMILES: Cc1cc(Br)ccc1N1CCC2(CCN(C(=O)OC(C)(C)C)CC2)C1=O]

To a clear solution of 4-[2-(4-Bromo-2-methyl-phenylamino)-ethyl]-piperidine-1,4-dicarboxylic acid 1-tert-butyl ester 4-ethyl ester (3.42 mmol) in THF (40 mL) was added a solution of potassium t-butoxide (1M in THF) 1 mL (1 mmol, 0.3 equiv.) at r.t. (water bath at rt). The clear solution turned a little bit cloudy. After 30 min, TLC (5% MeOH in DCM) showed the reaction is complete (spot to spot), LC/MS detected the product peak of 423/425 (t 3.267 min). The reaction was cooled in an ice-water bath, diluted with 100 mL of DCM, quenched with 20 mL of water. The two layers were separated. The aqueous layer was extracted with DCM (2×20 mL). The combined DCM extracts were washed with brine, and concentrated on rotavap to yield 0.90 g (63% yield) of the title compound as a white solid.

LC $R_T$=4.00 min, MS: 423/425;

NMR (300 MHz, CDCl3) δ: 7.42 (m, 1H), 7.35 (m, 1H), 7.00 (d, 8.4 Hz, 1H), 4.03 (m, 2H), 3.64 (t, 6.9 Hz, 2H), 3.06 (m, 2H), 2.17 (s, 3H), 2.13 (m, 2H), 1.96 (m, 2H), 1.57 (m, 2H), 1.47 (s, 9H).

Intermediate (xx)

2-(4-Bromo-phenyl)-1-oxo-2,8-diaza-spiro[4.5]decane-8-carboxylic acid tert-butyl ester

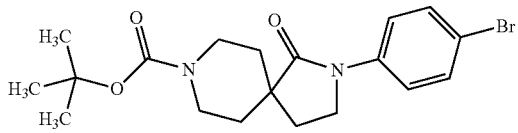 [SMILES: CC(C)(C)OC(=O)N1CCC2(CC1)CCN(c1ccc(Br)cc1)C2=O]

This intermediate is synthesized in the same way as described above from 1.44 g of the desired aniline to get 0.955 g (74% yield) of the title product as a beige solid.
LC/MS: 4.13 mins./409.09

Intermediate (xxi)

2-(4-Bromo-2-trifluoromethyl-phenyl)-1-oxo-2,8-diaza-spiro[4.5]decane-8-carboxylic acid tert-butyl ester

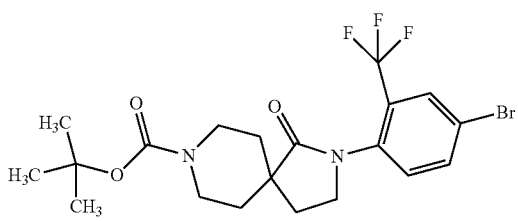 [SMILES: CC(C)(C)OC(=O)N1CCC2(CC1)CCN(c1ccc(Br)cc1C(F)(F)F)C2=O]

This intermediate is synthesized in the same way as described above from 2.04 g of the desired aniline to get 1.79 g (97% yield) of the title product as a yellow solid.
LC/MS: $R_T$=4.13 mins./MS: 477

Intermediate (xxii)

2-(4-Bromo-2-fluoro-phenyl)-1-oxo-2,8-diaza-spiro[4.5]decane-8-carboxylic acid tert-butyl ester

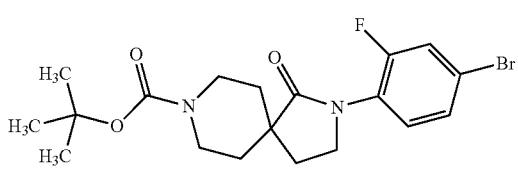 [SMILES: CC(C)(C)OC(=O)N1CCC2(CC1)CCN(c1ccc(Br)cc1F)C2=O]

This intermediate is synthesized in the same way as described above from 1.98 g of the desired aniline to get 1.75 g (98% yield) of the title product as a brown solid.
LC/MS: $R_T$=3.98 mins. MS: 427

Intermediate (xxiii)

4-But-3-enyl-piperidine-1,4-dicarboxylic acid 1-tert-butyl ester 4-ethyl ester

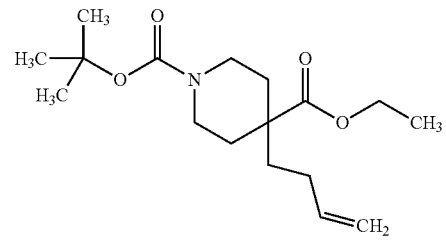 [SMILES: C=CCCC1(C(=O)OCC)CCN(C(=O)OC(C)(C)C)CC1]

A mixture of THF (160 mL) and diisopropyl amine (9.92 mL, 70.8 mmol, 1.2 eq) was cooled to −78° C. and a 2.5 M solution of n-BuLi in heptanes (28.3 mL, 70.8 mmol, 1.2 eq) was added slowly. The solution was stirred for 15 min, warmed to 0° C. for 20 min and cooled back to −78° C. Ethyl N-Bocpiperidine-4-carboxylate (11 mL, 59 mmol, 1 eq.) in 10 mL of THF was added drop-wise and stirred for 40 min before it was warmed to rt. The reaction mixture was stirred for 12 h, transferred to a separatory funnel, quenched with 500 mL of water and extracted with ethyl acetate (2×300 mL). The combined organics were dried over Na2SO4 and concentrated under vacuum to give the title compound as a yellow oil (13.9 g, 76%).
LC/MS: $R_T$=4.15 mins. MS: 312
NMR (300 MHz, CDCl3) δ: 5.75 (ddt, 1H), 5.02 (d, 1H), 4.96 (t, 1H), 4.18 (q, 2H), 3.89-3.86 (m, 2H), 2.88 (t, 2H), 2.11 (d, 2H), 1.99-1.93 (m, 2H), 1.66-1.57 (m, 2H), 1.45 (s, 9H), 1.43-1.32 (m, 2H), 1.27 (t, 3H).

Intermediate (xxiv)

4-(3-Oxo-propyl)-piperidine-1,4-dicarboxylic acid 1-tert-butyl ester 4-ethyl ester

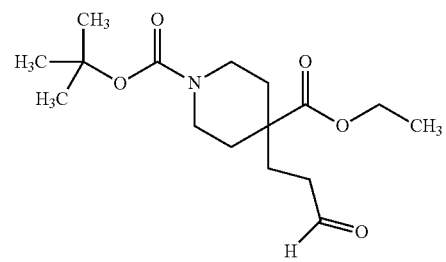 [SMILES: CCOC(=O)C1(CCC=O)CCN(C(=O)OC(C)(C)C)CC1]

4-But-3-enyl-piperidine-1,4-dicarboxylic acid 1-tert-butyl ester 4-ethyl ester (13.5 g, 43.48 mmol, 1 eq) was dissolved in i-PrOH (217 mL) and a solution of NaIO4 (20.23 g, 94.6 mmol, 2.18 eq) in 217 mL of water was added followed by OsO4 (37 mg, 0.144 mmol, 0.003 eq). The reaction mixture was vigorously stirred for 6 h. The reaction mixture was then quenched with 1500 mL of water, transferred to a separatory funnel and extracted with ethyl acetate (3×200 mL). The combined organics were dried over Na2SO4 and purified by column chromatography on silica gel (300 g column, 30% EtOAc in heptanes; 50 mL/min). This gave 8.5 g (63%) of the title compound as a beige oil.
LC $R_T$=3.62 min, MS: 314;

NMR (300 MHz, CDCl3) δ: 9.75 (s, 1H), 4.17 (q, 2H), 4.16-4.14 (m, 2H), 2.87 (t, 2H), 2.43 (dt, 2H), 2.10 (d, 2H), 1.85 (t, 2H), 1.45 (s, 9H), 1.36 (dd, 2H), 1.27 (t, 3H).

Intermediate (xxv)

4-[3-(4-Bromo-2-methyl-phenylamino)-propyl]-piperidine-1,4-dicarboxylic acid 1-tert-butyl ester 4-ethyl ester

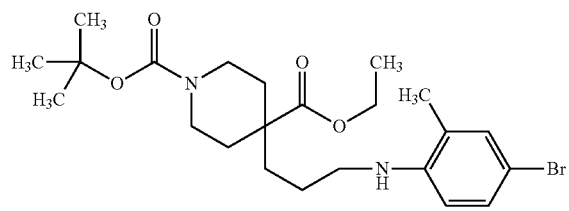 [SMILES: CCOC(=O)C1(CCCNc2ccc(Br)cc2C)CCN(C(=O)OC(C)(C)C)CC1]

2-Methyl-4-bromo-aniline (1.68 g, 9.05 mmol, 1 eq) was dissolved in 1,2-dichloroethane (95 mL). A solution of 4-(3-Oxo-propyl)-piperidine-1,4-dicarboxylic acid 1-tert-butyl ester 4-ethyl ester (2.8 g, 9.05 mmol, 1 eq) in 95 mL of 1,2-dichloroethane was added to the previous solution followed by glacial acetic anhydride (1.74 g, 28.05 mol, 3.1 eq) and NaBH(OAc)$_3$ (5.76 g, 27.15 mmol, 3 eq). The reaction mixture was stirred for 48 h, quenched with 200 mL of water, transferred to a separatory funnel and extracted with dichloromethane (2×100 mL). The combined organics were dried over Na2SO4 and purified by column chromatography on silica gel (200 g column, 25% EtOAc in heptanes; 50 mL/min). This gave 3.78 g (86%) of the title compound as a beige gum.

LC $R_T$=4.82 min, MS: 383;

NMR (300 MHz, CDCl3) δ: 7.16 (dd, 1H), 7.15 (s, 1H), 6.40 (d, 1H), 4.16 (q, 2H), 3.87 (d, 2H), 3.41 (s, 1H), 3.09-3.09 (m, 2H), 2.89 (t, 2H), 2.13 (s, 1H), 2.09 (s, 3H), 1.66-1.52 (m, 3H), 1.45 (s, 9H), 1.26 (d, 3H), 1.27-1.17 (m, 2H), 0.88 (t, 3H).

Intermediate (xxvi)

4-[3-(4-Bromo-phenylamino)-propyl]-piperidine-1,4-dicarboxylic acid 1-tert-butyl ester 4-ethyl ester

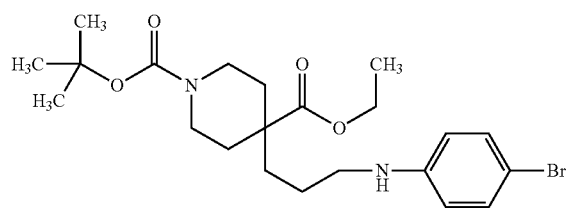 [SMILES: CCOC(=O)C1(CCCNc2ccc(Br)cc2)CCN(C(=O)OC(C)(C)C)CC1]

This intermediate was synthesized in substantially the same way as above.

LC $R_T$=4.65 min, MS: 469 (M+H);

NMR (300 MHz, CDCl3) δ: 7.23 (d, 2H), 6.44 (d, 2H), 4.16 (q, 2H), 3.87 (d, 2H), 3.61 (s, 1H), 3.04 (t, 2H0, 2.88 (t, 2H), 2.10 (d, 2H), 1.63-1.48 (m, 3H), 1.45 (s, 9H), 1.26 (d, 3H), 0.88 (t, 3H).

Intermediate (xxvii)

4-[3-(4-Bromo-2-fluoro-phenylamino)-propyl]-piperidine-1,4-dicarboxylic acid 1-tert-butyl ester 4-ethyl ester

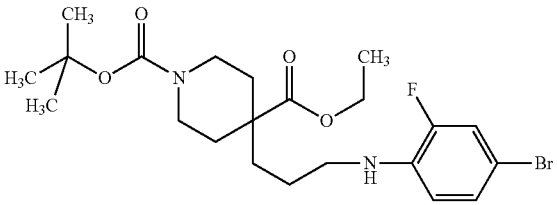 [SMILES: CCOC(=O)C1(CCCNc2ccc(Br)cc2F)CCN(C(=O)OC(C)(C)C)CC1]

This intermediate was synthesized in substantially the same way as above.

LC $R_T$=4.82 min, MS: 487 (M+H);

NMR (300 MHz, CDCl3) δ: 7.16-7.03 (m, 2H), 6.65 (t, 1H), 4.16 (q, 2H), 3.84-3.72 (m, 2H), 3.08 (q, 2H), 2.88 (t, 2H), 2.10 (d, 2H), 1.66-1.52 (m, 3H), 1.45 (s, 9H), 1.40-1.34 (m, 1H), 1.26 (d, 3H), 0.88 (t, 3H).

Intermediate (xxviii)

2-(4-Bromo-2-methyl-phenyl)-1-oxo-2,9-diaza-spiro[5.5]undecane-9-carboxylic acid tert-butyl ester

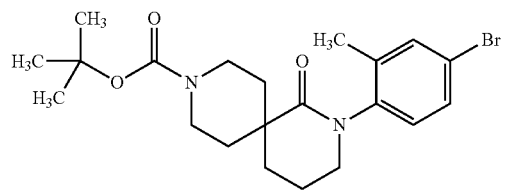 [SMILES: Cc1cc(Br)ccc1N1CCCC2(CCN(C(=O)OC(C)(C)C)CC2)C1=O]

4-[3-(4-Bromo-2-methyl-phenylamino)-propyl]-piperidine-1,4-dicarboxylic acid 1-tert-butyl ester 4-ethyl ester (3.78 g, 7.81 mmol, 1 eq) was dissolved in THF (80 mL). A 1M solution of NaOt-Bu in THF (7.8 mL, 7.8 mmol, 1 eq) was added and the reaction mixture was stirred for 2 h at rt. The reaction mixture was stirred for 48 h, quenched with 250 mL of water, transferred to a separatory funnel and extracted with dichloromethane (2×150 mL). The combined organics were dried over Na$_2$SO$_4$ and purified by column chromatography on silica gel (200 g column, 50% EtOAc in heptanes; 50 mL/min). This gave 2.49 g (73%) of the title compound as a beige gum.

LC $R_T$=4.08 min, MS: 437 (M+H);

NMR (300 MHz, CDCl3) δ: 7.40 (s, 1H), 7.35 (dd, 1H), 6.96 (d, 1H), 3.85-3.71 (m, 2H), 3.60-3.54 (m, 1H), 3.39-3.22 (m, 3H), 2.21-2.04 (m, 3H), 2.12 (s, 3H), 1.97-1.88 (m, 3H), 1.45 (s, 9H), 1.31-1.24 (m, 2H).

Intermediate (xxix)

2-(4-Bromo-phenyl)-1-oxo-2,9-diaza-spiro[5.5]undecane-9-carboxylic acid tert-butyl ester

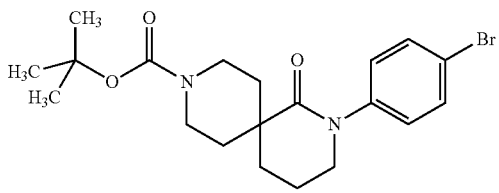 [SMILES: CC(C)(C)OC(=O)N1CCC2(CCCN(c3ccc(Br)cc3)C2=O)CC1]

This intermediate was synthesized in substantially the same way as above.
LC $R_T$=3.97 min, MS: 423 (M+H);
NMR (300 MHz, CDCl3) δ: 7.49 (d, 2H), 7.09 (d, 2H), 3.83-3.75 (m, 2H), 3.64-3.60 (m, 2H), 3.31-3.22 (m, 2H), 2.18-2.04 (m, 2H), 1.98-1.90 (m, 4H), 1.46 (s, 9H), 1.31-1.24 (m, 2H).

Intermediate (xxx)

2-(4-Bromo-2-fluoro-phenyl)-1-oxo-2,9-diaza-spiro[5.5]undecane-9-carboxylic acid tert-butyl ester

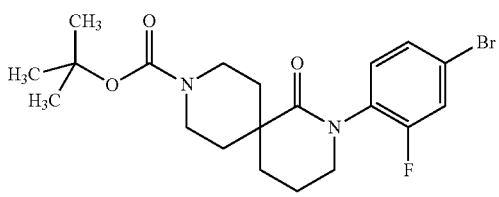 [SMILES: CC(C)(C)OC(=O)N1CCC2(CCCN(c3ccc(Br)cc3F)C2=O)CC1]

This intermediate was synthesized in substantially the same way as above.
LC $R_T$=4.05 min, MS: 441 (M+H);
NMR (300 MHz, CDCl3) δ: 7.33-7.28 (m, 2H), 7.09 (t, 1H), 3.80-3.72 (m, 2H), 3.59-3.55 (m, 2H), 3.36-3.27 (m, 2H), 2.16-2.04 (m, 2H), 1.99-1.90 (m, 4H), 1.46 (s, 9H), 1.31-1.24 (m, 2H).

Example 1

2-[2-Methyl-4-((2R,3'S)-2-methyl-[1,3']bipyrrolidinyl-1'-yl)-phenyl]-1-oxo-2,8-diaza-spiro[4.5]decane-8-carboxylic acid tert-butyl ester

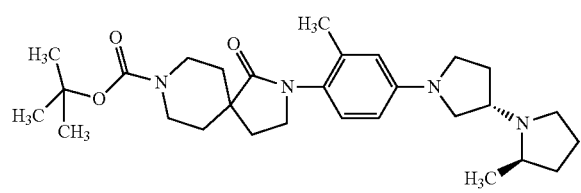 [SMILES: Cc1cc(N2CC[C@H](N3CCC[C@H]3C)C2)ccc1N1CCC2(CCN(C(=O)OC(C)(C)C)CC2)C1=O]

The HCl salt of (2R,3'S)-2-Methyl-[1,3']bipyrrolidinyl was dissolved in 2 mL of MeOH with the aid of sonication. To the solution was added 50 mL of DCM. The solution was cooled to an ice-water bath. To this solution was added powder KOH (0.5 g, 9.5 mmol, 2.6 equiv. to the amine salt) with stirring under N2. The stirring was continued for 1 h. 0.5 g of powder $K_2CO_3$ was added with stirring to form a nice suspension. The suspension was filtered through a Celite pad, rinsed with DCM until no amine was leach out by TLC (20% MeOH in DCM, anisaldehyde visualization, white spot just above the origin). The solution was concentrated to dryness; the residue was further dried under high vacuum with stirring for 1 h, re-dissolved in anhydrous toluene and ready to use.

An 20-mL vial containing a stir bar was charged with $Pd_2(dba)_3$ (0.01 equiv., 0.002036 mmol, 2 mg.), 2-dicyclohexylphosphino-2',4',6'-triisopropyl-biphenyl (0.05 equiv., 0.01018 mmol, 5 mg.), and sodium t-butoxide (2.5 equiv., 0.509 mmol, 50 mg.). The vial was de-gassed and refilled with $N_2$ three cycles. A solution of 2-(4-bromo-2-methyl-phenyl)-1-oxo-2,8-diaza-spiro[4.5]decane-8-carboxylic acid tert-butyl ester (86 mg, 0.2 mmol; prepared from 0.82 g dissolved in 9.5 mL of toluene, 1 mL was used for each reaction) was introduced and the red solution was stirred for 1 min at rt, then the amine in toluene (1.11 equiv., 1 mL each, corresponding to 60 mg, 0.22 mmol of bipyrrolidine) was introduced. The flask was evacuated and backfilled with N2. The reaction was heated in an oil bath set at 90° C. for 2.5 h, allowed to cool down to room temperature. Toluene was evaporated under reduced pressure. The residue was re-dissolved in DCM (10 mL) and aq. $NaHCO_3$ (2 mL). The two layers were separated and the aqueous layer was extracted with DCM (3×5 mL). The combined DCM extracts were washed with sodium bicarbonate (5 mL), and brine (5 mL), dried (anhydrous potassium carbonate), filtered, and concentrated. The crude product was purified on a 10-g silica gel column eluted with DCM and 5% of 7N NH3 MeOH in DCM to obtain the title compound as a semi-solid.
LC, $R_T$=2.63 mins; MS: 497.
$^1$H NMR (CDCl$_3$, 300 MHz), δ (ppm): 6.96 (m, 1H), 6.39 (m, 2H), 4.04 (m, 2H), 3.59 (t, 6.6 Hz, 2H), 3.45-3.17 (m, 5H), 3.02 (m, 3H), 2.79 (m, 1H), 2.54 (q, 6.0 Hz, 1H), 2.30-1.90 (m, 9H), 1.76 (m, 3H), 1.62-1.39 (m, 12H), 1.14 (d, 6.3 Hz, 3H).

Example 2

2-[2-Methyl-4-((2R,3'R)-2-methyl-[1,3']bipyrrolidinyl-1'-yl)-phenyl]-1-oxo-2,8-diaza-spiro[4.5]decane-8-carboxylic acid tert-butyl ester

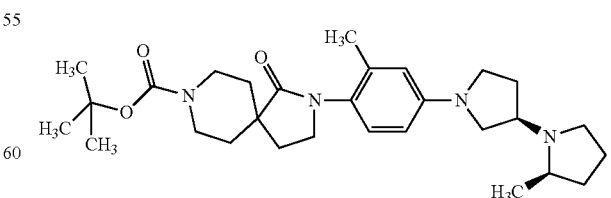

The title compound was prepared in a manner substantially the same as Example 1 to obtain the title compound as a semi-solid.
LC, $R_T$=2.66 mins; MS: 497.

¹H NMR (CDCl₃, 300 MHz), δ (ppm): 6.96 (m, 1H), 6.39 (m, 2H), 4.04 (m, 2H), 3.59 (t, 6.6 Hz, 2H), 3.50 (t, 7.2 Hz, 1H), 3.37 (dt, 2.2 Hz, 9.3 Hz, 1H), 3.245 (m, 3H), 3.04 (m, 3H), 2.77 (m, 1H), 2.54 (q, 6.0 Hz, 1H), 2.17-1.90 (m, 9H), 1.76 (m, 3H), 1.62-1.39 (m, 12H), 1.14 (d, 6.3 Hz, 3H).

Example 3

2-[2-Methyl-4-((2S,3'R)-2-methyl-[1,3']bipyrrolidinyl-1'-yl)-phenyl]-1-oxo-2,8-diaza-spiro[4.5]decane-8-carboxylic acid tert-butyl ester

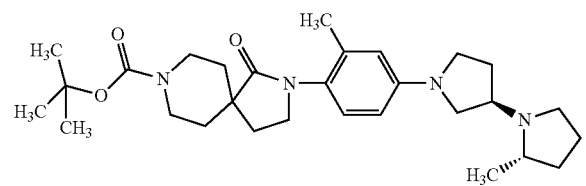 [SMILES: Cc1cc(N2CC[C@@H](N3CCC[C@@H]3C)C2)ccc1N1CCC2(CCN(C(=O)OC(C)(C)C)CC2)C1=O]

The title compound was prepared in a manner substantially the same as Example 1 to obtain the title compound as a semi-solid.

LC, R_T=2.56 mins; MS: 497.

¹H NMR (CDCl₃, 300 MHz), δ (ppm): 6.96 (m, 1H), 6.39 (m, 2H), 4.04 (m, 2H), 3.59 (t, 6.6 Hz, 2H), 3.45-3.17 (m, 5H), 3.02 (m, 3H), 2.79 (m, 1H), 2.54 (q, 6.0 Hz, 1H), 2.30-1.90 (m, 9H), 1.76 (m, 3H), 1.62-1.39 (m, 12H), 1.14 (d, 6.3 Hz, 3H).

Example 4

2-[2-Methyl-4-((2S,3'S)-2-methyl-[1,3']bipyrrolidinyl-1'-yl)-phenyl]-1-oxo-2,8-diaza-spiro[4.5]decane-8-carboxylic acid tert-butyl ester

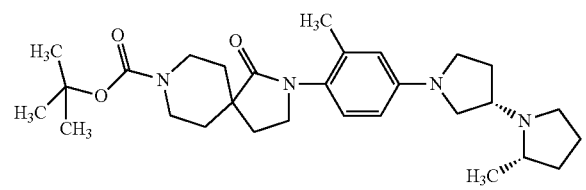 [SMILES: Cc1cc(N2CC[C@H](N3CCC[C@@H]3C)C2)ccc1N1CCC2(CCN(C(=O)OC(C)(C)C)CC2)C1=O]

The title compound was prepared in a manner substantially the same as Example 1 to obtain the title compound as a semi-solid.

LC, R_T=2.61 mins; MS: 497.

¹H NMR (CDCl₃, 300 MHz), δ (ppm): 6.96 (m, 1H), 6.39 (m, 2H), 4.04 (m, 2H), 3.59 (t, 6.6 Hz, 2H), 3.50 (t, 7.2 Hz, 1H), 3.37 (dt, 2.2 Hz, 9.3 Hz, 1H), 3.245 (m, 3H), 3.04 (m, 3H), 2.77 (m, 1H), 2.54 (q, 6.0 Hz, 1H), 2.17-1.90 (m, 9H), 1.76 (m, 3H), 1.62-1.39 (m, 12H), 1.14 (d, 6.3 Hz, 3H).

Example 5

2-[2-Methyl-4-(2-methyl-[1,3']bipyrrolidinyl-1'-yl)-phenyl]-1-oxo-2,8-diaza-spiro[4.5]decane-8-carboxylic acid tert-butyl ester

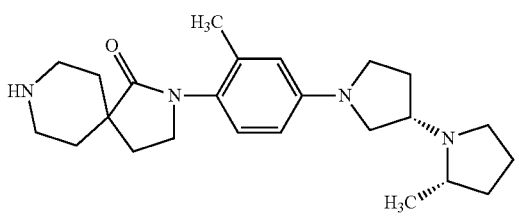

The title compound was prepared in a manner substantially the same as Example 1 to obtain the title compound as a semi-solid.

LC, R_T=2.62 mins; MS: 497.

¹H NMR (CDCl₃, 300 MHz), δ (ppm): Two sets of spectra were observed.

Example 6

2-[2-Methyl-4-((2S,3'S)-2-methyl-[1,3']bipyrrolidinyl-1'-yl)-phenyl]-2,8-diaza-spiro[4.5]decan-1-one

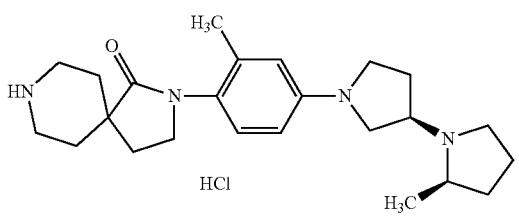 [SMILES: Cc1cc(N2CC[C@@H](N3CCC[C@H]3C)C2)ccc1N1CCC2(CCNCC2)C1=O ; Cl]

2-[2-Methyl-4-((2S,3'S)-2-methyl-[1,3']bipyrrolidinyl-1'-yl)-phenyl]-1-oxo-2,8-diaza-spiro[4.5]decane-8-carboxylic acid tert-butyl ester (150 mg) was treated with 1 mL (excess) of 4M HCl in dioxane at 0° C. The stirring was continued at rt for 1 h. The solvent was evaporated and the solid was further dried under high vacuum at rt for 2 h to obtain the title compound as a tan solid.

LC, R_T=1.41 mins; MS: 397.

Example 7

2-[2-Methyl-4-((2R,3'R)-2-methyl-[1,3']bipyrrolidinyl-1'-yl)-phenyl]-2,8-diaza-spiro[4.5]decan-1-one Hydrochloride The title compound was prepared in a manner substantially the same as Example 1.
LC, $R_T$=1.38 mins; MS: 397.

Example 8

2-[2-Methyl-4-((2R,3'S)-2-methyl-[1,3']bipyrrolidinyl-1'-yl)-phenyl]-2,8-diaza-spiro[4.5]decan-1-one Hydrochloride

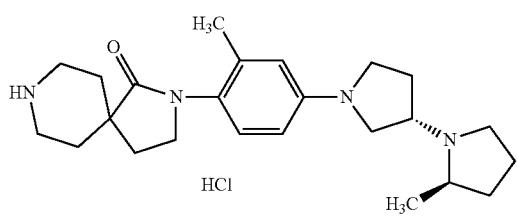 [SMILES: Cc1cc(N2CC[C@H](N3CCC[C@H]3C)C2)ccc1N1CCC2(CCNCC2)C1=O ; Cl]

The title compound was prepared in a manner substantially the same as Example 1
LC, $R_T$=1.4 mins; MS: 397.

Example 9

2-[2-Methyl-4-((2S,3'R)-2-methyl-[1,3']bipyrrolidinyl-1'-yl)-phenyl]-2,8-diaza-spiro[4.5]decan-1-one Hydrochloride

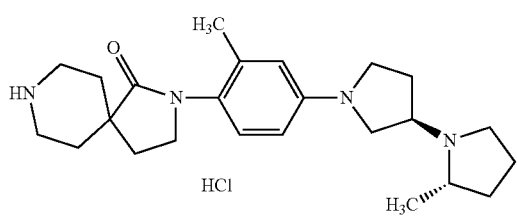 [SMILES: Cc1cc(N2CC[C@@H](N3CCC[C@@H]3C)C2)ccc1N1CCC2(CCNCC2)C1=O ; Cl]

The title compound was prepared in a manner substantially the same as Example 1.
LC, $R_T$=1.35 mins; MS: 397.

Example 10

8-Cyclopentyl methyl-2-[2-methyl-4-((2R,3'S)-2-methyl-[1,3']bipyrrolidinyl-1'-l)-phenyl]-2,8-diaza-spiro[4.5]decan-1-one

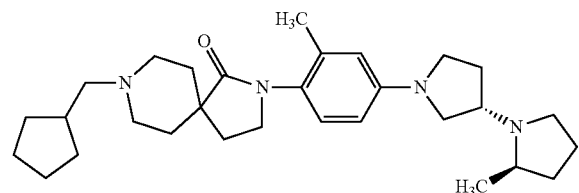

To 2-[2-methyl-4-((2R,3'S)-2-methyl-[1,3']bipyrrolidinyl-1'-yl)-phenyl]-2,8-diaza-spiro[4.5]decan-1-one (40 mg, 0.1 mmol) was added a solution of cyclopentane-carboxaldehyde (CAS 872-53-7, MW 98.14) (30 mg, 0.3 mmol) in 5 mL, followed by powder sodium triacetoxyborohydride under $N_2$ at r.t. The yellowish milky suspension was stirred at r.t. overnight. The reaction was quenched with DCM (5 mL), NaHCO3 aq. (2 mL) and NaOH (1N, 1 mL). The two layers were separated, and the aqueous layer was extracted with DCM (5 mL). The combined DCM extracts were washed with sodium bicarbonate (5 mL), and brine (5 mL), dried (anhydrous potassium carbonate), filtered, and the solution was directly loaded onto a 10-g waters silica gel column, eluted with DCM, followed by 5% of 7N $NH_3$/MeOH in DCM. The collection of the fractions was evaporated to obtain a solid.
LC, $R_T$=1.65 mins; MS: 479.
$^1$H NMR (CDCl$_3$, 300 MHz), δ (ppm): 6.96 (m, 1H), 6.39 (m, 2H), 3.55 (t, 7.2 Hz, 2H), 3.45-3.17 (m, 5H), 3.44-3.19 (m, 3H), 2.53 (q, 8.1 Hz, 1H), 2.25 (m, 3H), 2.07-1.91 (m, 8H), 1.74 (m, 4H), 1.62-1.41 (m, 12H), 1.20 (m, 2H), 1.14 (d, 6.3 Hz, 3H).

Example 11

8-Cyclopentylmethyl-2-[2-methyl-4-((2R,3'R)-2-methyl-[1,3']bipyrrolidinyl-1'-l)-phenyl]-2,8-diaza-spiro[4.5]decan-1-one

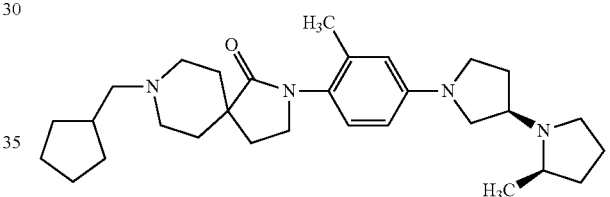

The title compound was prepared in a manner substantially the same as Example 1.
LC, $R_T$=1.68 mins; MS: 479.
$^1$H NMR (CDCl$_3$, 300 MHz), δ (ppm): 6.96 (m, 1H), 6.39 (m, 2H), 2.55 (t, 7.2 Hz, 2H), 3.50 (t, 7.2 Hz, 1H), 3.45-3.10 (m, 4H), 3.01 (m, 1H), 2.89 (m, bs, 1H), 2.78 (sextet, 6.9 Hz, 1H), 2.50 (q, 8.4 Hz, 1H), 2.27 (m, 3H), 2.07-1.91 (m, 8H), 1.74 (m, 4H), 1.62-1.41 (m, 12H), 1.20 (m, 2H), 1.13 (d, 6.3 Hz, 3H).

Example 12

8-Cyclopentylmethyl-2-[2-methyl-4-((2S,3'R)-2-methyl-[1,3']bipyrrolidinyl-1'-l)-phenyl]-2,8-diaza-spiro[4.5]decan-1-one

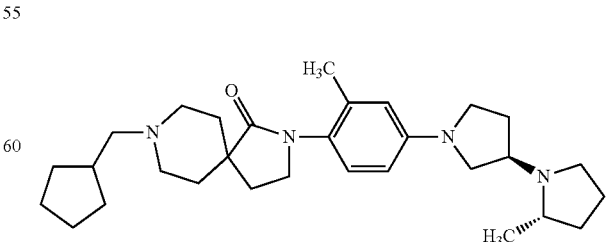

The title compound was prepared in a manner substantially the same as Example 1.

LC, R$_T$=1.7 mins; MS: 479.

$^1$H NMR (CDCl$_3$, 300 MHz), δ (ppm): 6.96 (m, 1H), 6.39 (m, 2H), 3.55 (t, 7.2 Hz, 2H), 3.45-3.17 (m, 5H), 3.44-3.19 (m, 3H), 2.53 (q, 8.1 Hz, 1H), 2.25 (m, 3H), 2.07-1.91 (m, 8H), 1.74 (m, 4H), 1.62-1.41 (m, 12H), 1.20 (m, 2H), 1.14 (d, 6.3 Hz, 3H).

Example 13

8-Cyclopentylmethyl-2-[2-methyl-4-((2S,3'S)-2-methyl-[1,3']bipyrrolidinyl-1'-l)-phenyl]-2,8-diaza-spiro[4.5]decan-1-one

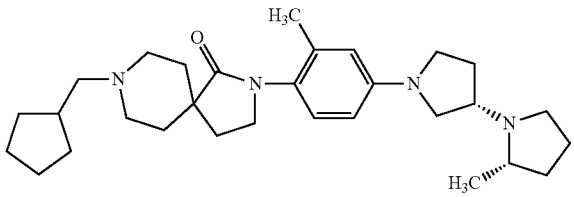 [SMILES: Cc1cc(N2CC[C@H](N3CCC[C@@H]3C)C2)ccc1N1CCC2(CCN(CC3CCCC3)CC2)C1=O]

The title compound was prepared in a manner substantially the same as Example 1.

LC, R$_T$=1.67 mins; MS: 479.

$^1$H NMR (CDCl$_3$, 300 MHz), δ (ppm): 6.96 (m, 1H), 6.39 (m, 2H), 2.55 (t, 7.2 Hz, 2H), 3.50 (t, 7.2 Hz, 1H), 3.45-3.10 (m, 4H), 3.01 (m, 1H), 2.89 (m, bs, 1H), 2.78 (sextet, 6.9 Hz, 1H), 2.50 (q, 8.4 Hz, 1H), 2.27 (m, 3H), 2.07-1.91 (m, 8H), 1.74 (m, 4H), 1.62-1.41 (m, 12H), 1.20 (m, 2H), 1.13 (d, 6.3 Hz, 3H).

Example 14

8-Cyclopentylmethyl-2-[2-methyl-4-(2-methyl-[1,3']bipyrrolidinyl-1'-l)-phenyl]-2,8-diaza-spiro[4.5]decan-1-one

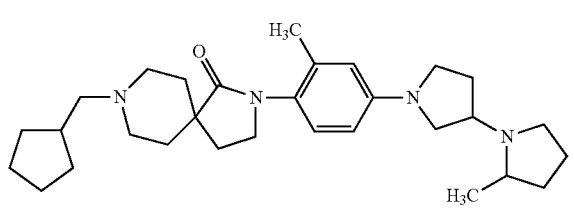 [SMILES: Cc1cc(N2CCC(N3CCCC3C)C2)ccc1N1CCC2(CCN(CC3CCCC3)CC2)C1=O]

The title compound was prepared in a manner substantially the same as Example 1.

LC, R$_T$=1.63 mins; MS: 479.

$^1$H NMR (CDCl$_3$, 300 MHz), δ (ppm): two sets of spectra were observed. It is ambiguous to assign the spectra.

Example 15

2-[2-Methyl-4-((2R,3'S)-2-methyl-[1,3']bipyrrolidinyl-1'-yl)-phenyl]-8-(4-trifluoromethoxy-benzoyl)-2,8-diaza-spiro[4.5]decan-1-one

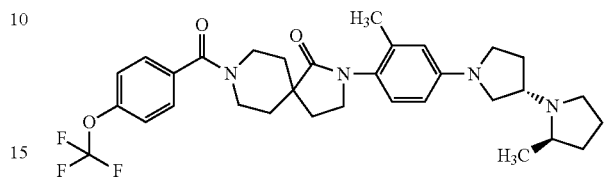

To a solution of acid chloride in DCM was added 2-[2-methyl-4-((2S,3'S)-2-methyl-[1,3']bipyrrolidinyl-1'-yl)-phenyl]-2,8-diaza-spiro[4.5]decan-1-one (~20 mg, 0.06 mmol) followed by potassium carbonate (40 mg, excess). The colorless suspension was allowed to stir under nitrogen overnight at rt. The reaction was quenched with DCM (5 mL) and aq. sodium bicarbonate solution (2 mL). The two layers were separated. The aqueous layer was extracted with DCM (5 mL). The combined DCM solution was dried over K$_2$CO$_3$, directly loaded onto a 10-g silica gel column, eluted with DCM and 5% 7N NH$_3$ solution of MeOH in DCM to get the product, as in the table.

LC, R$_T$=2.52 mins; MS: 585.

$^1$H NMR (CDCl$_3$, 300 MHz), δ (ppm): 7.49 (d, 8.4 Hz, 2H), 7.25 (d, 8.4 Hz, 2H), 6.95 (m, 1H), 6.39 (m, 2H), 3.62 (m, 2H), 3.45-3.21 (m, 5H), 2.99 (m, 1H), 2.80 (m, 1H), 2.54 (q, 8.4 Hz, 1H), 2.24 (m, 1H), 2.19-1.91 (m, 8H), 1.87-1.39 (m, 10H), 1.15 (d, 6.3 Hz, 3H).

Example 16

2-[2-Methyl-4-((2R,3'R)-2-methyl-[1,3']bipyrrolidinyl-1'-yl)-phenyl]-8-(4-trifluoromethoxy-benzoyl)-2,8-diaza-spiro[4.5]decan-1-one

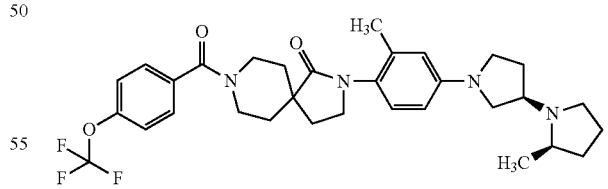

The title compound was prepared in a manner substantially the same as Example 15.

LC, R$_T$=2.62 mins; MS: 585.

$^1$H NMR (CDCl$_3$, 300 MHz), δ (ppm): 7.49 (d, 8.4 Hz, 2H), 7.25 (d, 8.4 Hz, 2H), 6.95 (m, 1H), 6.39 (m, 2H), 3.62 (m, 2H), 3.51 (t, 7.2 Hz, 1H), 3.42-3.20 (m, 4H), 3.02 (m, 1H), 2.78 (m, 1H), 2.54 (q, 8.4 Hz, 1H), 2.24-1.92 (m, 9H), 1.87-1.39 (m, 10H), 1.14 (d, 6.3 Hz, 3H).

Example 17

2-[2-Methyl-4-((2S,3'R)-2-methyl-[1,3']bipyrrolidinyl-1'-yl)-phenyl]-8-(4-trifluoromethoxy-benzoyl)-2,8-diaza-spiro[4.5]decan-1-one

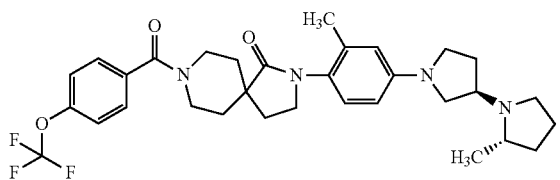 [SMILES: Cc1cc(N2CC[C@@H](N3CCC[C@@H]3C)C2)ccc1N1CCC2(CCN(C(=O)c3ccc(OC(F)(F)F)cc3)CC2)C1=O]

The title compound was prepared in a manner substantially the same as Example 15.

LC, $R_T$=2.62 mins; MS: 585.

$^1$H NMR (CDCl$_3$, 300 MHz), δ (ppm): 7.49 (d, 8.4 Hz, 2H), 7.25 (d, 8.4 Hz, 2H), 6.95 (m, 1H), 6.39 (m, 2H), 3.62 (m, 2H), 3.45-3.21 (m, 5H), 2.99 (m, 1H), 2.80 (m, 1H), 2.54 (q, 8.4 Hz, 1H), 2.24 (m, 1H), 2.19-1.91 (m, 8H), 1.87-1.39 (m, 10H), 1.15 (d, 6.3 Hz, 3H).

Example 18

2-[2-Methyl-4-(2-methyl-[1,3']bipyrrolidinyl-1'-yl)-phenyl]-8-(4-trifluoromethoxy-benzoyl)-2,8-diaza-spiro[4.5]decan-1-one

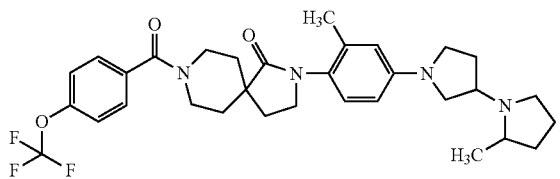 [SMILES: Cc1cc(N2CCC(N3CCCC3C)C2)ccc1N1CCC2(CCN(C(=O)c3ccc(OC(F)(F)F)cc3)CC2)C1=O]

The title compound was prepared in a manner substantially the same as Example 15.

LC, $R_T$=2.62 mins; MS: 585.

$^1$H NMR (CDCl$_3$, 300 MHz), δ (ppm): two sets of spectra were observed. It is ambiguous to assign the spectra.

Example 19

2-[2-Methyl-4-((2S,3'S)-2-methyl-[1,3']bipyrrolidinyl-1'-yl)-phenyl]-8-(4-trifluoromethoxy-benzoyl)-2,8-diaza-spiro[4.5]decan-1-one

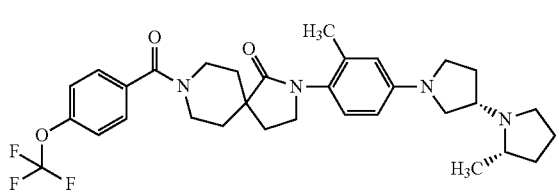 [SMILES: Cc1cc(N2CC[C@H](N3CCC[C@@H]3C)C2)ccc1N1CCC2(CCN(C(=O)c3ccc(OC(F)(F)F)cc3)CC2)C1=O]

The title compound was prepared in a manner substantially the same as Example 15.

LC $R_T$=2.55 min, MS: 585 (M+H).

$^1$H NMR (300 MHz, CDCl$_3$) δ (ppm): 7.49 (d, 8.4 Hz, 2H), 7.25 (d, 8.4 Hz, 2H), 6.95 (m, 1H), 6.39 (m, 2H), 3.62 (m, 2H), 3.51 (t, 7.2 Hz, 1H), 3.42-3.20 (m, 4H), 3.02 (m, 1H), 2.78 (m, 1H), 2.54 (q, 8.4 Hz, 1H), 2.24-1.92 (m, 9H), 1.87-1.39 (m, 10H), 1.14 (d, 6.3 Hz, 3H).

Example 20

2-[2-Methyl-4-((2S,3'S)-2-methyl-[1,3']bipyrrolidinyl-1'-yl)-phenyl]-1-oxo-2,9-diaza-spiro[5.5]undecane-9-carboxylic acid tert-butyl ester

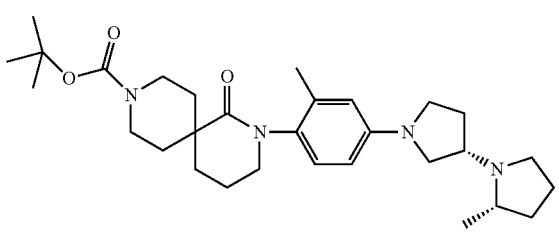 [SMILES: Cc1cc(N2CC[C@H](N3CCC[C@@H]3C)C2)ccc1N1CCCC2(CCN(C(=O)OC(C)(C)C)CC2)C1=O]

The title compound was prepared in a manner substantially the same as Example 1.

LC $R_T$=4.88 min, MS: 511 (M+H).

$^1$H NMR (300 MHz, CDCl$_3$) δ (ppm): 6.92 (d, 1H), 6.39-6.37 (m, 2H), 3.81-3.73 (m, 2H), 3.59-3.40 (m, 2H), 3.36-3.20 (m, 7H), 3.01-2.9 (m, 1H), 2.79-2.76 (m, 1H), 2.52 (q, 1H), 2.17-2.13 (m, 2H), 2.10 (s, 3H), 2.04-1.51 (m, 13H), 1.45 (s, 9H), 1.13 (d, 3H).

Example 21

2-[4-((2S,3'S)-2-Methyl-[1,3']bipyrrolidinyl-1'-yl)-phenyl]-1-oxo-2,9-diaza-spiro[5.5]undecane-9-carboxylic acid tert-butyl ester

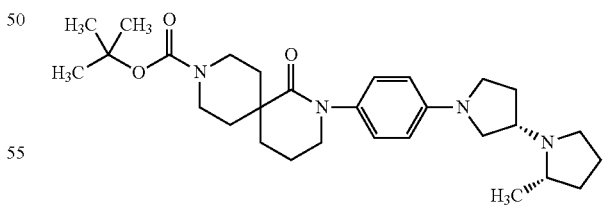

The title compound was prepared in a manner substantially the same as Example 1.

LC $R_T$=4.68 min, MS: 497 (M+H).

$^1$H NMR (300 MHz, CDCl3) δ (ppm): 7.01 (d, 2H), 6.52 (d, 2H), 3.83-3.75 (m, 2H), 3.58 (t, 2H), 3.50 (t, 1H), 3.38-3.19 (m, 7H), 3.04-2.98 (m, 1H), 2.79-2.75 (m, 1H), 2.53 (q, 1H), 2.19-2.10 (m, 4H), 2.03-1.71 (m, 7H), 1.52-1.47 (m, 2H), 1.45 (s, 9H), 1.13 (d, 3H).

Example 22

4-{[2-Fluoro-4-((2S,3'S)-2-methyl-[1,3']bipyrrolidinyl-1'-yl)-phenyl]-methyl-carbamoyl}-4-propyl-piperidine-1-carboxylic acid tert-butyl ester

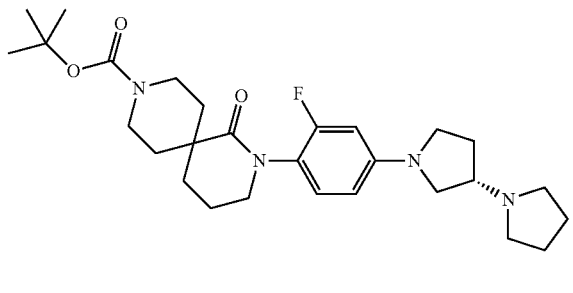 [SMILES: CC(C)(C)OC(=O)N1CCC2(CCCN(c3ccc(N4CC[C@H](N5CCCC5)C4)cc3F)C2=O)CC1]

The title compound was prepared in a manner substantially the same as Example 1.

LC $R_T$=4.9 min, MS: 515 (M+H).

$^1$H NMR (300 MHz, CDCl3) δ (ppm): 6.98 (t, 1H), 6.30-6.23 (m, 2H), 3.79-3.72 (m, 2H), 3.54 (t, 2H), 3.47 (t, 1H), 3.36-3.19 (m, 7H), 3.00 (dt, 1H), 2.77 (q, 1H), 2.51 (q, 1H), 2.17-2.09 (m, 4H), 2.03-1.75 (m, 7H), 1.52-1.46 (m, 2H), 1.45 (s, 9H), 1.12 (d, 3H).

Example 23

3-[2-Methyl-4-((2S,3'S)-2-methyl-[1,3']bipyrrolidinyl-1'-yl)-phenyl]-2,9-diaza-spiro[5.5]undecan-1-one Hydrochloride

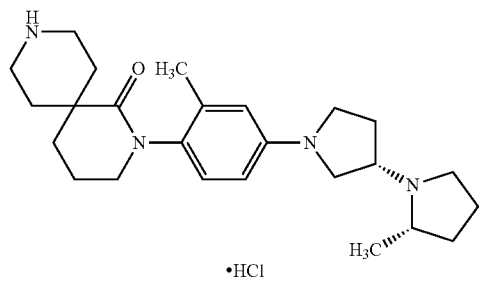 [SMILES: Cc1cc(N2CC[C@H](N3CCC[C@@H]3C)C2)ccc1N1CCCC2(CCNCC2)C1=O ; Cl]

The title compound was prepared in a manner substantially the same as Example 1.

LC $R_T$=1.72 min, MS: 411 (M+H).

$^1$H NMR (300 MHz, CDCl$_3$) δ (ppm): 7.01 (d, 1H), 6.63-6.60 (m, 2H), 4.16 (t, 1H), 3.81-3.21 (m, 17H), 3.31 (s, 3H), 2.60-2.45 (m, 1H), 2.38-2.28 (m, 2H), 2.16-2.01 (m, 5H), 1.86-1.77 (m, 3H), 1.50 (d, 3H).

Example 24

3-[4-((2S,3'S)-2-methyl-[1,3']bipyrrolidinyl-1'-yl)-phenyl]-2,9-diaza-spiro[5.5]undecan-1-one Hydrochloride

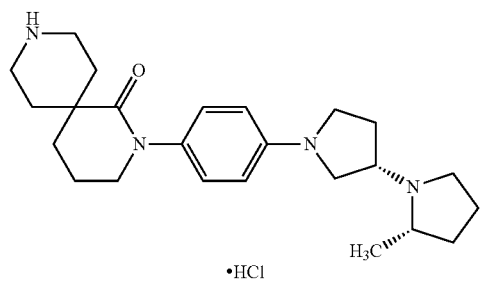 [SMILES: C[C@H]1CCCN1[C@H]1CCN(c2ccc(N3CCCC4(CCNCC4)C3=O)cc2)C1 ; Cl]

The title compound was prepared in a manner substantially the same as Example 1.

LC $R_T$=1.59 min, MS: 397 (M+H).

$^1$H NMR (300 MHz, CDCl$_3$) δ (ppm): 7.09 (d, 2H), 6.74 (d, 2H), 4.16 (t, 1H), 3.81-3.19 (m, 17H), 2.60-2.47 (m, 1H), 2.38-2.27 (m, 2H), 2.15-1.97 (m, 5H), 1.84-1.76 (m, 3H), 1.50 (d, 3H).

Example 25

3-[2-Fluoro-4-((2S,3'S)-2-methyl-[1,3']bipyrrolidinyl-1'-yl)-phenyl]-2,9-diaza-spiro[5.5]undecan-1-one Hydrochloride

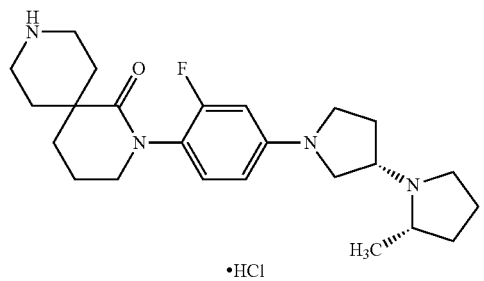 [SMILES: C[C@H]1CCCN1[C@H]1CCN(c2ccc(N3CCCC4(CCNCC4)C3=O)c(F)c2)C1 ; Cl]

The title compound was prepared in a manner substantially the same as Example 1.

LC $R_T$=1.74 min, MS: 415 (M+H).

$^1$H NMR (300 MHz, CDCl$_3$) δ (ppm): 7.13 (t, 1H), 6.53-6.49 (m, 2H), 4.21 (t, 1H), 3.76-3.21 (m, 17H), 2.57-2.50 (m, 1H), 2.36-2.26 (m, 2H), 2.12-1.97 (m, 5H), 1.84-1.77 (m, 3H), 1.50 (d, 3H).

Example 26

3-[2-Methyl-4-((2S,3'S)-2-methyl-[1,3']bipyrrolidinyl-1'-yl)-phenyl]-9-(pyridine-4-carbonyl)-2,9-diaza-spiro[5.5]undecan-1-one

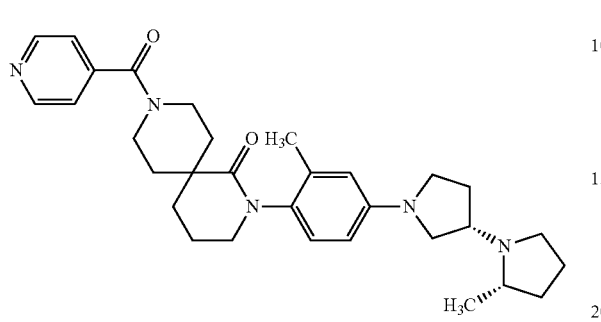

The title compound was prepared in a manner substantially the same as Example 1.

LC $R_T$=2.42 min, MS: 516 (M+H).

$^1$H NMR (300 MHz, CDCl$_3$) δ (ppm): 8.67-8.63 (m, 2H), 7.77-7.73 (m, 1H), 7.34 (dd, 1H), 6.93-6.91 (m, 1H), 6.40-6.38 (m, 2H), 4.20-3.88 (m, 4H), 3.60-3.21 (m, 7H), 3.05-3.02 (m, 1H), 2.81 (q, 1H), 2.55 (q, 1H), 2.13-1.46 (m, 17H), 1.15 (d, 3H).

Example 27

9-(Furan-3-carbonyl)-2-[2-methyl-4-((2S,3'S)-2-methyl-[1,3']bipyrrolidinyl-1'-yl)-phenyl]-2,9-diaza-spiro[5.5]undecan-1-one

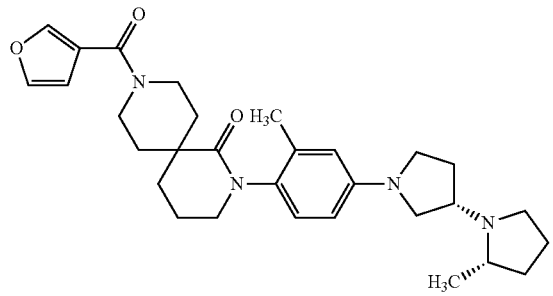 [SMILES: Cc1cc(N2CC[C@H](N3CCC[C@@H]3C)C2)ccc1N1CCCC2(CCN(C(=O)c3ccoc3)CC2)C1=O]

The title compound was prepared in a manner substantially the same as Example 1.

LC $R_T$=2.65 min, MS: 505 (M+H).

$^1$H NMR (300 MHz, CDCl$_3$) δ (ppm): 7.68 (s, 1H), 7.40 (t, 1H), 6.92 (d, 1H), 6.55 (s, 1H), 6.40-6.38 (m, 2H), 4.05-3.91 (m, 2H), 3.64-3.56 (m, 4H), 3.42-3.30 (m, 2H), 3.27-3.21 (m, 2H), 3.02 (dt, 1H), 2.79 (q, 1H), 2.53 (q, 1H), 2.10 (s, 3H), 2.17-1.74 (m, 10H), 1.62-1.48 (m, 4H), 1.13 (d, 3H).

Example 28

9-Benzoyl-2-[4-((2S,3'S)-2-methyl-[1,3']bipyrrolidinyl-1'-yl)-phenyl]-2,9-diaza-spiro[5.5]undecan-1-one

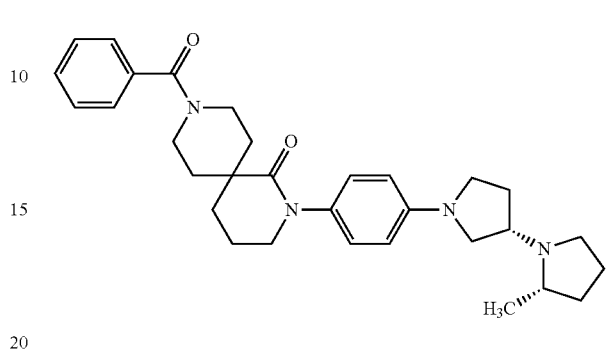

The title compound was prepared in a manner substantially the same as Example 1.

LC $R_T$=2.67 min, MS: 501 (M+H).

$^1$H NMR (300 MHz, CDCl$_3$) δ (ppm): 7.31 (m, 5H), 7.22 (d, 2H), 6.94 (d, 2H), 4.00-3.90 (m, 1H), 3.68 (m, 2H), 3.50-3.15 (m, 9H), 2.96 (q, 1H), 2.65 (q, 1H), 2.10-1.67 (m, 11H), 1.59-1.54 (m, 2H), 1.37-1.23 (m, 1H), 1.17 (d, 3H).

Example 29

9-(4-Fluoro-benzoyl-2-[4-((2S,3'S)-2-methyl-[1,3']bipyrrolidinyl-1'-yl)-phenyl]-2,9-diaza-spiro[5.5]undecan-1-one

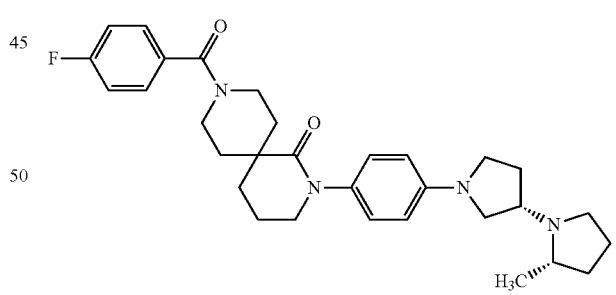

The title compound was prepared in a manner substantially the same as Example 1.

LC $R_T$=2.74 min, MS: 519 (M+H).

$^1$H NMR (300 MHz, CDCl$_3$) δ (ppm): 7.34 (dt, 2H), 7.00 (t, 2H), 6.94 (d, 2H), 6.45 (d, 2H), 4.01-3.90 (m, 1H), 3.80-3.61 (m, 2H), 3.52 (t, 2H), 3.43 (t, 1H), 3.33-3.15 (m, 5H), 2.94 (dt, 1H), 2.72 (q, 1H), 2.46 (q, 1H), 2.10-1.37 (m, 14H), 1.06 (d, 3H).

Example 30

9-Cyclohexanecarbonyl-2-[2-fluoro-4-((2S,3'S)-2-methyl-[1,3']bipyrrolidinyl-1'-yl)-phenyl]-2,9-diaza-spiro[5.5]undecan-1-one

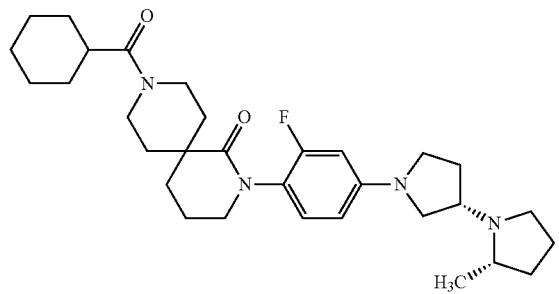 [SMILES: C[C@H]1CCCN1[C@H]1CCN(c2ccc(N3CCCC4(CCN(C(=O)C5CCCCC5)CC4)C3=O)c(F)c2)C1]

The title compound was prepared in a manner substantially the same as Example 1.

LC $R_T$=2.97 min, MS: 525 (M+H).

$^1$H NMR (300 MHz, CDCl$_3$) δ (ppm): 6.92 (t, 1H), 6.22-6.18 (m, 2H), 3.84-3.70 (m, 2H), 3.49-3.18 (m, 10H), 3.91 (q, 1H), 2.62 (q, 1H), 2.50-2.33 (m, 1H), 2.15-1.18 (m, 24H), 1.12 (d, 3H).

Example 31

2-[2-Fluoro-4-((2S,3'S)-2-methyl-[1,3']bipyrrolidinyl-1'-yl)-phenyl]-9-(tetrahydro-pyran-4-carbonyl)-2,9-diaza-spiro[5.5]undecan-1-one

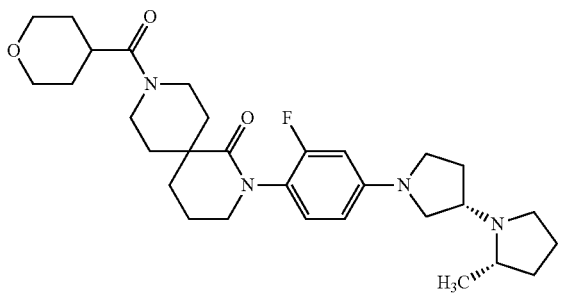 [SMILES: C[C@H]1CCCN1[C@H]1CCN(c2ccc(N3CCCC4(CCN(C(=O)C5CCOCC5)CC4)C3=O)c(F)c2)C1]

The title compound was prepared in a manner substantially the same as Example 1.

LC $R_T$=2.45 min, MS: 527 (M+H).

$^1$H NMR (300 MHz, CDCl$_3$) δ (ppm): 6.93 (t, 1H), 6.24-6.18 (m, 2H), 3.95-3.75 (m, 6H), 3.48-3.30 (m, 10H), 3.19-3.13 (m, 2H), 3.04 (q, 1H), 2.74-2.67 (m, 2H), 2.40-2.32 (m, 1H), 2.13-1.43 (m, 15H), 1.17 (d, 3H).

Example 32

9-Isopropyl-2-[2-methyl-4-((2S,3'S)-2-methyl-[1,3']bipyrrolidinyl-1'-yl)-phenyl]-2,9-diaza-spiro[5.5]undecan-1-one

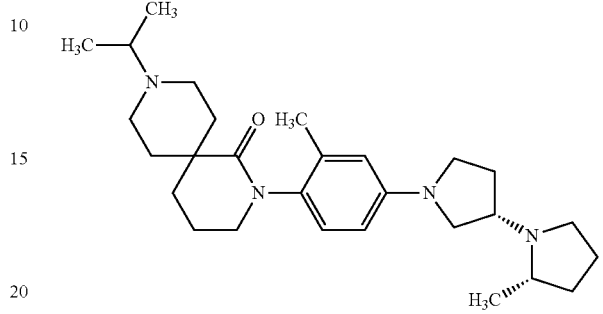

The title compound was prepared in a manner substantially the same as Example 1.

LC $R_T$=1.77 min, MS: 453 (M+H).

$^1$H NMR (300 MHz, CDCl$_3$) δ (ppm): 6.91 (d, 1H), 6.39-6.36 (m, 2H), 3.53-3.48 (m, 2H), 3.38-3.18*m, 5H), 2.99 (dt, 1H), 2.86-2.69 (m, 4H), 2.55-2.44 (m, 4H), 2.27-2.14 (m, 2H), 2.10 (s, 3H), 2.03-1.52 (m, 11H), 1.12 (d, 3H), 1.05 (d, 6H).

Example 33

9-Cyclohexylmethyl-2-[2-methyl-4-((2S,3'S)-2-methyl-[1,3']bipyrrolidinyl-1'-yl)-phenyl]-2,9-diaza-spiro[5.5]undecan-1-one

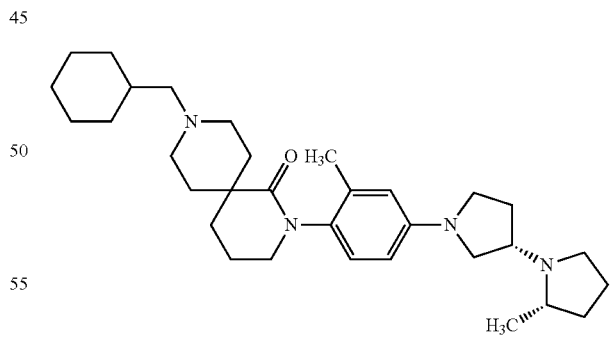

The title compound was prepared in a manner substantially the same as Example 1.

LC $R_T$=2.29 min, MS: 507 (M+H).

$^1$H NMR (300 MHz, CDCl$_3$) δ (ppm): 6.91 (d, 1H), 6.38-6.36 (m, 2H), 3.54-3.48 (m, 2H), 3.39-3.18 (m, 5H), 2.99 (dt, 1H), 2.77-2.66 (m, 4H), 2.51 (q, 1H), 2.23 (d, 2H), 2.13 (d, 2H), 2.09 (s, 3H), 2.03-1.43 (m, 17H), 1.24-1.16 (m, 4H), 1.12 (d, 3H), 0.91-0.83 (m, 3H).

Example 34

9-Cyclopropylmethyl-2-[4-((2S,3'S)-2-methyl-[1,3']bipyrrolidinyl-1'-yl)-phenyl]-2,9-diaza-spiro[5.5]undecan-1-one

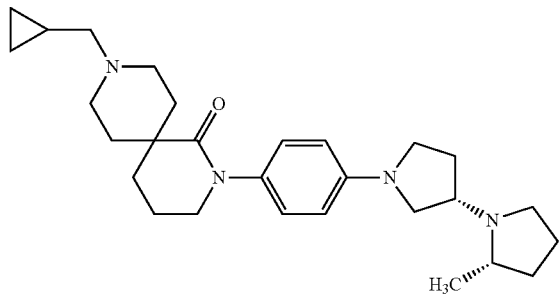 [SMILES: C[C@H]1CCCN1[C@H]1CCN(c2ccc(N3CCCC4(CCN(CC5CC5)CC4)C3=O)cc2)C1]

The title compound was prepared in a manner substantially the same as Example 1.

LC $R_T$=3.33 min, MS: 451 (M+H).

$^1$H NMR (300 MHz, CDCl$_3$) δ (ppm): 6.93 (d, 2H), 6.43 (d, 2H), 3.48 (t, 2H), 3.41 (t, 1H), 3.29-3.12 (m, 4H), 2.91 (dt, 1H), 2.82-2.77 (m, 2H), 2.69-2.67 (m, 2H), 2.43 (q, 1H), 2.35-2.31 (m, 1H), 2.20 (d, 2H), 2.17-1.48 (m, 14H), 1.04 (d, 3H), 0.84-0.73 (m, 1H), 0.42 (m, 2H), 0.01 (m, 2H).

Example 35

2-[4-((2S,3'S)-2-Methyl-[1,3']bipyrrolidinyl-1'-yl)-phenyl]-9-(tetrahydro-pyran-4-yl)-2,9-diaza-spiro[5.5]undecan-1-one

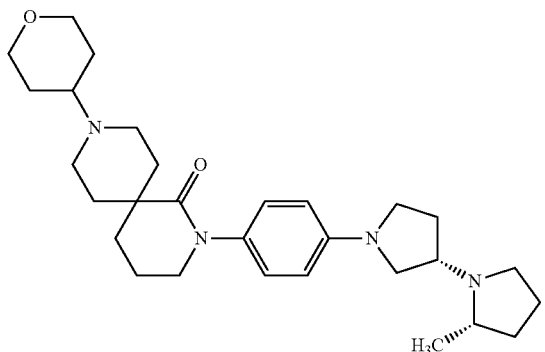 [SMILES: C[C@H]1CCCN1[C@H]1CCN(c2ccc(N3CCCC4(CCN(C5CCOCC5)CC4)C3=O)cc2)C1]

The title compound was prepared in a manner substantially the same as Example 1.

LC $R_T$=3.24 min, MS: 481 (M+H).

$^1$H NMR (300 MHz, CDCl$_3$) δ (ppm): 7.01 (d, 2H), 6.51 (d, 2H), 4.00 (dd, 2H), 3.56 (t, 2H), 3.49 (t, 1H), 3.40-3.20 (m, 7H), 2.99 (dt, 1H), 2.99-2.83 (m, 2H), 2.76 (q, 1H), 2.53-2.44 (m, 5H), 2.28-1.54 (m, 16H), 1.12 (d, 3H).

Example 36

9-Benzyl-2-[2-fluoro-4-((2S,3'S)-2-methyl-[1,3']bipyrrolidinyl-1'-yl)-phenyl]-2,9-diaza-spiro[5.5]undecan-1-one

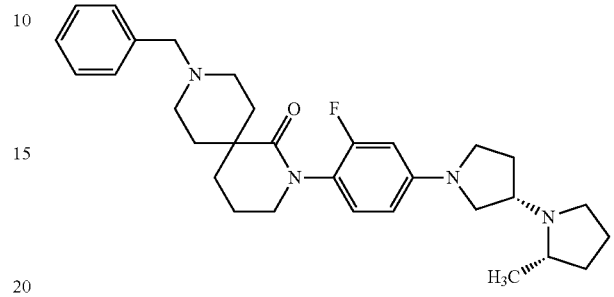

The title compound was prepared in a manner substantially the same as Example 1.

LC $R_T$=2.14 min, MS: 505 (M+H).

$^1$H NMR (300 MHz, CDCl$_3$) δ (ppm): 7.37-7.24 (m, 5H), 7.00 (t, 1H), 6.31-6.24 (m, 2H), 3.54-3.46 (m, 4H), 3.36-3.20 (m, 4H), 3.00 (dt, 1H), 2.79-2.74 (m, 3H), 2.52 (q, 1H), 2.35-2.27 (m, 4H), 2.04-1.76 (m, 10H), 1.60-1.54 (m, 3H), 1.13 (d, 3H).

Example 37

2-[2-Fluoro-4-((2S,3'S)-2-methyl-[1,3']bipyrrolidinyl-1'-yl)-phenyl]-9-furan-2-ylmethyl-2,9-diaza-spiro[5.5]undecan-1-one The title compound was prepared in a manner substantially the same as Example 1.

LC $R_T$=2 min, MS: 495 (M+H).

$^1$H NMR (300 MHz, CDCl$_3$) δ (ppm): 7.37 (d, 1H), 6.98 (t, 1H), 6.31-6.23 (m, 3H), 6.18 (d, 1H), 3.56-3.44 (m, 5H), 3.35-3.18 (m, 4H), 2.99 (dt, 1H), 2.78-2.72 (m, 3H), 2.53-2.42 (m, 3H), 2.30-2.24 (m, 2H), 2.19-2.05 (m, 1H), 1.99-1.77 (m, 8H), 1.62-1.40 (m, 3H), 1.11 (d, 3H).

Example 38

2-{4-[4-(2S-2-Methyl-pyrrolidin-1-yl)-piperidin-1-yl]-phenyl}-1-oxo-2,8-diaza-spiro[4,5]decane-8-carboxylic acid tert-butyl ester

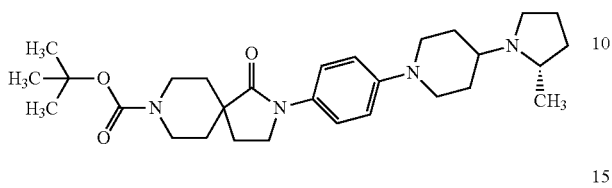

The title compound was prepared in a manner substantially the same as Example 1.

LC $R_T$=2.61 min, MS: 497 (M+H).

$^1$H NMR (300 MHz, CDCl$_3$) δ (ppm): 7.49 (d, 2H), 6.94 (d, 2H), 4.04 (d, 2H), 3.78-3.67 (m, 4H), 3.04 (t, 2H), 2.92 (dd, 2H), 2.83-2.50 (m, 4H), 2.07 (t, 2H), 1.98-1.6 (m, 12H), 1.45 (s, 9H), 1.3 (d, 3H).

Example 39

2-{4-[4-(2S-2-Methyl-pyrrolidin-1-yl)-piperidin-1-yl]-2-trifluoromethyl-phenyl}-1-oxo-2,8-diaza-spiro[4.5]decane-8-carboxylic acid tert-butyl ester

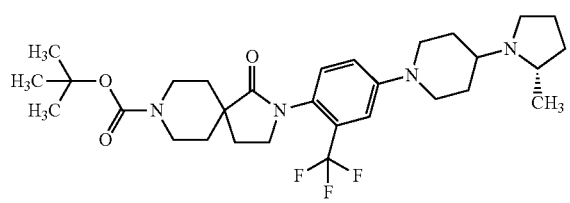 [SMILES: C[C@H]1CCCN1C1CCN(c2ccc(N3CCC4(CCN(C(=O)OC(C)(C)C)CC4)C3=O)c(C(F)(F)F)c2)CC1]

The title compound was prepared in a manner substantially the same as Example 1.

LC $R_T$=2.75 min, MS: 565 (M+H).

$^1$H NMR (300 MHz, CDCl$_3$) δ (ppm): 7.16 (d, 1H), 7.04 (2, H), 3.96 (d, 2H), 3.74 (d, 2H), 3.60 (d, 2H), 3.12-3.01 (m, 4H), 2.87 (m, 3H), 2.66 (dd, 1H), 2.10 (t, 2H), 2.0-1.82 (m, 8H), 1.77-1.61 (m, 2H), 1.5 (d, 2H), 1.4 (s, 9H), 1.1 (d, 3H).

Example 40

2-{4-[4-(2S-2-Methyl-pyrrolidin-1-yl)-piperidin-1-yl]-2-fluoro-phenyl}-1-oxo-2,8-diaza-spiro[4.5]decane-8-carboxylic acid tert-butyl ester

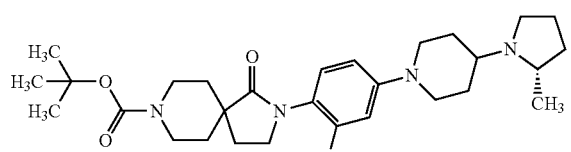

The title compound was prepared in a manner substantially the same as Example 1.

LC $R_T$=2.71 min, MS: 516 (M+H).

$^1$H NMR (300 MHz, CDCl$_3$) δ (ppm): 7.17 (t, 1H), 6.65 (dd, 2H), 3.99 (d, 2H) 3.68 (m, 4H), 3.09 (t, 2H), 2.95 (d, 2H), 2.74 (m, 4H), 2.09 (t, 2H), 1.99-1.62 (m, 10H), 1.54-1.41 (m, 11H), 1.09 (d, 3H).

Example 41

2-{4-[3-((2S,3'S)-2-Methyl-piperidin-1-yl)-pyrrolidin-1-yl]-phenyl}-1-oxo-2,8-diaza-spiro[4.5]decane-8-carboxylic acid tert-butyl ester

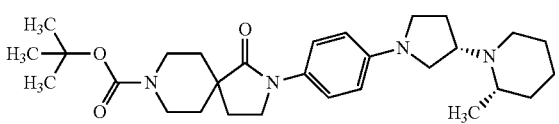 [SMILES: C[C@H]1CCCCN1[C@H]1CCN(c2ccc(N3CCC4(CCN(C(=O)OC(C)(C)C)CC4)C3=O)cc2)C1]

The title compound was prepared in a manner substantially the same as Example 1.

LC $R_T$=2.74 min, MS: 497 (M+H).

$^1$H NMR (300 MHz, CDCl$_3$) δ (ppm): 7.37 (d, 2H), 6.47 (d, 2H), 3.93 (d, 2H), 3.66 (t, 2H), 3.52 (t, 1H), 3.43-3.30 (m, 2H), 3.19 (dd, 2H), 2.96 (t, 1H), 2.79 (m, 1H), 2.62 (m, 1H), 2.31 (m, 1H), 2.01-1.82 (m, 7H), 1.67 (m, 1H), 1.58 (d, 2H), 1.50-1.30 (m, 13H), 1.10 (d, 3H).

Example 42

2-{4-[3-((2S,3'S)-2-Methyl-piperidin-1-yl)-pyrrolidin-1-yl]-2-trifluoromethyl-phenyl}-1-oxo-2,8-diaza-spiro[4.5]decane-8-carboxylic acid tert-butyl ester

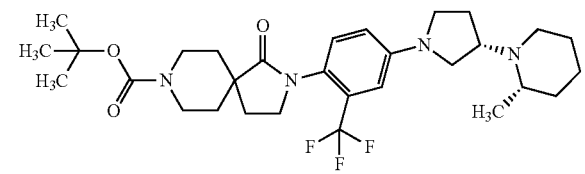 [SMILES: C[C@H]1CCCCN1[C@H]1CCN(c2ccc(N3CCC4(CCN(C(=O)OC(C)(C)C)CC4)C3=O)c(C(F)(F)F)c2)C1]

The title compound was prepared in a manner substantially the same as Example 1.

LC $R_T$=2.97 min, MS: 565 (M+H).

$^1$H NMR (300 MHz, CDCl$_3$) δ (ppm): 7.05 (d, 1H), 6.76 (d, 1H), 6.63 (dd, 1H), 3.98 (d, 2H), 3.66-3.40 (m, 5H), 3.32 (t, 1H), 3.23 (dd, 1H), 3.11 (t, 2H), 2.88 (m, 1H), 2.69 (m, 1H), 2.38 (m, 1H), 2.10-2.00 (m, 4H), 1.98-1.94 (m, 2H), 1.78-1.70 (m, 1H), 1.60-1.40 (m, 13H), 1.08 9d, 3H).

Example 43

2-{4-[3-((2S,3'S)-2-Methyl-piperidin-1-yl)-pyrrolidin-1-yl]-2-fluoro-phenyl}-1-oxo-2,8-diaza-spiro[4.5]decane-8-carboxylic acid tert-butyl ester

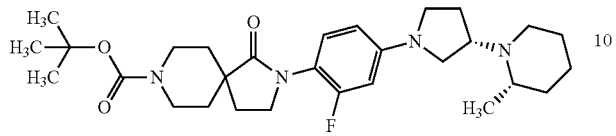

The title compound was prepared in a manner substantially the same as Example 1.

LC $R_T$=2.66 min, MS: 515 (M+H).

$^1$H NMR (300 MHz, CDCl$_3$) δ (ppm): 7.14 (t, 1H), 6.26-6.23 (m, 2H), 3.99 (d, 2H), 3.65 (t, 2H), 3.58 (dd, 1H), 3.49-3.34 (m, 2H), 3.30-3.04 (m, 4H), 2.86 (m, 1H), 2.65 (m, 1H), 2.36 (m, 1H), 2.11-1.93 (m, 7H), 1.78 (m, 1H), 1.65-1.43 (m, 15), 1.10 (d, 3H).

Example 44

2-{4-[4-(2S-2-Methyl-pyrrolidin-1-yl)-piperidin-1-yl]-phenyl}-2,8-diaza-spiro[4.5]decan-1-one Hydrochloride

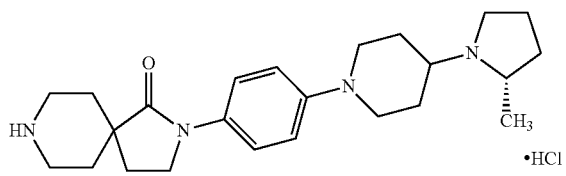 [SMILES: C[C@H]1CCCN1C1CCN(c2ccc(N3CCC4(CCNCC4)C3=O)cc2)CC1 ; Cl]

The title compound was prepared in a manner substantially the same as Example 1.

LC $R_T$=2.43 min, MS: 397 (M+H).

$^1$H NMR (300 MHz, CD$_3$OD) δ (ppm): 7.86 (d, 2H), 7.73 (d, 2H), 3.93-3.84 (m, 5H), 3.67 (m, 2H), 3.60-3.56 (m, 2H), 2.50-2.35 (m, 4H), 2.24 (t, 2H), 2.13-2.09 (m, 4H), 1.88-1.80 (m, 4H), 1.53 (d, 3H).

Example 45

2-{4-[4-(2S-2-Methyl-pyrrolidin-1-yl)-piperidin-1-yl]-2-trifluoromethyl-phenyl}-2,8-diaza-spiro[4.5]decan-1-one Hydrochloride

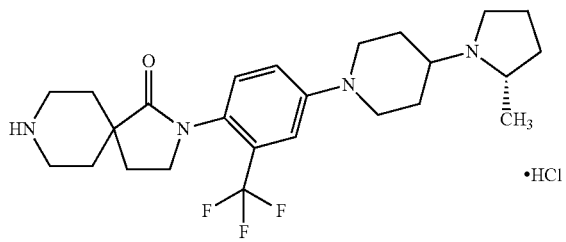 [SMILES: C[C@H]1CCCN1C1CCN(c2ccc(N3CCC4(CCNCC4)C3=O)c(C(F)(F)F)c2)CC1 ; Cl]

The title compound was prepared in a manner substantially the same as Example 1.

LC $R_T$=1.89 min, MS: 465 (M+H).

$^1$H NMR (300 MHz, CD$_3$OD) δ (ppm): 7.57 (d, 2H), 7.44 (d, 1), 4.01 (d, 2H), 3.83 (m, 1H), 3.73 (t, 2H), 3.61-3.50 (m, 4H), 3.25-3.20 (m, 4H), 2.33-2.25 (m, 5H), 2.12-2.08 (m, 5H), 1.93-1.75 (m, 4H), 1.50 (d, 3H).

Example 46

2-{4-[4-(2S-2-Methyl-pyrrolidin-1-yl)-piperidin-1-yl]-2-fluoro-phenyl}-2,8-diaza-spiro[4.5]decan-1-one Hydrochloride

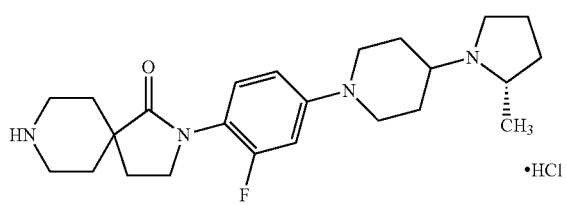 [SMILES: C[C@H]1CCCN1C1CCN(c2ccc(N3CCC4(CCNCC4)C3=O)c(F)c2)CC1 ; Cl]

The title compound was prepared in a manner substantially the same as Example 1.

LC $R_T$=3.19 min, MS: 415 (M+H).

$^1$H NMR (300 MHz, CD$_3$OD) δ (ppm): 7.34 (t, 1H), 7.06 (dd, 2H), 3.91 (d, 2H), 3.86-3.80 (m, 1H), 3.75 (t, 2H), 3.60-3.49 (m, 5H), 3.26-3.21 (m, 2H), 3.18-3.10 (m, 2H), 2.35-2.23 (m, 4H), 2.18-1.78 (m, 8H), 1.53 (d, 3H).

Example 47

2-{4-[3-((2S,3'S)-2-Methyl-piperidin-1-yl)-pyrrolidin-1-yl]-phenyl}-2,8-diaza-spiro[4.5]decan-1-one Hydrochloride

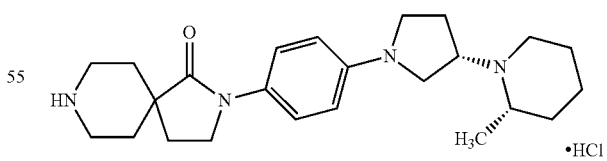

The title compound was prepared in a manner substantially the same as Example 1.

LC $R_T$=2.56 min, MS: 397 (M+H).

$^1$H NMR (300 MHz, CD$_3$OD) δ (ppm): 7.42 (dd, 2H), 6.72 (t, 2H), 3.84 (m, 3H), 3.61-3.49 (m, 6H), 3.24-3.19 (m, 3H), 2.47 (dd, 1H), 2.20 (t, 3H), 2.18-2.07 (m, 3H), 1.95-1.88 (m, 6H), 1.79-1.68 (m, 3H), 1.47 (t, 3H).

Example 48

2-{4-[3-((2S,3'S)-2-Methyl-piperidin-1-yl)-pyrrolidin-1-yl]-2-trifluoromethyl-phenyl}-2,8-diaza-spiro[4.5]decan-1-one Hydrochloride

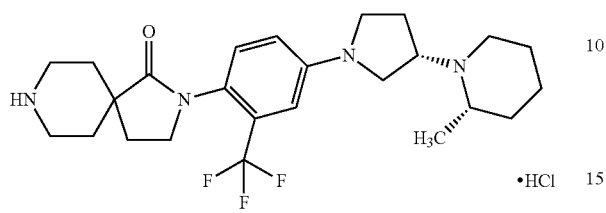

The title compound was prepared in a manner substantially the same as Example 1.
LC $R_T$=2.9 min, MS: 465 (M+H).
$^1$H NMR (300 MHz, CD$_3$OD) δ (ppm): 7.27 (dd, 1H), 6.94 (d, 2H), 3.75-2.68 (m, 3H), 3.60-3.48 (m, 6H), 3.24-3.20 (m, 3H), 2.51 (dd, 1H), 2.25 (t, 3H), 2.15-2.07 (m, 3H), 1.92-1.79 (m, 7H), 1.70-1.63 (m, 3H), 1.48 (t, 3H).

Example 49

2-{4-[3-((2S,3'S)-2-Methyl-piperidin-1-yl)-pyrrolidin-1-yl]-2-fluoro-phenyl}-2,8-diaza-spiro[4.5]decan-1-one Hydrochloride

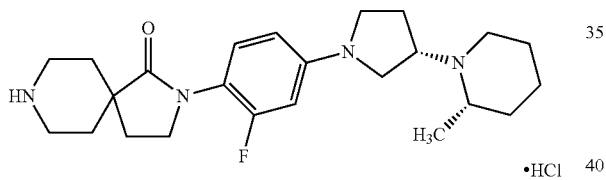

The title compound was prepared in a manner substantially the same as Example 1.
LC $R_T$=2.61 min, MS: 415 (M+H).
$^1$H NMR (300 MHz, CD$_3$OD) δ (ppm): 7.23-7.19 (m, 1H), 6.51 (t, 2H), 3.76-3.70 (m, 3H), 3.61-3.51 (m, 6H), 3.25-3.21 (m, 3H), 2.48 (m, 1H), 2.26-2.20 (m, 3H), 2.17-2.09 (m, 3H), 1.91-1.76 (m, 7H), 1.68-1.60 (m, 3H), 1.47 (t, 3H).

Example 50

8-Benzenesulfonyl-2-{4-[4-(2S-2-methyl-pyrrolidin-1-yl)-piperidin-1-yl]-phenyl}-2,8-diaza-spiro[4.5]decan-1-one

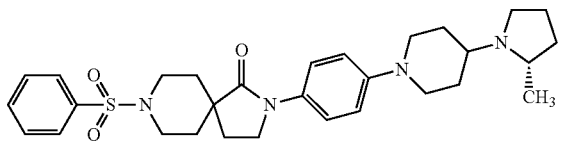 [SMILES: C[C@H]1CCCN1C1CCN(c2ccc(N3CCC4(CCN(S(=O)(=O)c5ccccc5)CC4)C3=O)cc2)CC1]

The title compound was prepared in a manner substantially the same as Example 1.
LC $R_T$=4.99 min, MS: 537 (M+H).
$^1$H NMR (300 MHz, CD$_3$OD) δ (ppm): 7.79 (d, 2H), 7.69-7.60 (m, 3H), 7.38 (d, 2H), 7.01 (d, 2H), 3.85-3.80 (m, 3H), 3.74 (t, 1H), 3.68-3.64 (m, 3H), 3.25-3.20 (m, 3H), 2.79 (t, 2H), 2.66 (t, 2H), 2.28-1.80 (m, 14H), 1.65 (m, 1H), 1.47 (d, 3H).

Example 51

8-(4-Fluoro-benzoyl)-2-{4-[4-(2S-2-methyl-pyrrolidin-1-yl)-piperidin-1-yl]-phenyl}-2,8-diaza-spiro[4.5]decan-1-one

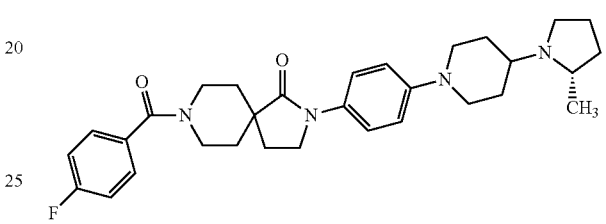

The title compound was prepared in a manner substantially the same as Example 1.
LC $R_T$=4.59 min, MS: 519 (M+H).
$^1$H NMR (300 MHz, CD$_3$OD) δ (ppm): 7.52-7.44 (m, 4H), 7.21 (t, 2H), 7.03 (d, 2H), 3.86-3.82 (m, 6H), 3.48-3.30 (m, 3H), 3.2 (m, 3H), 2.8 (t, 2H), 2.35-1.98 (m, 8H), 1.90-1.77 (m, 6H), 1.45 (d, 3H).

Example 52

8-Cyclohexanecarbonyl-2-{2-fluoro-4-[4-(2S-2-methyl-pyrrolidin-1-yl)-piperidin-1-yl]-phenyl}-2,8-diaza-spiro[4.5]decan-1-one

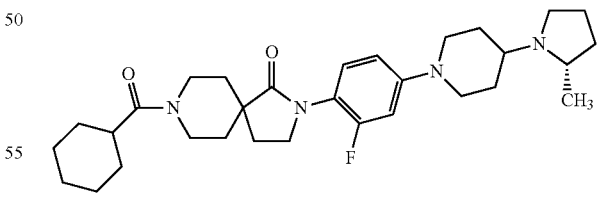

The title compound was prepared in a manner substantially the same as Example 1.
LC $R_T$=4.96 min, MS: 525 (M+H).
$^1$H NMR (300 MHz, CD$_3$OD) δ (ppm): 7.20 (t, 1H), 6.81 (d, 2H), 4.35-4.30 (m, 1H), 4.05-4.00 (m, 1H), 3.94-3.86 (m, 4H), 3.73 (t, 3H), 3.51-3.42 (m, 3H), 3.17-3.08 (m, 1H), 2.91-2.83 (m, 3H), 2.68 (m, 1H), 2.32-2.19 (m, 5H), 2.11-2.04 (m, 4H), 1.89-160 (m, 13H) 1.44 (d, 3H).

Example 53

8-(4-Fluoro-benzenesulfonyl)-2-{4-[3-((2S,3'S)-2-methyl-piperidin-1-yl)-pyrrolidin-1-yl]-phenyl}-2,8-diaza-spiro[4.5]decan-1-one

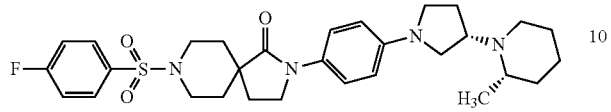

The title compound was prepared in a manner substantially the same as Example 1.
LC $R_T$=5.3 min, MS: 555 (M+H).
$^1$H NMR (300 MHz, CD$_3$OD) δ (ppm): 7.88-7.84 (m, 2H), 7.42-7.33 (m, 4H), 6.67 (d, 2H), 4.30-4.26 (m, 1H), 3.75 (t, 2H), 3.67-3.56 (m, 6H), 3.38-3.33 (m, 2H), 2.69 (t, 2H), 2.48-2.32 (m, 4H), 2.06-1.78 (m, 8H), 1.75 (m, 3H), 1.45 (d, 3H).

Example 54

2-{4-[3-((2S,3'S)-2-Methyl-piperidin-1-yl)-pyrrolidin-1-yl]-phenyl}-8-(tetrahydro-pyran-4-carbonyl)-2,8-diaza-spiro[4.5]decan-1-one

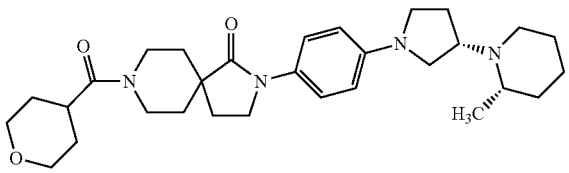 [SMILES: C[C@H]1CCCCN1[C@H]1CCN(c2ccc(N3CCC4(CCN(C(=O)C5CCOCC5)CC4)C3=O)cc2)C1]

The title compound was prepared in a manner substantially the same as Example 1.
LC $R_T$=4.26 min, MS: 509 (M+H).
$^1$H NMR (300 MHz, CD$_3$OD) δ (ppm): 7.39 (d, 2H), 6.67 (d, 2H), 4.39 (m, 1H), 4.15 (m, 1H), 3.97 (m, 2H), 3.83 (t, 2H), 3.66-3.47 (m, 7H), 3.03-2.98 (m, 3H), 2.5-2.35 (m, 2H) 2.21 (t, 2H), 2.10-2.00 (m, 1H), 1.88-1.79 (m, 10H), 1.65-1.60 (m, 6H), 1.45 (d, 3H).

Example 55

8-Cyclopentanecarbonyl-2-{4-[3-((2S,3'S)-2-methyl-piperidin-1-yl)-pyrrolidin-1-yl]-2-trifluoromethyl-phenyl}-2,8-diaza-spiro[4.5]decan-1-one

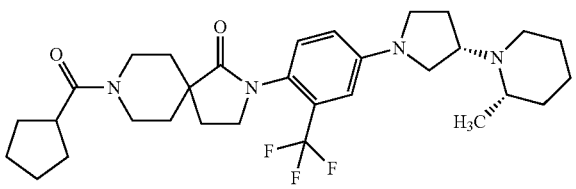 [SMILES: C[C@H]1CCCCN1[C@H]1CCN(c2ccc(N3CCC4(CCN(C(=O)C5CCCC5)CC4)C3=O)c(C(F)(F)F)c2)C1]

The title compound was prepared in a manner substantially the same as Example 1.
LC $R_T$=5.24 min, MS: 561 (M+H).
$^1$H NMR (300 MHz, CD$_3$OD) δ (ppm): 7.21 (d, 1H), 6.93 (m, 2H), 4.38-4.28 (m, 1H), 4.10-4.06 (m, 1H), 3.79-3.63 (m, 8H), 3.43-3.40 (m, 3H), 2.50-2.50 (m, 2H), 2.25 (m, 2H), 2.07 (m, 2H), 1.88-1.64 (m, 15H), 1.47 (d, 3H).

Example 56

8-Cyclopropylmethyl-2-{2-fluoro-4-[4-(2S-2-methyl-pyrrolidin-1-yl)-piperidin-1-yl]-phenyl}-2,8-diaza-spiro[4.5]decan-1-one

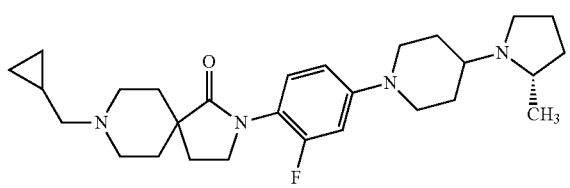 [SMILES: C[C@H]1CCCN1C1CCN(c2ccc(N3CCC4(CCN(CC5CC5)CC4)C3=O)c(F)c2)CC1]

The title compound was prepared in a manner substantially the same as Example 1.
LC $R_T$=1.92 min, MS: 469 (M+H).
$^1$H NMR (300 MHz, CD$_3$OD) δ (ppm): 7.22 (t, 1H), 6.85 (d, 2H), 3.94-3.82 (m, 3H), 3.77-3.70 (t, 2H), 3.68-3.60 (m, 2H), 3.53-3.42 (m, 2H), 3.36 (s, 2H), 3.27-3.19 (m, 2H), 3.02 (d, 2H), 2.91-2.83 (m, 2H), 2.32-1.79 (m, 13H), 1.43 (d, 3H), 1.10-1.06 (m, 1H), 0.75 (s, 2H), 0.43 (d, 2H).

Example 57

8-Cyclopentyl methyl-2-{2-fluoro-4-[4-(2S-2-methyl-pyrrolidin-1-yl)-piperidin-1-yl]-phenyl}-2,8-diaza-spiro[4.5]decan-1-one

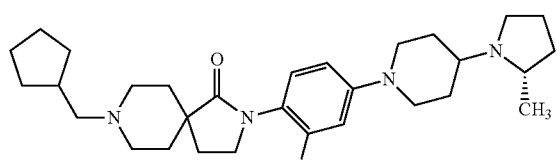

The title compound was prepared in a manner substantially the same as Example 1.
LC $R_T$=3.91 min, MS: 497 (M+H).
$^1$H NMR (300 MHz, CD$_3$OD) δ (ppm): 7.21 (t, 1H), 6.82 (d, 2H), 3.86 (d, 2H), 3.70 (t, 2H), 3.67-3.54 (m, 1H), 3.34 (s, 2H), 3.23 (m, 1H), 3.18-3.09 (m, 4H), 2.88-2.78 (m, 2H), 2.57-2.39 (m, 4H), 2.20-1.45 (m, 20H), 1.40-1.17 (m, 5H).

Example 58

8-Cyclohexyl methyl-2-{4-[3-((2S,3'S)-2-methyl-piperidin-1-yl]-pyrrolidin-1-yl]-2-trifluoromethyl-phenyl}-2,8-diaza-spiro[4.5]decan-1-one

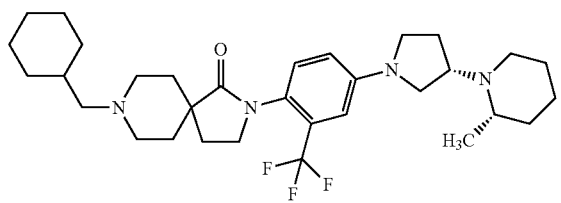 [SMILES: C[C@H]1CCCCN1[C@H]1CCN(c2ccc(N3CCC4(CCN(CC5CCCCC5)CC4)C3=O)c(C(F)(F)F)c2)C1]

The title compound was prepared in a manner substantially the same as Example 1.

LC $R_T$=4.41 min, MS: 561 (M+H).

$^1$H NMR (300 MHz, CD$_3$OD) δ (ppm): 7.11 (d, 1H), 6.81 (m, 2H), 3.65-3.62 (m, 3H), 3.60-3.46 (m, 2H), 3.35 (s, 2H), 3.25 (m, 1H), 2.92-2.84 (m, 4H), 2.71 (m, 1H), 2.46 (m, 1H), 2.19-2.08 (m, 8H), 2.01-1.94 (m, 2H), 1.82-1.45 (m, 13H), 1.35-1.24 (m, 2H), 1.15 (d, 3H), 0.93 (dd, 2H).

Example 59

2-{2-Fluoro-4-[3-((2S,3'S)-2-methyl-piperidin-1-yl)-pyrrolidin-1-yl]-phenyl}-8-(tetrahydro-pyran-4-ylmethyl)-2,8-diaza-spiro[4.5]decan-1-one

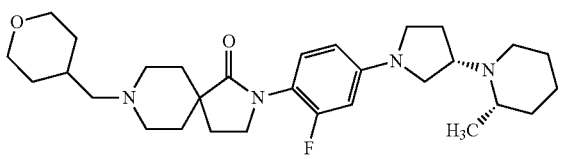 [SMILES: C[C@H]1CCCCN1[C@H]1CCN(c2ccc(N3CCC4(CCN(CC5CCOCC5)CC4)C3=O)c(F)c2)C1]

The title compound was prepared in a manner substantially the same as Example 1.

LC $R_T$=3.61 min, MS: 513 (M+H).

$^1$H NMR (300 MHz, CD$_3$OD) δ (ppm): 7.08 (t, 1H), 6.40-6.32 (m, 2H), 3.95-3.90 (m, 2H), 3.68-3.58 (m, 3H), 3.51-3.34 (m, 4H), 3.33 (s, 2H), 3.25 (m, 1H), 2.89 (d, 4H), 2.69 (m, 1H), 2.45 (m, 1H), 2.22-1.90 (m, 11H), 1.89-1.40 (m, 8H), 1.38-1.20 (m, 2H), 1.15 (d, 3H).

Example 60

2-[4-((2S,3'S)-2-Methyl-[1,3']bipyrrolidinyl-1'-yl)-2-trifluoromethyl-phenyl]-8-phenylacetyl-2,8-diaza-spiro[4.5]decan-1-one

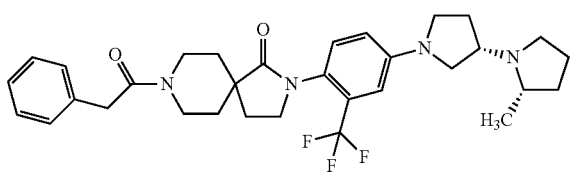 [SMILES: C[C@H]1CCCN1[C@H]1CCN(c2ccc(N3CCC4(CCN(C(=O)Cc5ccccc5)CC4)C3=O)c(C(F)(F)F)c2)C1]

The title compound was prepared in a manner substantially the same as Example 1.

LC $R_T$=3.01 min, MS: 569 (M+H).

$^1$H NMR (300 MHz, CDCl$_3$) δ (ppm): 7.98-7.91 (m, 4H), 7.60-7.50 (m, 3H), 7.17 (d, 1H), 6.82-6.80 (m, 2H), 4.48 (m, 1H), 3.81 (m, 1H), 3.67 (m, 2H), 3.58 (t, 1H), 3.46-3.34 (m, 4H), 3.27-3.21 (m, 2H), 3.04-2.97 (m, 1H), 2.92-2.82 (q, 2H), 2.65 (q, 1H), 2.25 (m, 2H), 2.10-1.95 (m, 3H), 1.83-1.78 (m, 3H), 1.68-1.40 (m, 3H), 1.18 (d, 3H).

Example 61

8-(2-Methoxy-acetyl)-2-[4-((2S,3'S)-2-methyl-[1,3']bipyrrolidinyl-1'-yl)-2-trifluoromethyl-phenyl]-2,8-diaza-spiro[4.5]decan-1-one

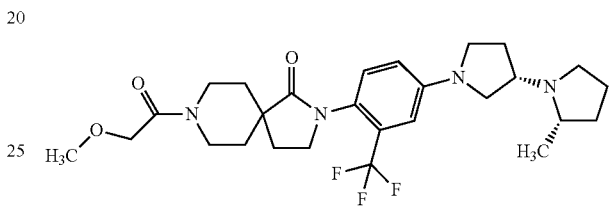

The title compound was prepared in a manner substantially the same as Example 1.

LC $R_T$=4.31 min, MS: 523 (M+H).

$^1$H NMR (300 MHz, CDCl$_3$) δ (ppm): 7.21 (d, 1H), 6.90 (d, 2H), 4.30 (m, 1H), 4.21 (d, 2H), 4.05-3.97 (m, 1H), 3.93-3.75 (m, 2H), 3.69 (t, 2H), 3.61-3.57 (m, 2H), 3.41 (s, 3H), 3.36-3.33 (m, 2H), 3.22-3.15 (m, 2H), 2.53-2.45 (m, 1H), 2.27-2.24 (m, 5H), 2.10-2.04 (m, 2H), 1.95-1.65 (m, 6H), 1.42 (d, 3H).

Example 62

2-[4-((2S,3'S)-2-Methyl-[1,3']bipyrrolidinyl-1'-yl)-2-trifluoromethyl-phenyl]-8-(naphthalene-2-carbonyl)-2,8-diaza-spiro[4.5]decan-1-one

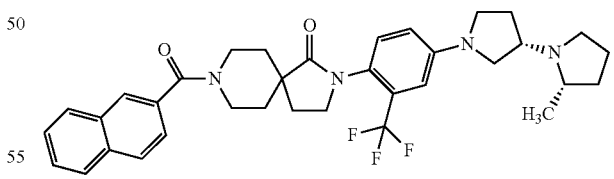

The title compound was prepared in a manner substantially the same as Example 1.

LC $R_T$=3.21 min, MS: 605 (M+H).

$^1$H NMR (300 MHz, CDCl$_3$) δ (ppm): 7.98-7.91 (m, 4H), 7.60-7.50 (m, 3H), 7.17 (d, 1H), 6.82-6.80 (m, 2H), 4.48 (m, 1H), 3.81 (m, 1H), 3.67 (m, 2H), 3.58 (t, 1H), 3.46-3.34 (m, 4H), 3.27-3.21 (m, 2H), 3.04-2.97 (m, 1H), 2.92-2.82 (q, 2H), 2.65 (q, 1H), 2.25 (m, 2H), 2.10-1.95 (m, 3H), 1.83-1.78 (m, 3H), 1.68-1.40 (m, 3H), 1.18 (d, 3H).

Example 63

8-Benzoyl-2-[4-((2S,3'S)-2-methyl-[1,3']bipyrrolidinyl-1'-yl)-2-trifluoromethyl-phenyl]-2,8-diaza-spiro[4.5]decan-1-one

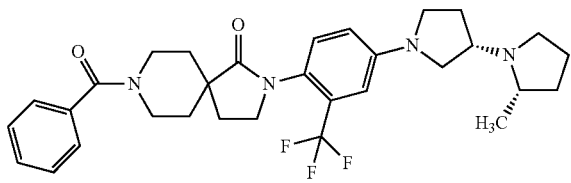 [SMILES: C[C@H]1CCCN1[C@H]1CCN(c2ccc(N3CCC4(CCN(C(=O)c5ccccc5)CC4)C3=O)c(C(F)(F)F)c2)C1]

The title compound was prepared in a manner substantially the same as Example 1.

LC $R_T$=2.93 min, MS: 555 (M+H).

$^1$H NMR (300 MHz, CD$_3$OD) δ (ppm): 7.49-7.44 (m, 5H), 7.21 (d, 2), 6.93 (m, 2H), 4.42 (m, 1H), 4.16-4.11 (m, 1H), 3.83-3.54 (m, 6H), 3.38-3.34 (m, 2H), 3.24-3.20 (m, 2H), 2.60-2.53 (m, 2H), 2.36-2.22 (m, 5H), 2.15-2.10 (m, 3H), 1.97-1.78 (m, 4H), 1.47 (d, 3H).

Example 64

8-(Furan-3-carbonyl)-2-[4-((2S,3'S)-2-methyl-[1,3']bipyrrolidinyl-1'-yl)-2-trifluoromethyl-phenyl]-2,8-diaza-spiro[4.5]decan-1-one

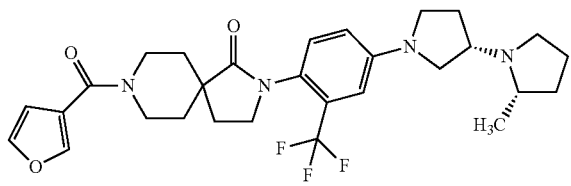 [SMILES: C[C@H]1CCCN1[C@H]1CCN(c2ccc(N3CCC4(CCN(C(=O)c5ccoc5)CC4)C3=O)c(C(F)(F)F)c2)C1]

The title compound was prepared in a manner substantially the same as Example 1.

LC $R_T$=2.75 min, MS: 545 (M+H).

$^1$H NMR (300 MHz, CDCl$_3$) δ (ppm): 7.88 (s, 1H), 7.60 (s, 1H), 7.21 (d, 1H), 6.87 (s, 2H), 6.64 (s, 1H), 4.38-4.06 (m, 2H), 3.82-3.66 (m, 4H), 3.58-3.52 (m, 1H), 3.43-3.33 (m, 5H), 3.01-2.92 (q, 1H), 2.39-2.28 (m, 1H), 2.26-2.05 (m, 5H), 1.99-1.80 (m, 4H), 1.74-1.60 (m, 3H), 1.35 (d, 3H).

Example 65

8-(4-Methoxy-benzenesulfonyl)-2-[4-((2S,3'S)-2-methyl-[1,3']bipyrrolidinyl-1'-yl)-2-trifluoromethyl-phenyl]-2,8-diaza-spiro[4.5]decan-1-one

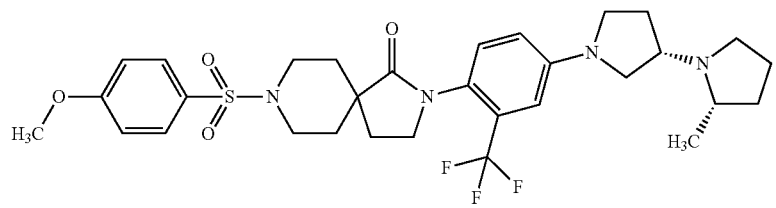 [SMILES: COc1ccc(S(=O)(=O)N2CCC3(CCN(c4ccc(N5CC[C@H](N6CCC[C@@H]6C)C5)cc4C(F)(F)F)C3=O)CC2)cc1]

The title compound was prepared in a manner substantially the same as Example 1.

LC $R_T$=3.19 min, MS: 621 (M+H).

$^1$H NMR (300 MHz, CD$_3$OD) δ (ppm): 7.74 (d, 2H), 7.18-7.04 (m, 3H), 6.89 (m, 2H), 4.02 (m, 1H), 3.88 (s, 3H), 3.78-3.72 (m, 1H), 3.63-3.55 (m, 8H), 3.23 (m, 2H), 2.75-2.68 (m, 2H), 2.54-2.48 (m, 1H), 2.35-2.29 (m, 2H), 2.10-1.95 (m, 6H), 1.80-1.65 (m, 3H), 1.45 (d, 3H).

Example 66

8-Furan-2-ylmethyl-2-[4-((2S,3'S)-2-methyl-[1,3']bipyrrolidinyl-1'-yl)-2-trifluoromethyl-phenyl]-2,8-diaza-spiro[4.5]decan-1-one

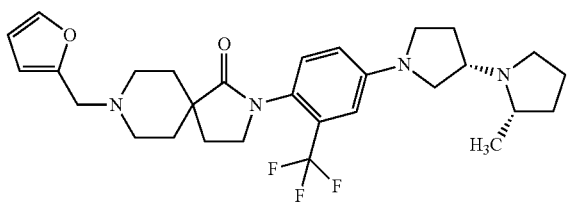 [SMILES: C[C@H]1CCCN1[C@H]1CCN(c2ccc(N3CCC4(CCN(Cc5ccco5)CC4)C3=O)c(C(F)(F)F)c2)C1]

The title compound was prepared in a manner substantially the same as Example 1.

LC $R_T$=2.22 min, MS: 531 (M+H).

$^1$H NMR (300 MHz, CDCl$_3$) δ (ppm): 7.56 (s, 1H), 7.23 (d, 1H), 6.93 (d, 2H), 6.50 (s, 1H), 6.44 (s, 1H), 4.09-4.07 (m, 1H), 3.95-3.93 (s, 2H), 3.81-3.49 (m, 8H), 3.19-3.15 (m, 2H), 2.74-2.68 (m, 2H), 2.54-2.49 (m, 2H), 2.36-2.17 (m, 4H), 2.15-2.07 (m, 4H), 1.82-1.74 (m, 3H), 1.47 (d, 3H).

Example 67

8-Cyclopropylmethyl-2-[4-((2S,3'S)-2-methyl-[1,3']bipyrrolidinyl-1'-yl)-2-trifluoromethyl-phenyl]-2,8-diaza-spiro[4.5]decan-1-one

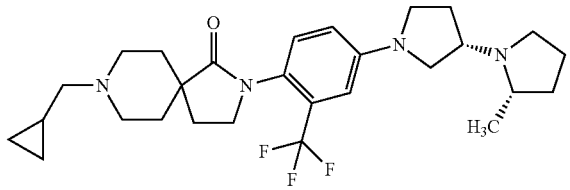 [SMILES: C[C@H]1CCCN1[C@H]1CCN(c2ccc(N3CCC4(CCN(CC5CC5)CC4)C3=O)c(C(F)(F)F)c2)C1]

The title compound was prepared in a manner substantially the same as Example 1.

LC $R_T$=3.72 min, MS: 505 (M+H).

¹H NMR (300 MHz, CD₃OD) δ (ppm): 7.29 (d, 1H), 6.94 (d, 2H), 4.15-4.10 (m, 1H), 3.80-3.53 (m, 8H), 3.40-3.33 (m, 2H), 3.04 (d, 2H), 2.55 (m, 2H), 2.39-2.17 (m, 6H), 2.13 (t, 1H), 2.08-2.00 (m, 3H), 1.83-1.76 (m, 1H), 1.47 (d, 3H), 1.2-1.15 (m, 1H), 0.79 (d, 2H), 0.49 (d, 2H).

Example 68

2-[4-((2S,3'S)-2-Methyl-[1,3']bipyrrolidinyl-1'-yl)-2-trifluoromethyl-phenyl]-8-(tetrahydro-pyran-4-ylmethyl)-2,8-diaza-spiro[4.5]decan-1-one

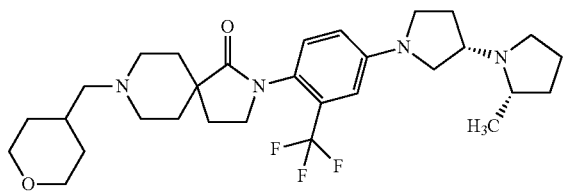 [SMILES: C[C@H]1CCCN1[C@H]1CCN(c2ccc(N3CCC4(CCN(CC5CCOCC5)CC4)C3=O)c(C(F)(F)F)c2)C1]

The title compound was prepared in a manner substantially the same as Example 1.

LC R$_T$=3.68 min, MS: 549 (M+H).

¹H NMR (300 MHz, CD₃OD) δ (ppm): 7.29 (d, 1H), 6.96 (d, 2H), 4.17 (m, 2H), 3.97-3.93 (d, 4H), 3.85-3.77 (m, 2H), 3.72-3.32 (m, 8H), 3.25-3.22 (m, 2H), 3.03 (d, 2H), 2.59-2.53 (m, 1), 2.38-2.11 (m, 8H), 2.08-1.95 (m, 2H), 1.83-1.74 (m, 4H), 1.44 (d, 3H), 1.44-1.35 (m, 2H).

Example 69

2-[4-((2S,3'S)-2-Methyl-[1,3']bipyrrolidinyl-1'-yl)-2-trifluoromethyl-phenyl]-2,8-diaza-spiro[4.5]decan-1-one Hydrochloride

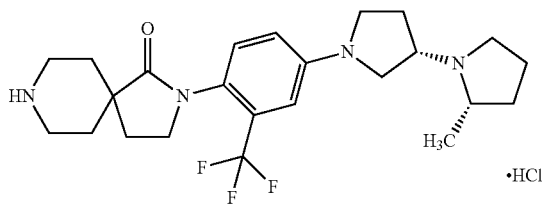 [SMILES: C[C@H]1CCCN1[C@H]1CCN(c2ccc(N3CCC4(CCNCC4)C3=O)c(C(F)(F)F)c2)C1 ; Cl]

The title compound was prepared in a manner substantially the same as Example 1.

LC R$_T$=3.4 min, MS: 451 (M+H).

¹H NMR (300 MHz, CD₃OD) δ (ppm): 7.6 (d, 1H), 6.95 (m, 2H), 4.24-4.21 (m, 1H), 3.86-3.80 (m, 1H), 3.75-3.67 (m, 3H), 3.56-3.48 (m, 3H), 3.40-3.34 (m, 2H), 3.26-3.21 (m, 2H), 2.63-2.57 (m, 1H), 2.42-2.23 (m, 5H), 2.15-2.08 (m, 4H), 1.91-1.81 (m, 4H), 1.52 (d, 3H).

Biological Examples

Example 70

This Example 70 demonstrates the efficacy of the compounds of this invention as H3 receptor ligands. The compounds of this invention have been demonstrated to displace [³H]-methylhistamine radioligand binding to mammalian cell membranes expressing rhesus (Macacca Mulatta) H3 receptor. These compounds display rhesus H3 affinity constants (Ki) in the range of 1 µM to <1 nM. Additionally, the compounds of this invention have been demonstrated by GTPγS radioligand binding assay to inhibit rhesus H3 constitutive functional activity in cell membranes. This inhibition of basal rhesus H3-mediated GTPγS radioligand binding demonstrates that the compounds of this invention find utility as inverse agonists. These compounds decreased rhesus H3 GTPγS radioligand binding by 0-40% below basal levels.

Rhesus H3 membranes were prepared from the Flp-In T-REx 293 Cell Line (Invitrogen) stably transfected with pcDNA5/FRT/TO (Invitrogen) containing the rhesus monkey (Macacca Mulatta) 445 amino acid H3 receptor. (Genbank #AY231164). Stably transfected cultures were amplified in tissue culture flasks by standard tissue culture methods and induced to express rhesus H3 by exposure to 500 ng/ml tetracycline (Cellgro) for 24 hours. After induction, cells were dissociated from flasks utilizing Cell Stripper (Cellgro). Cells were centrifuged (1K×g, 5 min) and pellet frozen in an ethanol-dry ice bath to disrupt cell membranes. Frozen cell pellet was re-suspended in 5 mM HEPES (pH 7.4, Invitrogen) at 10 ml/1000 cm2 of harvested cells. The cell suspension was drawn through an 18 gauge needle (2-3×) followed by a 23 gauge needle (2-3×) to further disrupt cell membranes. The cell suspension was centrifuged (40K×g, 30 min). Cell membrane pellet was re-suspended in 5 mM HEPES (pH 7.4, Invitrogen) at a final protein concentration of 10 mg/ml. Rhesus H3 membranes were stored under liquid nitrogen prior to use in [3H]-Methylhistamine and GTP S radioligand binding assays.

Rhesus H3 radioligand binding assay was performed using rhesus H3 receptor membranes (prepared as described above), [3H]-Methylhistamine (Perkin Elmer) and WGA SPA beads (wheat germ agglutinin scintillation proximity assay) beads (Amersham). The assay was performed in 96-well Opti-Plates (Packard). Each reaction contained 50 µl rhesus H3 membranes (20-30 µg total protein), 50 µl WGA SPA beads (0.1 µg) and 50 µl of 83 Ci/mmol [³H]-Methylhistamine (final concentration 2 nM) and 50 µl of tested compound. The compounds of this invention and/or vehicle were diluted with binding buffer from 10 mM DMSO stocks. Assay plates were sealed with TopSeal (Perkin Elmer) and mixed on shaker (25° C., 1 hour). Assay plates were read on TopCount scintillation counter (Packard). Results were analyzed by Hill transformation and Ki values were determined by Cheng-Prusoff equation. The observed binding data for a few of the representative compounds of this invention are summarized in Table 1.

TABLE 1

| Example No. | Rhesus H3 binding ki (nM) | Inverse Agonism: % inhibition of Basal GTPγS binding in Rhesus H3 |
|---|---|---|
| 1 | 132 | −24 |
| 2 | 248 | −30 |
| 3 | 7 | −23 |
| 4 | 43 | −31 |
| 5 | 18 | −13 |
| 6 | 11 | −22 |
| 7 | 15 | −22 |
| 8 | 0.8 | −26 |
| 9 | 0.6 | −35 |
| 10 | 12 | −26 |
| 11 | 22 | −29 |
| 12 | 0.8 | −20 |
| 13 | 0.8 | −37 |
| 14 | 5.6 | −31 |
| 15 | 118 | −14 |

TABLE 1-continued

| Example No. | Rhesus H3 binding ki (nM) | Inverse Agonism: % inhibition of Basal GTPγS binding in Rhesus H3 |
|---|---|---|
| 16 | 100 | −13 |
| 17 | 1.4 | −9 |
| 18 | 6.2 | −10 |
| 19 | 1.4 | −19 |
| 20 | 6.8 | −18 |
| 21 | 7.3 | −28 |
| 22 | 0.03 | −27 |
| 23 | 0.07 | −19 |
| 24 | 0.1 | −13 |
| 25 | 0.06 | −22 |
| 26 | 4 | −17 |
| 27 | 1.6 | −19 |
| 28 | 0.5 | −15 |
| 29 | 0.4 | −17 |
| 30 | 0.7 | −22 |
| 31 | 0.4 | −19 |
| 32 | 0.4 | −14 |
| 33 | 0.2 | −14 |
| 34 | 0.2 | −16 |
| 35 | 0.04 | −18 |
| 36 | 0.06 | −13 |
| 37 | 0.1 | −17 |
| 38 | 0.008 | −25 |
| 39 | 0.9 | −22 |
| 40 | 0.3 | −21 |
| 41 | 5.6 | −14 |
| 42 | 64 | −15 |
| 43 | 4.3 | −19 |
| 44 | 0.1 | −19 |
| 45 | 0.15 | −19 |
| 46 | 0.1 | −24 |
| 47 | 0.4 | −17 |
| 48 | 0.6 | −24 |
| 49 | 0.5 | −22 |
| 50 | 0.24 | −23 |
| 51 | 0.08 | −17 |
| 52 | 0.2 | −24 |
| 53 | 1.9 | −13 |
| 54 | 3.3 | −24 |
| 55 | 2.1 | −27 |
| 56 | 0.04 | −23 |
| 57 | 0.1 | −21 |
| 58 | 0.15 | −19 |
| 59 | 4.6 | −19 |
| 60 | 144 | −19 |
| 61 | 193 | −7 |
| 62 | 8.1 | −19 |
| 63 | 64 | −18 |
| 64 | 9.6 | −19 |
| 65 | 10.6 | −18 |
| 66 | 5.5 | −19 |
| 67 | 1.4 | −12 |
| 68 | 4.2 | −19 |
| 69 | 0.09 | −28 |

Example 71

This Example illustrates the study of efficacy of the compounds of this invention in increasing the wakefulness in animal models.

Male Sprague Dawley rats (Charles River, France) weighing 250±10 g were anaesthetized with ZOLETIL$^R$ 50 (60 mg/kg ip) and mounted in a stereotaxic apparatus. Cortical electrodes (small stainless steel screw electrodes of 0.9 mm in diameter) were screwed into the bone over the sensorimotor cortex (1.5 mm lateral to the median suture and 1.5 mm behind the fronto-parietal suture), the visual cortex (1.5 mm lateral to the median suture and 1.5 mm in front of the parieto-occipital suture) and over the cerebellum (reference electrode). Cortical electrodes were attached to a connector (Winchester, 7-lead) and fixed with dental cement to the cranium.

After three weeks of post-operative recovery, animals were placed in plexiglass cylinders (60 cm diameter) with free access to food and water. The temperature of the room was kept constant (21±1° C.) and lights were on from 7 a.m. to 7 p.m. The rats were recorded from 10 a.m. to 4 p.m. during three consecutive days: control day (D1), drug day (D2) and post drug day (D3). Vehicle (D1 and D3) or drug (D2) were administered 15 min before the recording.

Activity in sensorimotor and visual cortices were recorded by comparison with the reference electrode placed over the cerebellar cortex. Three stages were differentiated:
  wakefulness (W) characterized by low voltage fast electrocortical (ECoG) activity;
  NREM sleep (non rapid eye movement or slow wave sleep: SWS) characterized by an increase in electrocortical activity; development of high-amplitude slow waves with some bursts of sleep spindles;
  REM sleep (rapid eye movement or paradoxical sleep: PS) characterized by hypersynchronization of the theta rhythm in the visual area.

Analysis of the ECoG signal was performed automatically by means of a computerized system discriminating between the various sleep phases using sequential spectral analysis of ten seconds periods (Deltamed's software "Coherence").

The compounds of this invention were dissolved in 0.6% MTC tween and administered by oral route (po). The volume of injection was 0.5 ml/100 g of body weight.

Two types of analysis were used to quantify the effects of the compounds of this invention on sleep-wakefulness variables: the one hour-period and the six hour-period analysis.

The results are expressed in minutes (one hour-period analysis) or as the percentage of the control values (100%). Statistical analysis of the data was carried out using the Student's t test for paired values to determine significant variations from control values.

Example 72

Stress-Induced Ultrasonic Vocalizations Test in Adult Rats

This Example illustrates the study of efficacy of the compounds of this invention as antidepressive agents in animal models.

The procedure used was adapted from the technique described by Van Der Poel A. M, Noach E. J. K, Miczek K. A (1989) Temporal patterning of ultrasonic distress calls in the adult rat: effects of morphine and benzodiazepines. Psychopharmacology 97:147-8. Rats were placed for a training session in a cage with a stainless steel grid floor (MED Associates, Inc., St. Albans, Vt.). Four electric shocks (0.8 mA, 3 s) were delivered every 7 s and ultrasonic vocalizations (UV, 22 KHz) were subsequently recorded with the Ultravox system (Noldus, Wageningen, The Netherlands) during 2 min. A modified ultrasound detector (Mini-3 bat model) connected to a microphone was used to transform ultrasonic sound into audible sound. The signal was then filtered and sent to a computer where the Ultravox software recorded each bout of UV that lasted more than 10 ms. Rats were selected on the basis of their UV duration (>40 s) and subjected to the test, 4 h after training. For the test, rats were placed in the same cage as that used for training. One electric shock (0.8 mA, 3 s) was delivered and UV (duration and frequency) were subsequently recorded with the Ultravox system during 2 min. The compounds of this invention were administered p.o. 60 min before testing.

Example 73

Forced-Swimming Test in Rats

This Example further illustrates the study of efficacy of the compounds of this invention as antidepressive agents in animal models.

The procedure was a modification of that described by Porsolt et al. (1977) Depression: a new animal model sensitive to antidepressant treatments. Nature 266:730-2. Rats were placed in individual glass cylinder (40 cm height, 17 cm diameter) containing water (21° C.) to a height of 30 cm. Two swimming sessions were conducted (a 15-min training session followed 24 h later by a 6-min test). After each swimming session, rats were placed under a heating lamp to avoid hypothermia. The duration of immobility was measured during the 6-min test. The compounds of this invention were administered p.o. twice (15 min after training session and 60 min before the test).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A method of modulating H3 receptor activity, comprising administering to a patient in need thereof a therapeutically effective amount of a compound of formula (I):

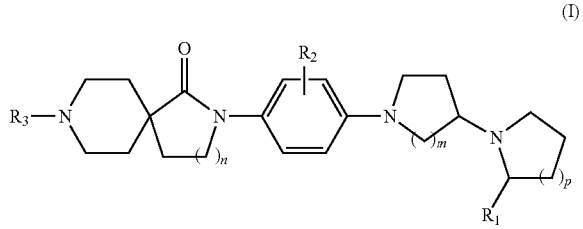

wherein
m is 1 or 2;
n is 1 or 2;
p is 1 or 2;
$R_1$ is hydrogen, $(C_1-C_4)$alkyl, $CF_3$, or $(C_1-C_4)$alkoxy-$(C_1-C_4)$alkyl;
$R_2$ is hydrogen, halogen, $(C_1-C_4)$alkyl or $CF_3$; and
$R_3$ is hydrogen, methoxyethylcarbonyl, tert-butyloxycarbonyl, cyclopropylmethyl, cyclopentylmethyl, cyclohexylmethyl, tetrahydropyranyl, benzyl, furanylmethyl, cyclopentane-carbonyl, cyclohexanecarbonyl, trifluoromethoxybenzoyl, fluorobenzoyl, benzyl-carbonyl, naphthylcarbonyl, benzenesulfonyl, fluorobenzene sulfonyl, methoxybenzenesulfonyl, isopropyl, tetrahydropyranylmethyl, tetrahydropyran carbonyl, benzoyl, pyridine carbonyl or furan carbonyl;
or a salt, enantiomer or diastereomer thereof.

2. The method according to claim 1, wherein for the compound of formula (I):
n, p, and m are 1;
$R_1$ is methyl, ethyl, isopropyl, n-propyl or methoxymethyl;
$R_2$ is hydrogen, fluorine, chlorine, methyl, ethyl or $CF_3$; and
$R_3$ is hydrogen, methoxyethylcarbonyl, tert-butyloxycarbonyl, cyclopropylmethyl, cyclopentylmethyl, cyclohexylmethyl, tetrahydropyranyl, benzyl, furanylmethyl, cyclopentane-carbonyl, cyclohexanecarbonyl, trifluoromethoxybenzoyl, fluorobenzoyl, benzyl-carbonyl, naphthylcarbonyl, benzenesulfonyl, fluorobenzene sulfonyl or methoxybenzenesulfonyl;
or a salt, enantiomer or diastereomer thereof.

3. The method according to claim 1, wherein for the compound of formula (I):
n is 2 and m is 1; or
n is 1 and m is 2;
p is 1 or 2;
$R_1$ is methyl or ethyl;
$R_2$ is hydrogen, fluorine, chlorine, methyl, ethyl or $CF_3$; and
$R_3$ is hydrogen, isopropyl, tert-butyloxycarbonyl, cyclopropylmethyl, cyclopentylmethyl, cyclohexylmethyl, tetrahydropyranyl, benzyl, furanylmethyl, tetrahydropyranylmethyl, cyclopentane carbonyl, cyclohexane carbonyl, tetrahydropyran carbonyl, benzoyl, trifluoromethoxybenzoyl, fluorobenzoyl, benzyl carbonyl, naphthyl carbonyl, pyridine carbonyl or furan carbonyl;
or a salt, enantiomer or diastereomer thereof.

4. The method according to claim 1, wherein the compound of formula (I) is selected from the group consisting of:
2-[2-methyl-4-((2R'S)-2-methyl-[1,3']bipyrrolidinyl-1'-yl)-phenyl]-1-oxo-2,8-diaza-spiro[4.5]decane-8-carboxylic acid tert-butyl ester;
2-[2-methyl-4-((2R,3'R)-2-methyl-[1,3']bipyrrolidinyl-1'-yl)-phenyl]-1-oxo-2,8-diaza-spiro[4.5]decane-8-carboxylic acid tert-butyl ester;
2-[2-methyl-4-((2S,3'R)-2-methyl-[1,3']bipyrrolidinyl-1'-yl)-phenyl]-1-oxo-2,8-diaza-spiro[4.5]decane-8-carboxylic acid tert-butyl ester;
2-[2-methyl-4-((2S,3'S)-2-methyl-[1,3']bipyrrolidinyl-1'-yl)-phenyl]-1-oxo-2,8-diaza-spiro[4.5]decane-8-carboxylic acid tert-butyl ester;
2-[2-methyl-4-(2-methyl-[1,3']bipyrrolidinyl-1'-yl)-phenyl]-1-oxo-2,8-diaza-spiro[4.5]decane-8-carboxylic acid tert-butyl ester;
2-[2-methyl-4-((2S,3'S)-2-methyl-[1,3']bipyrrolidinyl-1'-yl)-phenyl]-1-oxo-2,9-diaza-spiro[5.5]undecane-9-carboxylic acid tert-butyl ester;
2-[4-((2S,3'S)-2-methyl-[1,3']bipyrrolidinyl-1'-yl)-phenyl]-1-oxo-2,9-diaza-spiro[5.5]undecane-9-carboxylic acid tert-butyl ester;
4-{[2-fluoro-4-((2S,3'S)-2-methyl-[1,3']bipyrrolidinyl-1'-yl)-phenyl]-methyl-carbamoyl}-4-propyl-piperidine-1-carboxylic acid tert-butyl ester;
2-{4-[4-(2S-2-methyl-pyrrolidin-1-yl)-piperidin-1-yl]-phenyl}-1-oxo-2,8-diaza-spiro[4.5]decane-8-carboxylic acid tert-butyl ester;
2-{4-[4-(2S-2-methyl-pyrrolidin-1-yl)-piperidin-1-yl]-2-trifluoromethyl-phenyl}-1-oxo-2,8-diaza-spiro[4.5]decane-8-carboxylic acid tert-butyl ester;
2-{4-[4-(2S-2-methyl-pyrrolidin-1-yl)-piperidin-1-yl]-2-fluoro-phenyl}-1-oxo-2,8-diaza-spiro[4.5]decane-8-carboxylic acid tert-butyl ester;
2-{4-[3-((2S,3'S)-2-methyl-piperidin-1-yl)-pyrrolidin-1-yl]-phenyl}-1-oxo-2,8-diaza-spiro[4.5]decane-8-carboxylic acid tert-butyl ester;
2-{4-[3-((2S,3'S)-2-methyl-piperidin-1-yl)-pyrrolidin-1-yl]-2-trifluoromethyl-phenyl}-1-oxo-2,8-diaza-spiro[4.5]decane-8-carboxylic acid tert-butyl ester;
2-{4-[3-((2S,3'S)-2-methyl-piperidin-1-yl)-pyrrolidin-1-yl]-2-fluoro-phenyl}-1-oxo-2,8-diaza-spiro[4.5]decane-8-carboxylic acid tert-butyl ester;

2-[2-methyl-4-((2S,3'S)-2-methyl-[1,3']bipyrrolidinyl-1'-yl)-phenyl]-2,8-diaza-spiro[4.5]decan-1-one;
8-cyclopentylmethyl-2-[2-methyl-4-(2-methyl-[1,3']bipyrrolidinyl-1'-1)-phenyl]-2,8-diaza-spiro[4.5]decan-1-one;
2-[2-methyl-4-((2S,3'S)-2-methyl-[1,3']bipyrrolidinyl-1'-yl)-phenyl]-8-(4-trifluoromethoxy-benzoyl)-2,8-diaza-spiro[4.5]decan-1-one;
8-benzenesulfonyl-2-{4-[4-(2S-2-methyl-pyrrolidin-1-yl)-piperidin-1-yl]-phenyl}-2,8-diaza-spiro[4.5]decan-1-one;
8-(4-methoxy-benzenesulfonyl)-2-[4-((2S,3'S)-2-methyl-[1,3']bipyrrolidinyl-1'-yl)-2-trifluoromethyl-phenyl]-2,8-diaza-spiro[4.5]decan-1-one;
2-[4-((2S,3'S)-2-methyl-[1,3']bipyrrolidinyl-1'-yl)-2-trifluoromethyl-phenyl]-2,8-diaza-spiro[4.5]decan-1-one;
2-[2-methyl-4-((2S,3'S)-2-methyl-[1,3']bipyrrolidinyl-1'-yl)-phenyl]-2,8-diaza-spiro[4.5]decan-1-one;
2-[2-methyl-4-((2R,3'R)-2-methyl-[1,3']bipyrrolidinyl-1'-yl)-phenyl]-2,8-diaza-spiro[4.5]decan-1-one;
2-[2-methyl-4-((2R,3'S)-2-methyl-[1,3']bipyrrolidinyl-1'-yl)-phenyl]-2,8-diaza-spiro[4.5]decan-1-one;
2-[2-methyl-4-((2S,3'R)-2-methyl-[1,3']bipyrrolidinyl-1'-yl)-phenyl]-2,8-diaza-spiro[4.5]decan-1-one;
8-cyclopentylmethyl-2-[2-methyl-4-((2R,3'S)-2-methyl-[1,3']bipyrrolidinyl-1'-1)-phenyl]-2,8-diaza-spiro[4.5]decan-1-one;
8-cyclopentylmethyl-2-[2-methyl-4-((2R,3'R)-2-methyl-[1,3']bipyrrolidinyl-1'-1)-phenyl]-2,8-diaza-spiro[4.5]decan-1-one;
8-cyclopentylmethyl-2-[2-methyl-4-((2S,3'R)-2-methyl-[1,3']bipyrrolidinyl-1'-1)-phenyl]-2,8-diaza-spiro[4.5]decan-1-one;
8-cyclopentylmethyl-2-[2-methyl-4-((2S,3'S)-2-methyl-[1,3']bipyrrolidinyl-1'-1)-phenyl]-2,8-diaza-spiro[4.5]decan-1-one;
2-[2-methyl-4-((2R,3'S)-2-methyl-[1,3']bipyrrolidinyl-1'-yl)-phenyl]-8-(4-trifluoromethoxy-benzoyl)-2,8-diaza-spiro[4.5]decan-1-one;
2-[2-methyl-4-((2R,3'R)-2-methyl-[1,3']bipyrrolidinyl-1'-yl)-phenyl]-8-(4-trifluoromethoxy-benzoyl)-2,8-diaza-spiro[4.5]decan-1-one;
2-[2-methyl-4-((2S,3'R)-2-methyl-[1,3']bipyrrolidinyl-1'-yl)-phenyl]-8-(4-trifluoromethoxy-benzoyl)-2,8-diaza-spiro[4.5]decan-1-one;
2-[2-methyl-4-(2-methyl-[1,3']bipyrrolidinyl-1'-yl)-phenyl]-8-(4-trifluoromethoxy-benzoyl)-2,8-diaza-spiro[4.5]decan-1-one;
3-[2-methyl-4-((2S,3'S)-2-methyl-[1,3']bipyrrolidinyl-1'-yl)-phenyl]-2,9-diaza-spiro[5.5]undecan-1-one;
3-[4-((2S,3'S)-2-methyl-[1,3']bipyrrolidinyl-1'-yl)-phenyl]-2,9-diaza-spiro[5.5]undecan-1-one;
3-[2-fluoro-4-((2S,3'S)-2-methyl-[1,3']bipyrrolidinyl-1'-yl)-phenyl]-2,9-diaza-spiro[5.5]undecan-1-one;
3-[2-methyl-4-((2S,3'S)-2-methyl-[1,3']bipyrrolidinyl-1'-yl)-phenyl]-9-(pyridine-4-carbonyl)-2,9-diaza-spiro[5.5]undecan-1-one;
9-(furan-3-carbonyl)-2-[2-methyl-4-((2S,3'S)-2-methyl-[1,3']bipyrrolidinyl-1'-yl)-phenyl]-2,9-diaza-spiro[5.5]undecan-1-one;
9-benzoyl-2-[4-((2S,3'S)-2-methyl-[1,3']bipyrrolidinyl-1'-yl)-phenyl]-2,9-diaza-spiro[5.5]undecan-1-one;
9-(4-fluoro-benzoyl)-2-[4-((2S,3'S)-2-methyl-[1,3']bipyrrolidinyl-1'-yl)-phenyl]-2,9-diaza-spiro[5.5]undecan-1-one;
9-cyclohexanecarbonyl-2-[2-fluoro-4-((2S,3'S)-2-methyl-[1,3']bipyrrolidinyl-1'-yl)-phenyl]-2,9-diaza-spiro[5.5]undecan-1-one;
2-[2-fluoro-4-((2S,3'S)-2-methyl-[1,3']bipyrrolidinyl-1'-yl)-phenyl]-9-(tetrahydro-pyran-4-carbonyl)-2,9-diaza-spiro[5.5]undecan-1-one;
9-isopropyl-2-[2-methyl-4-((2S,3'S)-2-methyl-[1,3']bipyrrolidinyl-1'-yl)-phenyl]-2,9-diaza-spiro[5.5]undecan-1-one;
9-cyclohexylmethyl-2-[2-methyl-4-((2S,3'S)-2-methyl-[1,3']bipyrrolidinyl-1'-yl)-phenyl]-2,9-diaza-spiro[5.5]undecan-1-one;
9-cyclopropylmethyl-2-[4-((2S,3'S)-2-methyl-[1,3']bipyrrolidinyl-1'-yl)-phenyl]-2,9-diaza-spiro[5.5]undecan-1-one;
2-[4-((2S,3'S)-2-methyl-[1,3']bipyrrolidinyl-1'-yl)-phenyl]-9-(tetrahydro-pyran-4-yl)-2,9-diaza-spiro[5.5]undecan-1-one;
9-benzyl-2-[2-fluoro-4-((2S,3'S)-2-methyl-[1,3']bipyrrolidinyl-1'-yl)-phenyl]-2,9-diaza-spiro[5.5]undecan-1-one;
2-[2-fluoro-4-((2S,3'S)-2-methyl-[1,3']bipyrrolidinyl-1'-yl)-phenyl]-9-furan-2-ylmethyl-2,9-diaza-spiro[5.5]undecan-1-one;
2-{4-[4-(2S-2-methyl-pyrrolidin-1-yl)-piperidin-1-yl]-phenyl}-2,8-diaza-spiro[4.5]decan-1-one;
2-{4-[4-(2S-2-methyl-pyrrolidin-1-yl)-piperidin-1-yl]-2-trifluoromethyl-phenyl}-2,8-diaza-spiro[4.5]decan-1-one;
2-{4-[4-(2S-2-methyl-pyrrolidin-1-yl)-piperidin-1-yl]-2-fluoro-phenyl}-2,8-diaza-spiro[4.5]decan-1-one;
2-{4-[3-((2S,3'S)-2-methyl-piperidin-1-yl)-pyrrolidin-1-yl]-phenyl}-2,8-diaza-spiro[4.5]decan-1-one;
2-{4-[3-((2S,3'S)-2-methyl-piperidin-1-yl)-pyrrolidin-1-yl]-2-trifluoromethyl-phenyl}-2,8-diaza-spiro[4.5]decan-1-one;
2-{4-[3-((2S,3'S)-2-methyl-piperidin-1-yl)-pyrrolidin-1-yl]-2-fluoro-phenyl}-2,8-diaza-spiro[4.5]decan-1-one;
8-(4-fluoro-benzoyl)-2-{4-[4-(2S-2-methyl-pyrrolidin-1-yl)-piperidin-1-yl]-phenyl}-2,8-diaza-spiro[4.5]decan-1-one;
8-cyclohexanecarbonyl-2-{2-fluoro-4-[4-(2S-2-methyl-pyrrolidin-1-yl)-piperidin-1-yl]-phenyl}-2,8-diaza-spiro[4.5]decan-1-one;
8-(4-fluoro-benzenesulfonyl)-2-{4-[3-((2S,3'S)-2-methyl-piperidin-1-yl)-pyrrolidin-1-yl]-phenyl}-2,8-diaza-spiro[4.5]decan-1-one;
2-{4-[3-((2S,3'S)-2-methyl-piperidin-1-yl)-pyrrolidin-1-yl]-phenyl}-8-(tetrahydro-pyran-4-carbonyl)-2,8-diaza-spiro[4.5]decan-1-one;
8-cyclopentanecarbonyl-2-{4-[3-((2S,3'S)-2-methyl-piperidin-1-yl)-pyrrolidin-1-yl]-2-trifluoromethyl-phenyl}-2,8-diaza-spiro[4.5]decan-1-one;
8-cyclopropylmethyl-2-{2-fluoro-4-[4-(2S-2-methyl-pyrrolidin-1-yl)-piperidin-1-yl]-phenyl}-2,8-diaza-spiro[4.5]decan-1-one;
8-cyclopentylmethyl-2-{2-fluoro-4-[4-(2S-2-methyl-pyrrolidin-1-yl)-piperidin-1-yl]-phenyl}-2,8-diaza-spiro[4.5]decan-1-one;
8-cyclohexylmethyl-2-{4-[3-((2S,3'S)-2-methyl-piperidin-1-yl)-pyrrolidin-1-yl]-2-trifluoromethyl-phenyl}-2,8-diaza-spiro[4.5]decan-1-one;
2-{2-fluoro-4-[3-((2S,3'S)-2-methyl-piperidin-1-yl)-pyrrolidin-1-yl]-phenyl}-8-(tetrahydro-pyran-4-ylmethyl)-2,8-diaza-spiro[4.5]decan-1-one;

2-[4-((2S,3'S)-2-methyl-[1,3']bipyrrolidinyl-1'-yl)-2-trifluoromethyl-phenyl]-8-phenylacetyl-2,8-diaza-spiro[4.5]decan-1-one;

8-(2-methoxy-acetyl)-2-[4-((2S,3'S)-2-methyl-[1,3']bipyrrolidinyl-1'-yl)-2-trifluoromethyl-phenyl]-2,8-diaza-spiro[4.5]decan-1-one;

2-[4-((2S,3'S)-2-methyl-[1,3']bipyrrolidinyl-1'-yl)-2-trifluoromethyl-phenyl]-8-(naphthalene-2-carbonyl)-2,8-diaza-spiro[4.5]decan-1-one;

8-benzoyl-2-[4-((2S,3'S)-2-methyl-[1,3']bipyrrolidinyl-1'-yl)-2-trifluoromethyl-phenyl]-2,8-diaza-spiro[4.5]decan-1-one;

8-(furan-3-carbonyl)-2-[4-((2S,3'S)-2-methyl-[1,3']bipyrrolidinyl-1'-yl)-2-trifluoromethyl-phenyl]-2,8-diaza-spiro[4.5]decan-1-one;

8-furan-2-ylmethyl-2-[4-((2S,3'S)-2-methyl-[1,3']bipyrrolidinyl-1'-yl)-2-trifluoromethyl-phenyl]-2,8-diaza-spiro[4.5]decan-1-one;

8-cyclopropylmethyl-2-[4-((2S,3'S)-2-methyl-[1,3']bipyrrolidinyl-1'-yl)-2-trifluoromethyl-phenyl]-2,8-diaza-spiro[4.5]decan-1-one;

2-[4-((2S,3'S)-2-methyl-[1,3']bipyrrolidinyl-1'-yl)-2-trifluoromethyl-phenyl]-8-(tetrahydro-pyran-4-ylmethyl)-2,8-diaza-spiro[4.5]decan-1-one; and 2-[4-((2S,3'S)-2-methyl-[1,3']bipyrrolidinyl-1'-yl)-2-trifluoromethyl-phenyl]-2,8-diaza-spiro[4.5]decan-1-one;

or a salt thereof.

5. The method according to claim 1, wherein the compound of formula (I) is selected from the group consisting of:

8-cyclopentylmethyl-2-[2-methyl-4-((2R,3'S)-2-methyl-[1,3']bipyrrolidinyl-1'-1)-phenyl]-2,8-diaza-spiro[4.5]decan-1-one;

8-cyclopentylmethyl-2-[2-methyl-4-((2R,3'R)-2-methyl-[1,3']bipyrrolidinyl-1'-1)-phenyl]-2,8-diaza-spiro[4.5]decan-1-one;

8-cyclopentylmethyl-2-[2-methyl-4-((2S,3'R)-2-methyl-[1,3']bipyrrolidinyl-1'-1)-phenyl]-2,8-diaza-spiro[4.5]decan-1-one;

8-cyclopentylmethyl-2-[2-methyl-4-((2S,3'S)-2-methyl-[1,3']bipyrrolidinyl-1'-1)-phenyl]-2,8-diaza-spiro[4.5]decan-1-one;

2-[2-methyl-4-((2R,3'S)-2-methyl-[1,3']bipyrrolidinyl-1'-yl)-phenyl]-8-(4-trifluoromethoxy-benzoyl)-2,8-diaza-spiro[4.5]decan-1-one;

2-[2-methyl-4-((2R,3'R)-2-methyl-[1,3']bipyrrolidinyl-1'-yl)-phenyl]-8-(4-trifluoromethoxy-benzoyl)-2,8-diaza-spiro[4.5]decan-1-one;

2-[2-methyl-4-((2S,3'R)-2-methyl-[1,3']bipyrrolidinyl-1'-yl)-phenyl]-8-(4-trifluoromethoxy-benzoyl)-2,8-diaza-spiro[4.5]decan-1-one;

2-[2-methyl-4-(2-methyl-[1,3']bipyrrolidinyl-1'-yl)-phenyl]-8-(4-trifluoromethoxy-benzoyl)-2,8-diaza-spiro[4.5]decan-1-one;

3-[2-methyl-4-((2S,3'S)-2-methyl-[1,3']bipyrrolidinyl-1'-yl)-phenyl]-2,9-diaza-spiro[5.5]undecan-1-one;

3-[4-((2S,3'S)-2-methyl-[1,3']bipyrrolidinyl-1'-yl)-phenyl]-2,9-diaza-spiro[5.5]undecan-1-one;

3-[2-fluoro-4-((2S,3'S)-2-methyl-[1,3']bipyrrolidinyl-1'-yl)-phenyl]-2,9-diaza-spiro[5.5]undecan-1-one;

9-isopropyl-2-[2-methyl-4-((2S,3'S)-2-methyl-[1,3']bipyrrolidinyl-1'-yl)-phenyl]-2,9-diaza-spiro[5.5]undecan-1-one;

9-cyclohexylmethyl-2-[2-methyl-4-((2S,3'S)-2-methyl-[1,3']bipyrrolidinyl-1'-yl)-phenyl]-2,9-diaza-spiro[5.5]undecan-1-one;

9-cyclopropylmethyl-2-[4-((2S,3'S)-2-methyl-[1,3']bipyrrolidinyl-1'-yl)-phenyl]-2,9-diaza-spiro[5.5]undecan-1-one;

2-[4-((2S,3'S)-2-methyl-[1,3']bipyrrolidinyl-1'-yl)-phenyl]-9-(tetrahydro-pyran-4-yl)-2,9-diaza-spiro[5.5]undecan-1-one;

9-benzyl-2-[2-fluoro-4-((2S,3'S)-2-methyl-[1,3']bipyrrolidinyl-1'-yl)-phenyl]-2,9-diaza-spiro[5.5]undecan-1-one;

2-[2-fluoro-4-((2S,3'S)-2-methyl-[1,3']bipyrrolidinyl-1'-yl)-phenyl]-9-furan-2-ylmethyl-2,9-diaza-spiro[5.5]undecan-1-one;

8-cyclopropylmethyl-2-{2-fluoro-4-[4-(2S-2-methyl-pyrrolidin-1-yl)-piperidin-1-yl]-phenyl}-2,8-diaza-spiro[4.5]decan-1-one;

8-cyclopentylmethyl-2-{2-fluoro-4-[4-(2S-2-methyl-pyrrolidin-1-yl)-piperidin-1-yl]-phenyl}-2,8-diaza-spiro[4.5]decan-1-one;

2-{2-fluoro-4-[3-((2S,3'S)-2-methyl-piperidin-1-yl)-pyrrolidin-1-yl]-phenyl}-8-(tetrahydro-pyran-4-ylmethyl)-2,8-diaza-spiro[4.5]decan-1-one;

8-furan-2-ylmethyl-2-[4-((2S,3'S)-2-methyl-[1,3']bipyrrolidinyl-1'-yl)-2-trifluoromethyl-phenyl]-2,8-diaza-spiro[4.5]decan-1-one;

8-cyclopropylmethyl-2-[4-((2S,3'S)-2-methyl-[1,3']bipyrrolidinyl-1'-yl)-2-trifluoromethyl-phenyl]-2,8-diaza-spiro[4.5]decan-1-one; and 2-[4-((2S,3'S)-2-methyl-[1,3']bipyrrolidinyl-1'-yl)-2-trifluoromethyl-phenyl]-8-(tetrahydro-pyran-4-ylmethyl)-2,8-diaza-spiro[4.5]decan-1-one;

or a salt thereof.

* * * * *